US012655478B2

(12) United States Patent
Chang et al.

(10) Patent No.: US 12,655,478 B2
(45) Date of Patent: Jun. 16, 2026

(54) HIGH PERFORMANCE SPATIAL MAPPING OF INDIVIDUAL TARGETS USING RELEASABLE HANDSHAKE SEQUENCES

(71) Applicant: Takara Bio USA, Inc., San Jose, CA (US)

(72) Inventors: Christina Chang, Palo Alto, CA (US); Stephen P.A. Fodor, Palo Alto, CA (US); Hei Mun Christina Fan, Palo Alto, CA (US); Anaram Shahravan, Palo Alto, CA (US); Julie Wilhelmy, Palo Alto, CA (US); Bertrand Yeung, Palo Alto, CA (US)

(73) Assignee: Takara Bio USA, Inc., San Jose, CA (US)

( * ) Notice: Subject to any disclaimer, the term of this patent is extended or adjusted under 35 U.S.C. 154(b) by 0 days.

(21) Appl. No.: 18/622,603

(22) Filed: Mar. 29, 2024

(65) Prior Publication Data

US 2024/0344118 A1      Oct. 17, 2024

Related U.S. Application Data

(63) Continuation of application No. PCT/US2024/022002, filed on Mar. 28, 2024.

(60) Provisional application No. 63/557,828, filed on Feb. 26, 2024, provisional application No. 63/455,502, filed on Mar. 29, 2023.

(51) Int. Cl.
*C12Q 1/6855*          (2018.01)
*C12N 15/10*          (2006.01)

(52) U.S. Cl.
CPC ....... *C12Q 1/6855* (2013.01); *C12N 15/1093* (2013.01)

(58) Field of Classification Search
None
See application file for complete search history.

(56) References Cited

U.S. PATENT DOCUMENTS

| | | | |
|---|---|---|---|
| 7,613,571 | B2 | 11/2009 | Doyle et al. |
| 8,053,744 | B2 | 11/2011 | Bortolin |
| 8,124,362 | B2 | 2/2012 | Akhavan-Tafti |
| 8,835,358 | B2 | 9/2014 | Fodor et al. |
| 9,085,798 | B2 | 7/2015 | Chee |
| 9,290,808 | B2 | 3/2016 | Fodor et al. |
| 9,290,809 | B2 | 3/2016 | Fodor et al. |
| 9,315,857 | B2 | 4/2016 | Fu et al. |
| 9,476,101 | B2 | 10/2016 | Pregibon et al. |
| 9,567,645 | B2 | 2/2017 | Fan et al. |
| 9,567,646 | B2 | 2/2017 | Fan et al. |
| 9,598,736 | B2 | 3/2017 | Fan et al. |
| 9,637,799 | B2 | 5/2017 | Fan et al. |
| 9,708,659 | B2 | 7/2017 | Fodor et al. |
| 9,727,810 | B2 | 8/2017 | Fodor et al. |

| | | | |
|---|---|---|---|
| 9,783,847 | B2 | 10/2017 | Chee et al. |
| 9,816,137 | B2 | 11/2017 | Fodor et al. |
| 9,845,502 | B2 | 12/2017 | Fodor et al. |
| 10,000,800 | B2 | 6/2018 | Chee |
| 10,002,316 | B2 | 6/2018 | Fodor et al. |
| 10,030,261 | B2 | 7/2018 | Frisen et al. |
| 10,047,394 | B2 | 8/2018 | Fodor et al. |
| 10,059,991 | B2 | 8/2018 | Fodor et al. |
| 10,119,165 | B2 | 11/2018 | Chee |
| 10,131,958 | B1 | 11/2018 | Fan et al. |
| 10,151,003 | B2 | 12/2018 | Fan et al. |
| 10,202,646 | B2 | 2/2019 | Fodor et al. |
| 10,208,356 | B1 | 2/2019 | Fan et al. |
| 10,227,639 | B2 | 3/2019 | Levner et al. |
| 10,253,375 | B1 | 4/2019 | Fan et al. |
| 10,266,883 | B2 | 4/2019 | Chee |
| 10,266,884 | B2 | 4/2019 | Chee |
| 10,308,982 | B2 | 6/2019 | Chee |
| 10,392,661 | B2 | 8/2019 | Fodor et al. |
| 10,472,669 | B2 | 11/2019 | Chee |
| 10,480,022 | B2 | 11/2019 | Chee |

(Continued)

FOREIGN PATENT DOCUMENTS

| | | |
|---|---|---|
| WO | WO-2009091934 A1 | 7/2009 |
| WO | WO-2010127186 A1 | 11/2010 |

(Continued)

OTHER PUBLICATIONS

Russell et al. "Slide-tags Enables Single-nucleus Barcoding for multimodal spatial genomics". Nature, 625(7993), pp. 101-109, Published Dec. 13, 2023 (Year: 2023).*
Vandereyken et al. "Methods and applications for single-cell and spatial multi-omics". Nat Rev Genet 24, 494-515, published Mar. 2, 2023 (Year: 2023).*
Armani, M. et al., 2D-PCR: a method of mapping DNA in tissue sections, Lab Chip, 9:3526-3534 (2009).
Biermann et al. Dissecting the treatment-naive ecosystem of human melanoma brain metastasis. Cell 185(14):2591-2608.e30 (2022).
Choe et al. Advances and Challenges in Spatial Transcriptomics for Developmental Biology. Biomolecules 13(1):156 (2023).

(Continued)

*Primary Examiner* — Heather Calamita
*Assistant Examiner* — Jessica D Parisi
(74) *Attorney, Agent, or Firm* — Fenwick & West LLP

(57) ABSTRACT

Systems, methods, and compositions for generating a spatial map of a distribution of targets of a sample are described. A system for mapping targets can include a substrate; and a distribution of functionalized features associated with the substrate, wherein a representative feature of the distribution of functionalized features comprises: one or more functionalized molecules coupled to the representative feature, the one or more molecules including at least: a handshake sequence comprising a reactive portion, a barcode segment serving as a spatial address, and a cleavable linker configured to allow the handshake sequence to be released from the representative feature in response to a stimulus. The system can be used to tag nuclei, cells, and/or other target components of a sample.

16 Claims, 25 Drawing Sheets

(56) References Cited

U.S. PATENT DOCUMENTS

| | | | |
|---|---|---|---|
| 10,501,793 B2 | 12/2019 | Chee | |
| 10,619,203 B2 | 4/2020 | Fodor et al. | |
| 10,662,467 B2 | 5/2020 | Chee | |
| 10,662,468 B2 | 5/2020 | Chee | |
| 10,913,975 B2 | 2/2021 | So et al. | |
| 10,914,730 B2 | 2/2021 | Chee | |
| 10,927,419 B2 | 2/2021 | Fan et al. | |
| 10,954,570 B2 | 3/2021 | Fan et al. | |
| 10,961,566 B2 | 3/2021 | Chee | |
| 10,983,113 B2 | 4/2021 | Chee | |
| 10,996,219 B2 | 5/2021 | Chee | |
| 11,001,878 B1 | 5/2021 | Chee | |
| 11,001,879 B1 | 5/2021 | Chee | |
| 11,008,607 B2 | 5/2021 | Chee | |
| 11,021,737 B2 | 6/2021 | Church et al. | |
| 11,149,310 B2 | 10/2021 | Fisher et al. | |
| 11,162,132 B2 | 11/2021 | Frisen et al. | |
| RE48,913 E | 2/2022 | Fodor et al. | |
| 11,293,051 B2 | 4/2022 | Church et al. | |
| 11,293,052 B2 | 4/2022 | Church et al. | |
| 11,293,054 B2 | 4/2022 | Levner et al. | |
| 11,299,767 B2 | 4/2022 | Church et al. | |
| 11,299,774 B2 | 4/2022 | Frisen et al. | |
| 11,352,659 B2 | 6/2022 | Frisen et al. | |
| 11,390,912 B2 | 7/2022 | Frisen et al. | |
| 11,473,142 B2 | 10/2022 | Beechem et al. | |
| 11,479,809 B2 | 10/2022 | Frisen et al. | |
| 11,613,773 B2 | 3/2023 | Frisen et al. | |
| 11,618,929 B2 | 4/2023 | Fan et al. | |
| 11,624,088 B2 | 4/2023 | Fan et al. | |
| 11,702,706 B2 | 7/2023 | Fan et al. | |
| 2006/0040286 A1 | 2/2006 | Mirkin et al. | |
| 2006/0275782 A1 | 12/2006 | Gunderson et al. | |
| 2010/0105104 A1 | 4/2010 | Okano et al. | |
| 2010/0267015 A1 | 10/2010 | Szasz | |
| 2011/0212848 A1 | 9/2011 | Duffy et al. | |
| 2012/0065081 A1 | 3/2012 | Chee | |
| 2012/0289428 A1 | 11/2012 | Duffy et al. | |
| 2014/0194324 A1 | 7/2014 | Gormley et al. | |
| 2014/0243238 A1 | 8/2014 | Seligmann et al. | |
| 2015/0344942 A1 | 12/2015 | Frisen et al. | |
| 2016/0024576 A1 | 1/2016 | Chee | |
| 2016/0253584 A1* | 9/2016 | Fodor | C12Q 1/6813 |
| | | | 235/494 |
| 2016/0289740 A1 | 10/2016 | Fu et al. | |
| 2016/0312276 A1 | 10/2016 | Fu et al. | |
| 2016/0333403 A1 | 11/2016 | Chee et al. | |
| 2017/0058339 A1 | 3/2017 | Chee et al. | |
| 2017/0058340 A1 | 3/2017 | Chee et al. | |
| 2017/0058345 A1 | 3/2017 | Chee et al. | |
| 2017/0088881 A1 | 3/2017 | Chee et al. | |
| 2018/0057873 A1 | 3/2018 | Zhou et al. | |
| 2018/0180601 A1 | 6/2018 | Pedersen et al. | |
| 2018/0251825 A1 | 9/2018 | Stoeckius et al. | |
| 2019/0262831 A1 | 8/2019 | West et al. | |
| 2019/0309355 A1 | 10/2019 | Chee | |
| 2020/0048701 A1 | 2/2020 | Chee | |
| 2020/0048702 A1 | 2/2020 | Chee | |
| 2020/0048703 A1 | 2/2020 | Chee | |
| 2020/0224266 A1 | 7/2020 | Fodor et al. | |
| 2020/0354788 A1 | 11/2020 | Fodor et al. | |
| 2021/0062272 A1 | 3/2021 | Williams et al. | |
| 2021/0095331 A1 | 4/2021 | Fan et al. | |
| 2021/0123040 A1 | 4/2021 | Macosko et al. | |
| 2021/0155982 A1 | 5/2021 | Yin et al. | |
| 2021/0164039 A1 | 6/2021 | Wang et al. | |
| 2021/0214785 A1 | 7/2021 | Stoeckius | |
| 2021/0230681 A1 | 7/2021 | Patterson et al. | |
| 2021/0238670 A1 | 8/2021 | Chee | |
| 2021/0238671 A1 | 8/2021 | Chee | |
| 2021/0238675 A1 | 8/2021 | Bava | |
| 2021/0262019 A1 | 8/2021 | Alvarado Martinez et al. | |
| 2021/0265017 A1 | 8/2021 | Dutta et al. | |
| 2021/0382061 A1 | 12/2021 | Yun et al. | |
| 2022/0002791 A1 | 1/2022 | Frisen et al. | |
| 2022/0010367 A1 | 1/2022 | Ramachandran Iyer et al. | |
| 2022/0017952 A1 | 1/2022 | Fan et al. | |
| 2022/0033805 A1 | 2/2022 | Srivatsan et al. | |
| 2022/0119871 A1 | 4/2022 | Regev et al. | |
| 2022/0180975 A1 | 6/2022 | Regev et al. | |
| 2022/0220555 A1 | 7/2022 | Beechem et al. | |
| 2022/0251632 A1 | 8/2022 | Regier et al. | |
| 2023/0057339 A1 | 2/2023 | Fodor et al. | |
| 2023/0212659 A1 | 7/2023 | Fan et al. | |
| 2024/0052405 A1 | 2/2024 | Fan et al. | |

FOREIGN PATENT DOCUMENTS

| | | | |
|---|---|---|---|
| WO | WO-2012140224 A1 | 10/2012 | |
| WO | WO-2014060483 A1 | 4/2014 | |
| WO | WO-2016162309 A1 | 10/2016 | |
| WO | WO-2017075293 A1 | 5/2017 | |
| WO | WO-2019199579 A1 * | 10/2018 | C12Q 1/682 |
| WO | WO-2019178164 A1 * | 9/2019 | B01L 3/502761 |
| WO | WO-2019213254 A1 | 11/2019 | |
| WO | 2020123320 A2 | 6/2020 | |
| WO | WO-2020123309 A1 | 6/2020 | |
| WO | WO-2021096814 A1 | 5/2021 | |
| WO | WO-2022015925 A1 | 1/2022 | |
| WO | WO-2023023308 A1 | 2/2023 | |
| WO | WO-2024020395 A2 * | 1/2024 | C12N 15/1065 |
| WO | 2024138050 A1 | 6/2024 | |
| WO | 2024197279 A1 | 9/2024 | |
| WO | WO-2024206652 A2 | 10/2024 | |

OTHER PUBLICATIONS

Di Bella et al. Molecular logic of cellular diversification in the mouse cerebral cortex. Nature 595(7868):554-559 (2021).
Dong et al. Deciphering spatial domains from spatially resolved transcriptomics with an adaptive graph attention auto-encoder. Nat Commun 13(1):1739 (2022).
Fan, Christina H et al. Expression Profiling. Combinatorial Labeling of Single Cells for Gene Expression Cytometry. Science 347(6222):1258367, pp. 1-10 (2015).
Huang et al.: Centrifugal micro-channel array droplet generation for highly parallel digital PCR. Lap on a Chip 17(2):235-240 (2017).
Kamath et al. Single-cell genomic profiling of human dopamine neurons identifies a population that selectively degenerates in Parkinson's disease. Nat Neurosci 25(5):588-595 (2022).
Kim, H. et al. Nuclear oligo hashing improves differential analysis of single-cell RNA-seq. Nature Communications 13:2666 (2022).
Lee, Y. et al. XYZeq: Spatially resolved single-cell RNA sequencing reveals expression heterogeneity in the tumor microenvironment. Sci. Adv., 7(17):eabg4755 (2021).
Li et al. A comprehensive benchmarking with practical guidelines for cellular deconvolution of spatial transcriptomics. Nat Commun 14(1):1548 (2023).
Mantri et al. Spatiotemporal transcriptomics reveals pathogenesis of viral myocarditis. Nat Cardiovasc Res. 1(10):946-960 (2022).
Marshall et al. High-resolution Slide-seqV2 spatial transcriptomics enables discovery of disease-specific cell neighborhoods and pathways. iScience 25(4):104097 (2022).
Moses et al. Museum of spatial transcriptomics. Nat Methods 19(5):534-546 (2022).
[No Authors Listed] Method of the Year 2020: spatially resolved transcriptomics. Nat Methods 18(1):1 (2021).
Noel et al. Principles of Spatial Transcriptomics Analysis: A Practical Walk-Through in Kidney Tissue. Front Physiol 12:809346 (2022).
Palla et al. Squidpy: a scalable framework for spatial omics analysis. Nat Methods 19(2):171-178 (2022).
PCT/US2021/041741 International Search Report and Written Opinion dated Dec. 16, 2021.
PCT/US2022/040859 International Invitation to Pay Additional Fees dated Nov. 3, 2022.
PCT/US2022/040859 International Search Report and Written Opinion dated Jan. 9, 2023.

(56)                    References Cited

OTHER PUBLICATIONS

PCT/US2024/022002 International Search Report and Written Opinion dated Sep. 4, 2024.

PCT/US2024/022002 Invitation to Pay Additional Fees dated Jun. 14, 2024.

Rodriques et al. Slide-seq: A scalable technology for measuring genome-wide expression at high spatial resolution. Science 363(6434):1463-1467 (Supplementary Material) (2019).

Rodriques, Samuel et al. Slide-seq: A scalable technology for measuring genome-wide expression at high spatial resolution. Science 363(6434):1463-1467 (2019).

Shen et al. Recent advances in high-throughput single-cell transcriptomics and spatial transcriptomics. Lab on a Chip 22:4774 (2022).

Soto et al. Controlled assembly of mesoscale structures using DNA as molecular bridges. J Am Chem 124:8508-8509 (2002).

Southern, E.M. et al. Arrays of complementary oligonucleotides for analysing the hybirdisation behaviour of nucleic acids. Nucleic Acids Research 22(8):1368-1373 (1994).

Southern, E.M. et al., DNA chips: analysing sequence by hybridization to oligonucleotides on a large scale. Technical Focus 12(3):110-5 (1996).

Srivatsan, S. et al. Embryo-scale, single cell spatial transcriptomics. Science. Author manuscript; pp. 16 (2022).

Stahl, Patrik L et al. Visualization and Analysis of Gene Expression in Tissue Sections by Spatial Transcriptomics. Science 353(6294):78-82 (2016).

Stickels, Robert R et al. Highly sensitive spatial transcriptomics at near-cellular resolution with Slide-seqV2. Nature biotechnology 39(3):1-7 (2021).

U.S. Appl. No. 17/376,396 Office Action dated Apr. 22, 2022.

U.S. Appl. No. 17/895,633 Office Action dated Apr. 6, 2023.

U.S. Appl. No. 17/895,633 Office Action dated Oct. 12, 2023.

U.S. Appl. No. 18/492,620 Office Action dated Apr. 22, 2024.

U.S. Appl. No. 18/492,620 Office Action dated Jul. 24, 2024.

Valignet et al. Reversible self-assembly and directed assembly of DNA-linked micrometer-sized colloids. PNAS USA 102(12):4225-4229 (2005).

Van Den Brink et al. Single-cell sequencing reveals dissociation-induced gene expression in tissue subpopulations. Nat Methods 14(10):935-936 (2017).

Vickovic, Sanja et al. High-definition Spatial Transcriptomics for in Situ Tissue Profiling. Nature methods 16(10):987-990 (2019).

Wang et al. Spatial transcriptomic reconstruction of the mouse olfactory glomerular map suggests principles of odor processing. Nat Neurosci 25(4):484-492 (2022).

Williams et al. An introduction to spatial transcriptomics for biomedical research. Genome Med 14(1):68 (2022).

Xu et al. CoSTA: unsupervised convolutional neural network learning for spatial transcriptomics analysis. BMC Bioinformatics 22(1):397 (2021).

Yu et al. Spatial transcriptomics technology in cancer research. Front Oncol 12:1019111 (2022).

Curio. Curio Seeker Spatial Mapping Kit. Dec. 31, 2023; [retrieved on Sep. 30, 2024]. Available at URL:https://curiobioscience.com/documentation/ pp. 1-4.

Federal Register 84(4):35-64 (2019), 36 pages.

Leigh,et al. RNA in situ hybridization. Nature Communications:1-19 (2018).

Patent Cooperation Treaty, International Search Report and Written Opinion, PCT Patent Application No. PCT/US2024/034537 dated Oct. 25, 2024, 8 pages.

* cited by examiner

Layer 15

Substrate 110a

⬤ Functionalized Particle 120a

○ Cell 10 (or other single target/analyte)

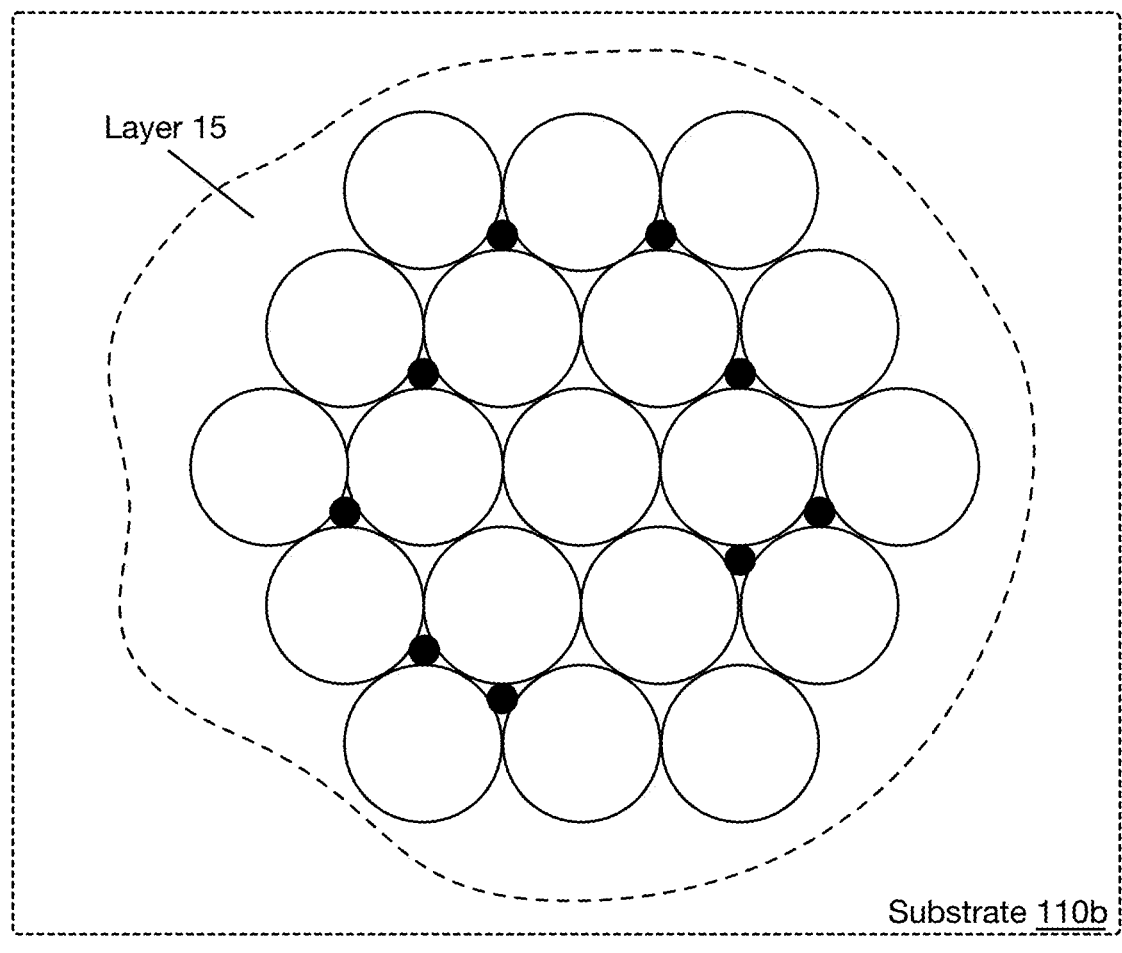
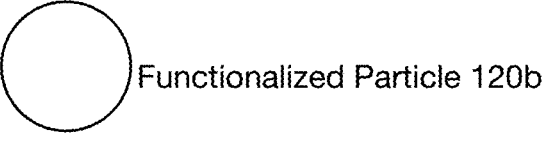Functionalized Particle 120b
● Nuclei 15
FIGURE 1C

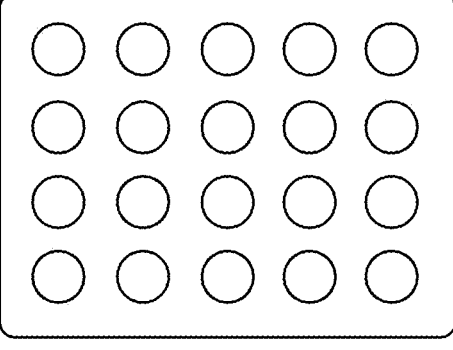
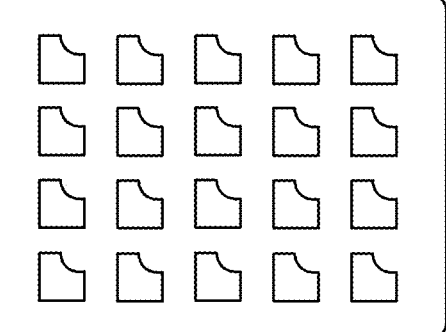
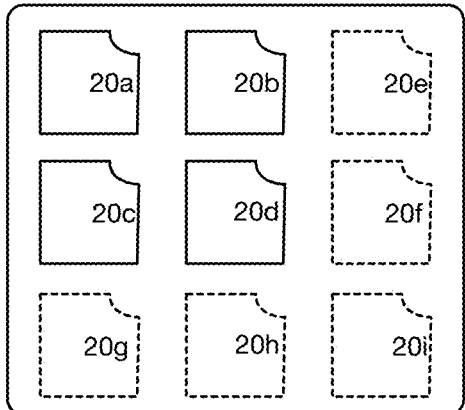
FIGURE 1F

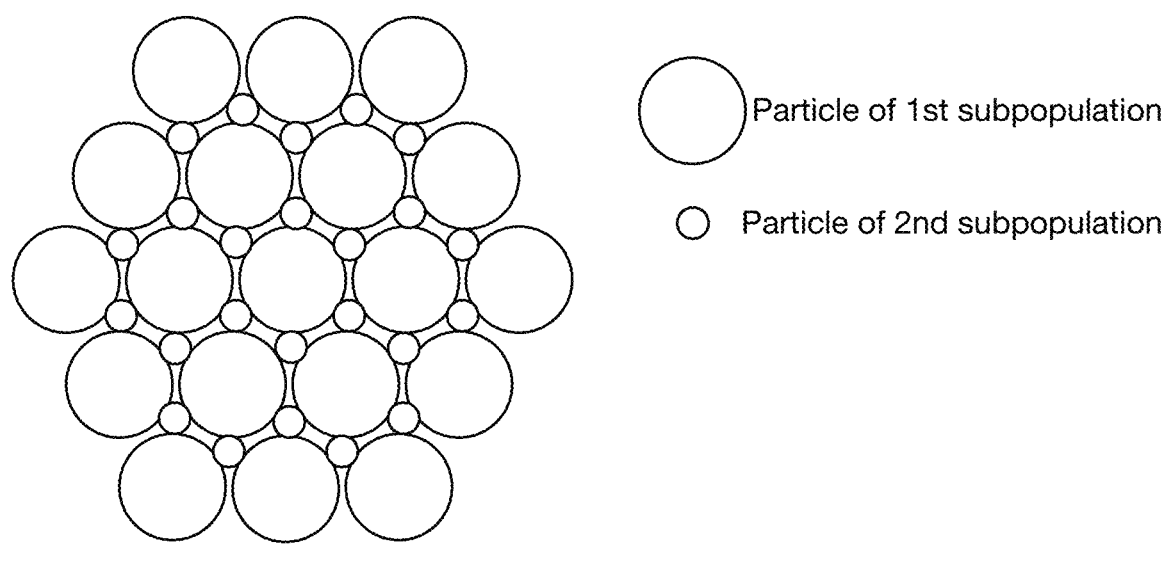
Particle of 1st subpopulation
Particle of 2nd subpopulation
1st particle type               2nd particle type
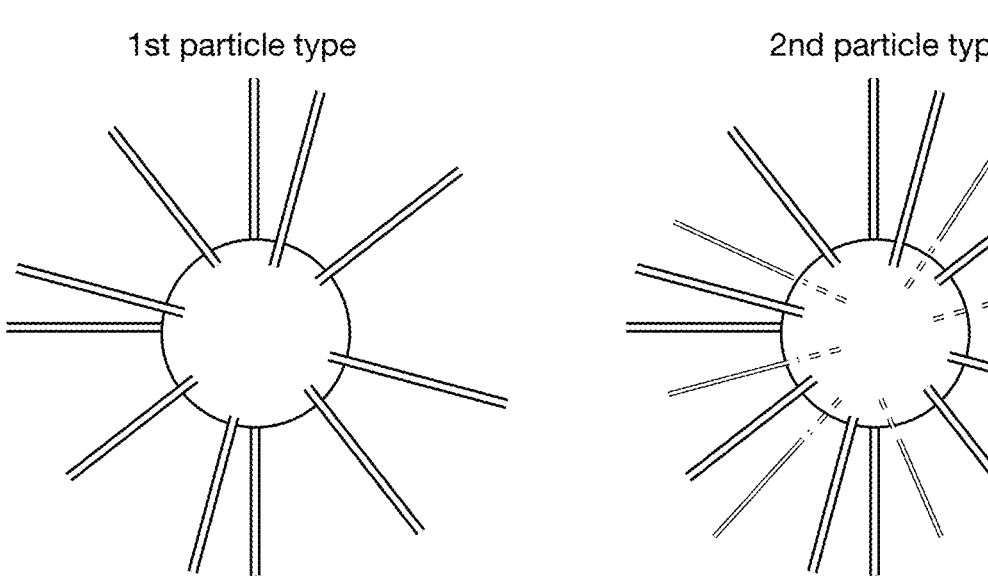
3rd particle type
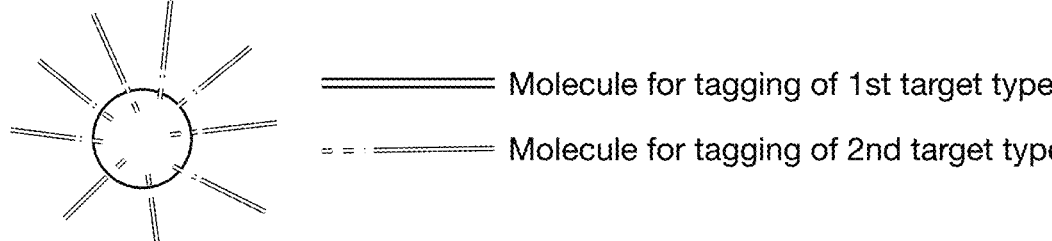
Molecule for tagging of 1st target type
Molecule for tagging of 2nd target type
FIGURE 1G Functionalized molecule for nuclei target tagging
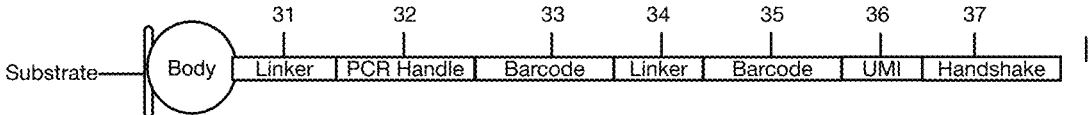
Functionalized molecule for cytoplasmic mRNA target tagging
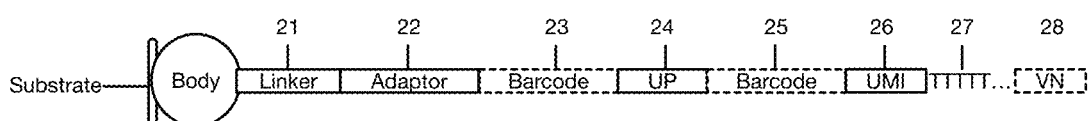
FIGURE 1H
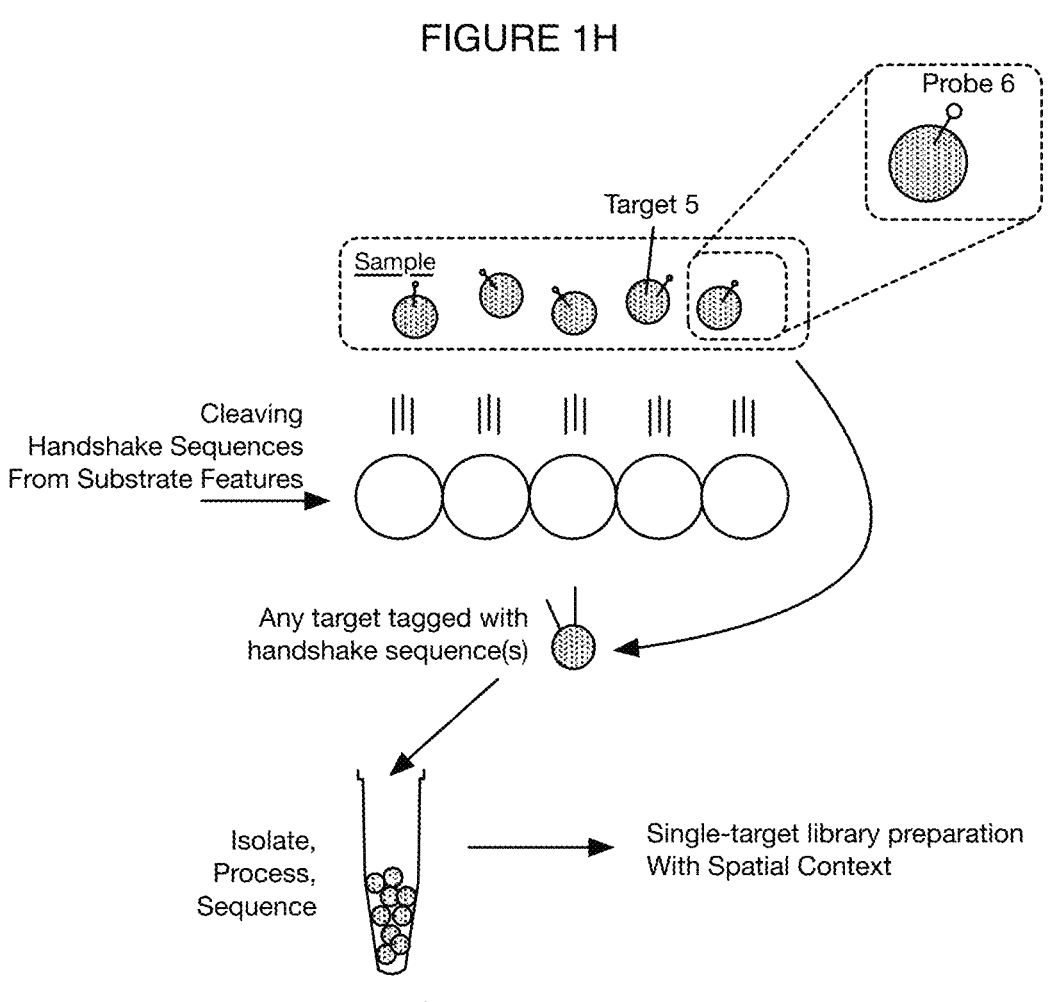
FIGURE 1I

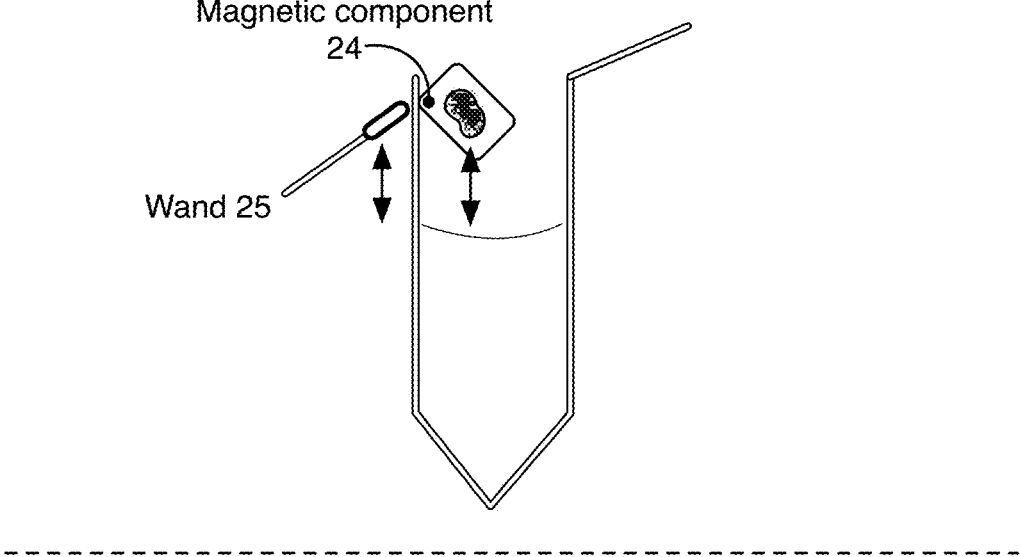
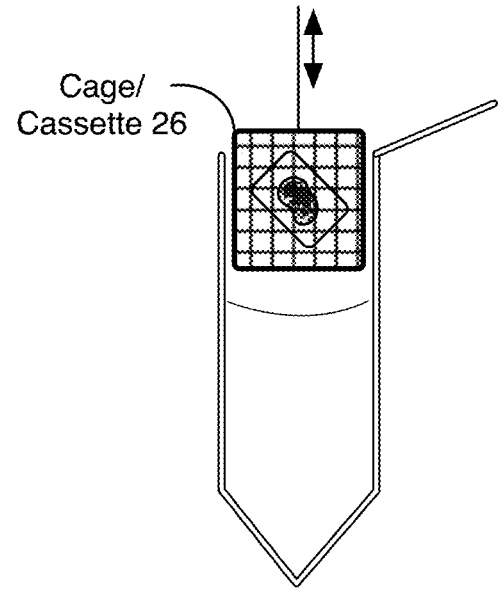
FIGURE 5

Support Structure 200b

Tip
210b

Sample

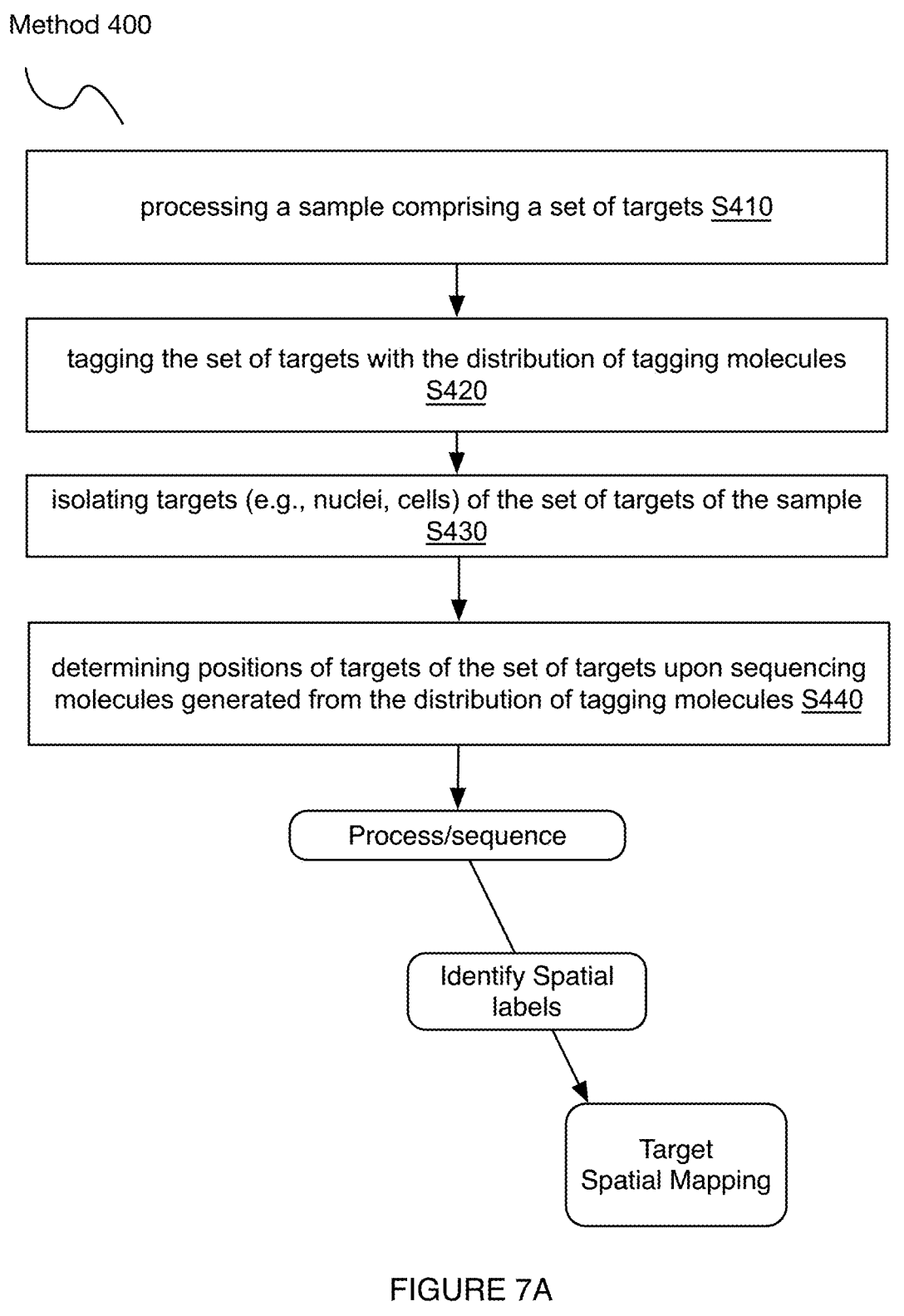

Method 400

```
┌─────────────────────────────────────────────────────────────────┐
│                                                                   │
│      processing a sample comprising a set of targets S410         │
│                                                                   │
└─────────────────────────────────────────────────────────────────┘
                                  │
                                  ▼
┌─────────────────────────────────────────────────────────────────┐
│                                                                   │
│    tagging the set of targets with the distribution of tagging    │
│                      molecules S420                               │
│                                                                   │
└─────────────────────────────────────────────────────────────────┘
                                  │
                                  ▼
┌─────────────────────────────────────────────────────────────────┐
│                                                                   │
│  isolating targets (e.g., nuclei, cells) of the set of targets    │
│                    of the sample S430                             │
│                                                                   │
└─────────────────────────────────────────────────────────────────┘
                                  │
                                  ▼
┌─────────────────────────────────────────────────────────────────┐
│                                                                   │
│  determining positions of targets of the set of targets upon      │
│  sequencing molecules generated from the distribution of tagging  │
│                      molecules S440                               │
│                                                                   │
└─────────────────────────────────────────────────────────────────┘
                                  │
                                  ▼
                       ╭─────────────────────╮
                       │   Process/sequence  │
                       ╰─────────────────────╯
                                   ╲
                                    ╲
                            ╭──────────────────╮
                            │ Identify Spatial │
                            │      labels      │
                            ╰──────────────────╯
                                         ╲
                                          ╲
                                  ╭──────────────────╮
                                  │      Target      │
                                  │ Spatial Mapping  │
                                  ╰──────────────────╯
```

FIGURE 7A

Method 400

Method 500

generating a set of labelled cells, upon tagging a set of cells with a first set of oligonucleotides S510 seating the set of labeled cells at interstitial spaces of a distribution of functionalized particles coupled to a substrate S520 generating a single cell sequencing library from amplicons generated from a set of reactions involving the set of labelled cells and molecules of the distribution of functionalized particles S530 returning a single cell analysis of the set of cells upon sequencing the single cell sequencing library S540

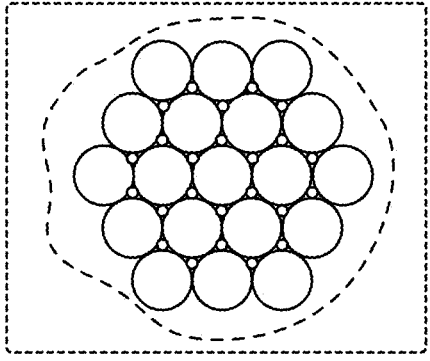

FIGURE 7C

Method 600

| |
|---|
| generating a set of labelled nuclei, upon tagging a set of nuclei with a first set of oligonucleotides S610 |

↓

| |
|---|
| seating the set of labeled nuclei at interstitial spaces of a distribution of functionalized particles coupled to a substrate S620 |

↓

| |
|---|
| generating a single nucleus sequencing library from amplicons generated from a set of reactions involving the set of labelled nuclei and molecules of the distribution of functionalized particles S630 |

↓

| |
|---|
| returning a single nucleus analysis of the set of nuclei upon sequencing the single nucleus sequencing library S640 |

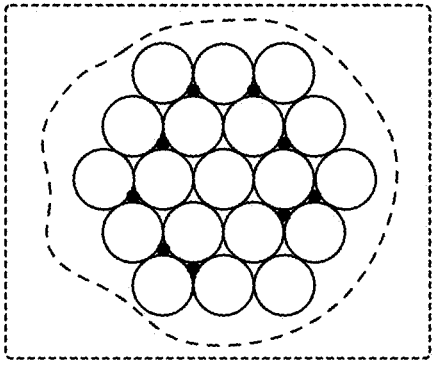

FIGURE 7D

Medium (e.g., hydrogel, polaxomer)

Single Cell/Particle/Analyte

Variation of substrate with
Distribution of functionalized features

Method 700

combining a set of functionalized particles with a set of single cells and/or a set of single nuclei S710

↓ retaining single cells and/or single nuclei within recesses of the set of functionalized particles S720

↓ stabilizing the set of functionalized particles with associated single cells and/or single nuclei within a matrix S730

↓ lysing the set of single cells with a lysis buffer S740

↓ performing a hybridization operation with content, wherein the hybridization operation tags target content of a single cell or single nucleus S750

↓ transitioning the matrix from the set phase to the non-set phase, in coordination with performing a reverse transcription operation, a second strand synthesis operation, and a cDNA amplification operation after the hybridization operation 760

↓ generating a sequencing library from amplicons generated from the cDNA amplification operation 770

↓ returning a single cell and/or single nucleus analysis of the set of cells/ set of nuclei upon processing the sequencing library S780

FIGURE 10

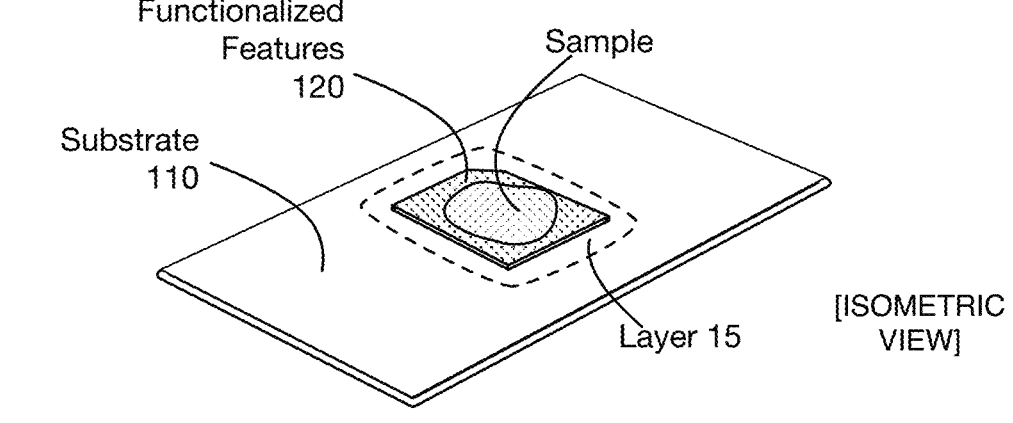
Functionalized
Features
120
Sample
Substrate
110
Layer 15
[ISOMETRIC
VIEW]
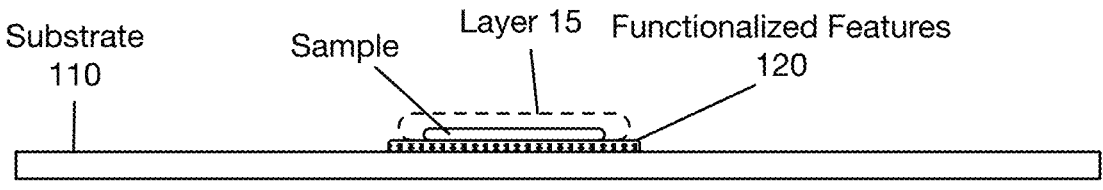
Substrate
110
Sample
Layer 15
Functionalized Features
120
[SIDE
VIEW]
FIGURE 11A Method 800

Position sample over functionalized particles S810

Position layer over sample S820

Transmit heat to sample and/or layer S830

Sample processing (e.g., hybridization) S840

Background
Artifact

Smearing
Artifact

Method 900

omitting mapping of data from a first category of particles of the distribution of functionalized particles, wherein sequences acquired from the first category of particles each have UMI counts above a first threshold S910 omitting mapping of data from a second category of particles of the distribution of functionalized particles, wherein particles of the second category of particles each have an associated density greater than a second threshold  S920 omitting mapping of data from a third category of particles of the distribution of functionalized particles, wherein particles of the third category of particles each have an associated density greater than a third threshold S930

FIGURE 13

HIGH PERFORMANCE SPATIAL MAPPING OF INDIVIDUAL TARGETS USING RELEASABLE HANDSHAKE SEQUENCES

CROSS-REFERENCE

This application is a continuation of International Application No. PCT/US24/22002, filed on Mar. 28, 2024, which claims the benefit of U.S. Provisional Application No. 63/557,828, filed on Feb. 26, 2024, and U.S. Provisional Application No. 63/455,502, filed on Mar. 29, 2023, which are each incorporated in its entirety herein by this reference.

TECHNICAL FIELD

This invention relates generally to the sample characterization field, and more specifically to new and useful systems, methods, and compositions for characterizing sample targets, including single cells and single nuclei.

BACKGROUND

With an increased interest in understanding distributions of particular target analytes within a biological sample, improved compositions, methods, and systems that allow for analyte mapping are becoming highly valuable. Current technologies are limited in resolution (e.g., with respect to location of target analytes), ability to characterize locations in multiple dimensions, ability to characterize locations across scales of magnitude, ability to characterize different types of analytes, ability to characterize locations of targets in situ, and/or in other manners. Additionally, streamlined approaches for spatial mapping with the ability to process and recover sample targets associated with single cells and single nuclei are needed. Thus, there is a need in the sample characterization field for new and useful systems, methods, and compositions for characterizing sample targets, with spatial mapping capability.

SUMMARY OF THE INVENTION

Currently, methods and systems for spatially characterizing analytes of a sample (e.g., in situ, in vitro, etc.) are limited in relation to: resolution (e.g., with respect to potential number of target analytes that can be characterized per unit area or volume), low signal to noise ratio (e.g., due to high levels of background noise); recovery rate of material from single nuclei and/or single cells of a sample being spatially characterized; diffusion of targets intended to be characterized from originating positions within a tissue sample; underutilization of spaces between interaction sites due to manufacturing or physical constraints, ability to characterize targets of a sample in multiple dimensions, ability to simultaneously characterize different types of analytes (e.g., with whole transcriptome characterization capability), and/or in other manners.

Accordingly, this disclosure describes embodiments, variations, and examples of systems, methods, and compositions for performing spatial biology (e.g., spatial transcriptomics, spatial proteomics, spatial multi-omics, etc.), in a manner that provides broader transcriptome coverage while achieving high levels of spatial resolution. The disclosure describes embodiments, variations, and examples of methods and systems for spatially localizing individual nuclei and/or individual cells of a sample being processed. Based upon reactive sequences of functionalized molecules involved, the disclosure describes embodiments, variations, and examples of methods and systems for spatially localizing other sample targets (e.g., proteins, etc.) in space.

An aspect of the disclosure provides embodiments, variations, and examples of systems, methods, and compositions for efficient tagging of target material (e.g., DNA, RNA, miRNA, proteins, small molecules, single analytes, multi-analytes, etc.) to enable analyses for characterizing locations of target material in space. For nucleic acid targets, handshake sequences of compositions described can include complementary molecules to the nucleic acid targets (e.g., with complementarity based upon polyA/polyT interactions, with complementarity based upon interactions between polyadenylated mRNAs and other nucleic acids incorporating U bases and/or T bases (e.g., consecutively, non-consecutively, with a pattern, without a pattern), with complementarity based upon sequences of specific targets to be tagged, with complementarity based upon sequences of platforms for tagging molecules, etc.). For protein targets or small molecule targets, handshake sequences, described in further detail below, can include antibodies or aptamers conjugated with specific nucleic acid sequences for detection.

Functionalized molecules incorporating handshake sequences can further include one or more modifications that enhance diffusion to sample targets (e.g., nuclei). For instance, functionalized molecules incorporating handshake sequences can include one or more lipid moieties that enhance diffusion to nuclei and/or other intracellular components.

Targets can include cytoplasmic targets, intracellular targets, or other targets on the surface of or within a cell (or components of a cell). For instance, targets can include cytoplasmic targets and targets of or associated with nuclei of cells from the same tissue, such that simultaneous mapping of multiple target types in a highly parallel manner can be achieved. Alternatively, generated maps of nuclei/cell targets can be integrated with other maps characterizing distributions of other tissue components, according to methods described. Targets can additionally or alternatively include protein targets and/or other spatially distributed targets of a sample.

In one embodiment, characterizing nuclei of a sample can include generating a set of labelled nuclei, upon tagging a set of nuclei with a first set of oligonucleotides (e.g., oligonucleotides having handshake sequences that uniquely tag each nucleus of the set of nuclei with one or more barcodes that can serve as spatial addresses); dissociating and seating the set of labeled nuclei at interstitial spaces of a distribution of functionalized particles coupled to a substrate (e.g., such as an embodiment, variation, or example of the systems described in U.S. patent application Ser. No. 17/895,633 filed on 25 Aug. 2022 and titled "Systems and Methods for Characterizing Locations of Target Analytes in Multi-Dimensional Space", which is herein incorporated in its entirety by this reference), wherein each functionalized particle contacts no more than one labelled nucleus of the set of labelled nuclei; generating a single nucleus sequencing library from amplicons generated from a set of reactions involving the set of labelled nuclei and molecules of the distribution of functionalized particles; an returning a single nucleus analysis of the set of nuclei upon processing the single nucleus sequencing library. Exemplary outputs of processes described can include a single nucleus whole transcriptome library (e.g., representing gene expression information of the set of nuclei), and a spatial library, which contains the spatial location of each nucleus of the set of nuclei. In variations, the substrate can be covered (e.g., with optimum cutting temperature compound or another material) to reduce diffusion. Furthermore, in the scenarios described, the substrate may not need to be decoded, since the nuclei are labelled with handshake sequences that uniquely tag each nucleus of the set of nuclei with one or more barcodes that can serve as spatial addresses.

In one embodiment, characterizing cells (e.g., single cells) of a sample can include: generating a set of labelled cells, upon tagging a set of cells with a first set of oligonucleotides (e.g., oligonucleotides having handshake sequences that uniquely tag each cell of the set of cells with one or more barcodes that can serve as spatial addresses); dissociating and seating the set of labeled cells at interstitial spaces of a distribution of functionalized particles coupled to a substrate (e.g., such as an embodiment, variation, or example of the systems described in U.S. patent application Ser. No. 17/895,633 filed on 25 Aug. 2022 and titled "Systems and Methods for Characterizing Locations of Target Analytes in Multi-Dimensional Space", which is herein incorporated in its entirety by this reference), wherein each functionalized particle contacts no more than one labelled cell of the set of labelled cells; generating a single cell sequencing library from amplicons generated from a set of reactions involving the set of labelled cells and molecules of the distribution of functionalized particles; and returning a single cell analysis of the set of cells upon processing the single cell sequencing library. Exemplary outputs of processes described can include a single cell whole transcriptome library (e.g., representing gene expression information of the set of cells), and a spatial library, which contains the spatial location of each cell of the set of cells. In variations, the substrate can be covered (e.g., with optimum cutting temperature compound or another material) to reduce diffusion. Furthermore, in the scenarios described, the substrate may not need to be decoded, since the cells are labelled with handshake sequences that uniquely tag each nucleus of the set of nuclei with one or more barcodes that can serve as spatial addresses.

In one embodiment for characterization of a set of single cells or single nuclei in multiple dimensions, a method can include: combining a set of functionalized particles with a set of single cells and/or a set of single nuclei, wherein a ratio of a number of functionalized particles to a number of single cells and/or single nuclei is greater than one (e.g., 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, etc.); retaining single cells and/or single nuclei within recesses (e.g., crevices, pores, other surface features, etc.) of the set of functionalized particles (e.g., where a single cell or single nucleus associates with no more than one functionalized particle of the set of functionalized particles); stabilizing the set of functionalized particles with associated single cells and/or single nuclei within a matrix (e.g., hydrogel matrix, other matrix), wherein the matrix can be transitioned between a set phase and a non-set phase, and wherein the matrix allows for diffusion of material below a first size threshold to and/or between the set of functionalized particles, and prevents material above a second size threshold from diffusion; lysing the set of single cells (if single cells are present) with a lysis buffer, with or without increasing a temperature of the lysis buffer, wherein the lysis buffer is introduced to the set of single cells through the matrix; performing a hybridization operation with content (e.g., mRNA content, other nucleic acid content, conjugated protein content, etc.) of the set of single cells and/or set of single nuclei with the set of functionalized particles, wherein content of a single cell or single nucleus can hybridize with more than one functionalized particle of the set of functionalized particles, wherein the hybridization operation tags target content of a single cell or single nucleus using one or more handshake sequences described; transitioning the matrix from the set phase to the non-set phase, in coordination with performing a reverse transcription operation, a second strand synthesis operation, and a cDNA amplification operation after the hybridization operation; generating a sequencing library from amplicons generated from the cDNA amplification operation; and returning a single cell and/or single nucleus analysis of the set of cells/set of nuclei upon processing the sequencing library, wherein subsets of the set of functionalized particles associated with target material from a single cell/single nucleus are associated based upon a barcode (e.g., a spatial barcode, a cell barcode) having a nucleotide sequence (e.g., a stochastic sequence) associated with the single cell/single nucleus. When combined with spatial information (e.g., with use of spatial barcodes described), the methods described can enable associations between genotypic features and phenotypic features of biological sample material.

Labeling of nuclei or cells of a sample can include: processing a sample comprising a set of nuclei with a substrate comprising a distribution of functionalized particles (e.g., with capability for decoding of positions of the functionalized particles by way of barcode sequences that can serve as spatial address sequences, as described below); tagging the set of nuclei or cells with released handshake sequences (e.g., upon cleaving functionalized molecules from the functionalized particles), where the handshake sequences include respective barcode sequences that serve as spatial address sequences; isolating nuclei of the set of nuclei and/or other targets of the sample; and determining positions of nuclei of the set of nuclei upon sequencing molecules generated from the distribution of functionalized particles. Optionally, in some embodiments, methods can include tagging (e.g., microfluidic tagging, tagging within microwells, tagging within partitions, tagging within droplets of an emulsion) and barcoding of nuclei targets (e.g., mRNAs, other nuclei targets) with barcodes that can serve as spatial addresses after isolation of nuclei. Tagging can involve tagging using a membrane (e.g., nitrocellulose membrane, other membrane, etc.) from which handshake sequences can be released. Identification of nuclei targets can further optionally be performed using optical detection of nuclei targets tagged with probes during tagging and barcoding of nuclei, without sequencing.

In embodiments, a substrate can include functionalized particles including a first subset of functionalized particles for tagging nuclei targets of a sample (e.g., using handshake sequences described), and a second subset of functionalized particles for tagging cytoplasmic targets of the sample. In other embodiments, a substrate can include functionalized particles for tagging only nuclei targets (e.g., nuclear RNA) of a sample with handshake sequences. In embodiments, a substrate can include functionalized particles for tagging only cytoplasmic targets (e.g., cytoplasmic RNA) of a sample (e.g., with handshake sequences, or as described in applications incorporated by reference). In embodiments a substrate can be functionalized with functionalized particles to tag whole single cells of a sample with handshake sequences.

In relation to tissue processing, the disclosure provides methods, systems, and devices for tagging targets (e.g., cytoplasmic targets) that are exposed during tissue processing (e.g., tissue slicing, tissue sectioning) with sequences that serve as spatial addresses, as well as spatially labeling of individual nuclei and/or other intracellular components (e.g., with handshake sequences, as described below). Methods described can include determining locations of cell bodies (e.g., based upon nuclei positions) of a sample, and performing single-cell analysis techniques in coordination with spatial analysis of single-cell and other targets, where analysis techniques can include single nucleus RNA-seq (e.g., snRNA-seq, scRNA-seq, etc.), t-cell receptor (TCR) analyses, b-cell receptor (BCR) analyses (e.g., with receptor-ligand characterizations), ATAC-seq for assessment of chromatin accessibility, processing of nuclei and non-nuclei targets of formalin-fixed and paraffin-embedded (FFPE) samples, generation of Hi-C sequencing libraries, generation of other single cell sequencing libraries, analysis of nuclear DNA, analysis of nuclear proteins, and/or other analyses.

Aspects of the disclosure also provide embodiments, variations, and examples of systems, methods, and devices for accurately determining positions (e.g., relative positions, positions on a substrate having functionalized particles, positions relative to another reference point or surface, etc.) of nuclei of a sample. In embodiments where a nucleus is tagged using handshake sequences of molecules of functionalized particles, tagging of the nucleus can involve tagging the nucleus with different molecules associated with different spatial positions (e.g., upon photocleaving the handshake molecules for diffusion toward the nucleus). As such, determining the position of the nucleus can involve determining the position based upon a subset of positions corresponding to a subset of barcode sequences of molecules that tagged the nucleus, where the barcode sequences serve as spatial addresses, and where an approximate spatial address can be determined from the barcode sequences (e.g., upon determining a centroid position from spatial addresses of the respective barcode sequences). In variations, the approximated position of the nucleus can be determined from an average position of the subset of stochastic barcodes (e.g., a centroid of positions of the subset of stochastic barcodes). In variations, nuclei can be tagged using a combination of cleavable and non-cleavable molecules, such that positions of the nuclei can be determined from barcode positions of cleavable and non-cleavable molecules (e.g., as a weighted centroid of positions, where positions of non-cleavable components are weighted more heavily than positions of cleavable components). As such, the position estimated from the barcodes serving as spatial addresses can be an estimation of the location in or on a sample, in or on a feature (e.g., functionalized particle) or a combination thereof.

The location of each cell/nucleus tagged with handshake sequences can be determined from sequencing of generated libraries. For instance, cell barcode sequences of functionalized molecules also including handshake sequences can include UMI sequences and the location of each cell/nucleus in a processed sample is determined based on sequences (e.g., a number of sequences) of UMIs sequenced for each spatial position (determined from barcodes that can serve as spatial addressses) having the same cell barcode/UMI sequence.

In relation to tagging and mapping of nuclei targets, the disclosure provides embodiments, variations, and examples of systems, methods, and compositions for generating spatial maps with improved recovery rate for nuclei targets (e.g., in relation to actual numbers of nuclei targets present) to greater than 15%, greater than 20%, greater than 25%, greater than 30%, greater than 35%, greater than 40%, greater than 45%, greater than 50%, greater than 60%, greater than 70%, or greater. In examples, the disclosure provides embodiments, variations, and examples of systems, methods, and compositions for generating spatial maps with improved recovery rate for nuclei targets (e.g., in relation to actual numbers of nuclei targets present), where the number of nuclei recovered from a tissue section (e.g., embryonic tissue section, other tissue section) can be greater than 50,000, greater than 60,000, greater than 70,000, greater than 80,000, greater than 90,000, greater than 100,000, greater than 110,000, greater than 120,000, greater than 130,000, greater than 140,000, greater than 150,000, greater than 160,000, greater than 170,000, greater than 180,000, greater than 190,000, greater than 200,000, greater than 250,000, greater than 300,000 or greater (e.g., for a tissue section from 5 microns through 40 microns thick, and with a surface area greater than 3 mm×3 mm, greater than 10 mm×10 mm, or of another suitable dimension, where various tissue types are described). Recovery of nuclei can be determined upon dissociation of the sample and counting of nuclei (e.g., through a cytometry-based method). Alternatively, recovery of nuclei can be determined upon performing sequencing of nuclei. Alternatively, recovery of nuclei can be determined upon spatially positioning nuclei during mapping (e.g., after sequencing of nuclei and corresponding barcode sequences that serve as spatial addresses). In particular, nuclei retention is typically poor due to losses during sample processing and isolation of nuclei, and the disclosure provides methods for improved recovery rate and retention of nuclei. The recovery rate can be determined as a percentage of nuclei originally present in the sample.

In relation to tagging of nuclei and/or other targets of a sample with functionalized molecules of functionalized particles, functionalized molecules can include unique molecular identifiers (UMIs). The disclosure provides embodiments, variations, and examples of systems, methods, and compositions for recovering greater than 2000 UMIs per nucleus/target, greater than 2500 UMIs per nucleus/target, greater than 3000 UMIs per nucleus/target, greater than 3500 UMIs per nucleus/target, greater than 4000 UMIs per nucleus/target, greater than 4500 UMIs per nucleus/target, greater than 5000 UMIs per nucleus/target, greater than 5500 UMIs per nucleus/target, greater than 6000 UMIs per nucleus/target, greater than 6500 UMIs per nucleus/target, greater than 7000 UMIs per nucleus/target, greater than 7500 UMIs per nucleus/target, greater than 8000 UMIs per nucleus/target, greater than 8500 UMIs per nucleus/target, greater than 9000 UMIs per nucleus/target, greater than 9500 UMIs per nucleus/target, greater than 10,000 UMIs per nucleus/target, greater than 20,00 UMIs per nucleus/target, or greater. As such, systems, methods, and devices described can achieve higher UMI capture per nucleus/target, in relation to existing single-cell techniques and other state-of-the-art techniques.

Aspects of the disclosure also provide embodiments, variations, and examples of systems for generating spatial maps of a set of targets of a sample, where the empty/unused space between substrate features (e.g., beads or other particle bodies, rods, protrusions, recesses, ridges, valleys, channels, wells, oligonucleotide spots, etc.) for generating such spatial maps is less than 45 micrometers, 40 micrometers, 35 micrometers, 30 micrometers, 25 micrometers, 20 micrometers, 15 micrometers, 10 micrometers, 9 micrometers, 8 micrometers, 7 micrometers, 6 micrometers, 5 micrometers, 5 micrometers, 4 micrometers, 3 micrometers, 2 micrometers, 1 micrometer, 0.5 micrometers, 0.25 micrometers, 0.1 micrometers, or intermediate distances.

Aspects of the disclosure provide embodiments, variations, and examples of systems, methods, and compositions for spatially characterizing samples in multidimensions (e.g., 2D, 3D, 4D with a time component), in relation to one or more of: whole tissue structures, tissue pieces (e.g., as in histology, in relation to biopsied tissues, in relation to seeded natural scaffolds, in relation to seeded synthetic scaffolds (e.g., cell-seeded hydrogel scaffolds, cell-seeded polaxamer scaffolds, etc.) in relation to frozen tissue specimens (e.g., fresh frozen tissue samples that are sectioned), in relation to formalin-fixed and paraffin-embedded (FFPE) specimens, fresh frozen plasma, frozen cell suspensions, cell suspensions retained in a medium/hydrogel medium organs, whole organisms, organoids, cell suspensions, single cells, organelles, sub-organelle structures, intra-organelle components, mitochondrial targets, viruses, microorganisms, and other natural structures. Cells can include mammalian cells, bacteria, microbes, plant cells, fungal cells, or other cells/cell-like components.

Location characterization can additionally or alternatively be performed in relation to non-naturally occurring structures, such as microwells, microarrays, scaffolds, gels, and other non-naturally occurring structures. For instance, handshake sequences that can interact with targets (e.g., by diffusion, etc.) can be incorporated onto surfaces of structures described.

The invention(s) can additionally or alternatively have in situ and/or in vivo applications, with infusion of functionalized particles into a sample (e.g., into a cell, into a tissue, into an organ, etc.). Examples of infusion can include one or more of: injection, electroporation, use of vectors (e.g., viral vectors), and other infusion methods.

In relation to mapping of different target types using the same unit of the system for tagging multiple target types (e.g., with handshake sequences), the invention(s) can achieve mapping of single cell types/subtypes of a sample along with mapping of distributions of nuclei targets, cytoplasmic targets, and/or other targets, from the same sample and using the same unit of the system (e.g., distribution of functionalized particles coupled to a substrate).

Aspects of the disclosure provide embodiments, variations, and examples of methods for generating a spatial map of a distribution of targets of a sample by a set of processes, where the set of processes can include: receiving a sample at a substrate comprising a distribution of functionalized particles, each of the distribution of functionalized particles including a barcode sequence (e.g., stochastic barcode sequence that serves as a spatial address) paired with a position on the substrate (with decoding of the positions of the stochastic barcode sequences prior to use for target mapping); preparing the sample for interactions between the distribution of targets of the sample and the distribution of functionalized particles (e.g., upon transmitting heat to a surface of the substrate opposite the distribution of functionalized particles for frozen samples); applying a set of reactions to the sample at the substrate; obtaining a set of sequences of a population of molecules generated from the set of reactions, the set of sequences associated with the distribution of targets labeled using the stochastic barcode sequences of the distribution of functionalized particles, and returning a set of positions of the distribution of targets upon processing the set of sequences.

Aspects of the disclosure also provide embodiments, variations, and examples of systems, methods, and compositions configured for high levels of parallel sample processing, where, upon receiving a sample at a substrate, the sample can be re-frozen (e.g., at 0° C., at –20° C., at –80° C., etc.) for a duration of time prior to performing subsequent processing steps (e.g., post-thaw) for target mapping, without significant degradation in mapping performance (e.g., in relation to performance and quality metrics described).

In relation to quality metrics, aspects of the disclosure also provide embodiments, variations, and examples of systems, methods, and compositions that achieve threshold levels of performance in relation to various quality metrics. In examples, the invention(s) can achieve one or more of: number of paired end sequencing reads greater than a threshold level (e.g., greater than 100,000,000, greater than 200,000,000, greater than 500,000,000, etc.); percentage of read pairs having proper structure greater than a threshold percentage (e.g., 60%, 70%, 80%, 90%, 99%, etc.), where proper structure is determined by comparing the read sequence to the actual synthesized sequence (e.g., order of barcode regions, universal primer regions, unique molecule identifiers, polyT tails, etc.); total number of barcode sequences read per substrate greater than a threshold (e.g., 40,000, 50,000, 60,000, 70,000, 80,000, 90,000, 100,000, etc.); percentage of barcode sequences recovered greater than a threshold (e.g., 60%, 70%, 80%, 90%, 99%, etc.); percent of proper reads matched to a barcode sequence greater than a threshold (e.g., 60%, 70%, 80%, 90%, 99%, etc.); percent of proper reads in genes greater than a threshold (e.g., 60%, 70%, 80%, 90%, 99%, etc.); percent of proper reads matched to barcode sequences and genic sequences greater than a threshold (e.g., 60%, 70%, 80%, 90%, 99%, etc.); percent of raw useful reads (matched to a barcode sequences and genic sequences) greater than a threshold (e.g., 30%, 40%, 50%, 60%, 70%, 80%, 90%, 99%, etc.); average reads per unique molecule identifier (UMI) satisfying a threshold condition; total number of genes in matched bead barcodes greater than a threshold (e.g., 5,000, 10,000, 15,000, 20,000, 25,000, 30,000, 35,000, 40,000, 50,000, etc.); total number of UMIs in matched bead barcodes greater than a threshold (e.g., greater than 5,000, 000, 10,000,000, 15,000,000, 20,000,000, 25,000,000, etc.); average reads per bead greater than a threshold (e.g., 100, 200, 300, 400, 500, 600, 700, 800, 900, 1000, etc.); average number of UMIs per bead greater than a threshold (e.g., 100, 200, 300, 400, 500, 600, 700, 800, 900, 1000, etc.); average number of genes per bead greater than a threshold (e.g., 100, 200, 300, 400, 500, 600, 700, 800, 900, 1000, etc.); top percents of reads, UMIs, and/or genes per bead greater than a threshold (e.g., 100, 200, 300, 400, 500, 600, 700, 800, 900, 1000, etc.); average percent of mitochondrial UMIs per bead satisfying a threshold condition; average percent of ribosomal protein UMIs per bead satisfying a threshold condition; average percent of ribosomal RNA UMIs per bead satisfying a threshold condition; and/or other suitable quality metrics.

Aspects of the disclosure also provide embodiments, variations, and examples of systems, methods, and non-naturally-occurring compositions for facilitating tagging of target biological material from a sample and characterizing locations of target biological material in space (e.g., two dimensional space, three dimensional space). Such compositions can include materials that have been modified from their natural states (e.g., in terms of providing structural differences from natural compositions). Furthermore, the invention(s) relate to combinations of materials, where the combinations of materials are non-naturally occurring (e.g., there is no naturally occurring counterpart to the compositions described and claimed).

Aspects of the disclosure also provide embodiments, variations, and examples of systems, methods, and compositions for location characterization in multiple dimensions, where functionalized molecules distributed across sites of the composition(s) described can be implemented in monolayer form (e.g., with manufacturing processes to apply composition units in monolayer or near-monolayer form, with systems that apply magnetic or other forces to form monolayers, etc.), with sample (e.g., tissue, cells) positioned adjacent the monolayer for subsequent processing and mapping. Alternatively, functionalized molecules distributed across sites of the composition(s) described can be infused into a sample/specimen (e.g., by magnetic force, by electroporation, by using vectors, etc.). Alternatively, functionalized molecules distributed across sites of the composition(s) described can be coupled to a surface of a sample/specimen (e.g., by chemical binding, by magnetic binding, by other binding), in order to enable surface mapping. Alternatively, functionalized molecules distributed across sites of the composition(s) described can be guided or otherwise retained in 3D structures (e.g., in grids, in non-grid structures), such as microwells, microarrays (e.g., with nucleic acids capturing particles), scaffolds (e.g., hydrogels), or other 3D structures. In a related application, physical or other forces can be used to define structures (e.g., close packed structures) for distributions of functionalized molecules distributed across sites that interact with samples to enable mapping. Alternatively, in relation to location characterization in multiple dimensions, functionalized molecules distributed across sites of composition(s) described can be randomly distributed in space.

Aspects of the disclosure also provide embodiments, variations, and examples of systems, methods, and compositions for applications in spatial transcriptomics. Compositions, methods, and systems described can be used for mapping of targets in a sample over time, in order to understand disease pathology and progression (e.g., spread of targets and changes in expression over time).

Aspects of the disclosure also provide embodiments, variations, and examples of systems, methods, and compositions for mapping of nuclei targets of a sample, along with other targets (e.g., cytoplasmic targets, protein targets, etc.) and/or cell types and/or cell subtypes of the sample, using distributions of functionalized particles, with molecules functionalized for capturing different target types. Upon tagging (e.g., with handshake sequences), recovery, and amplification of nuclei targets, further processing steps can be performed in order to generate characterizations, including but not limited to methylation status, epigenetic aspects (e.g., control of nuclear architecture, epigenetic changes in relation to previous instances of sampling or sampling from related sources), chromatin accessibility using transposase-accessible chromatin with sequencing ATAC-Seq, cytotoxicity status, and/or other characterizations.

Aspects of the disclosure also provide embodiments, variations, and examples of systems, methods, and compositions for mapping of targets of an FFPE sample according to a set of processes including: deparaffinization of the sample (prior to application to a substrate with functionalized particles, after application to a substrate with functionalized particles), optionally permeabilizing the FFPE sample, tagging of nuclei targets of the FFPE sample along with cytoplasmic targets of the sample (e.g., using handshake sequences of cleavable functionalized molecules described in further detail below), retrieving nuclei targets (e.g., with magnetic bodies of functionalized particles implemented, with sample homogenization, with exposure of nuclei using detergents, with electroporation, etc.) thereby retrieving nuclei targets with improved recovery rates for FFPE samples, and performing downstream analyses and mapping of multiple target types from the FFPE sample. For target tagging and spatial contextualization of targets, an FFPE tissue sample can processed by dissolving paraffin in a solvent (e.g. xylene or mineral oil); dissolving the tissue at a temperature (e.g., between 4 C to 90 C); rehydrating the tissue using a gradient of ethanol from 100% to 0% ethanol (EtOH); transferring the rehydrated tissue to a volume of a first buffer comprising a buffering agent, a detergent and an ionic strength between 100 mM and 200 mM (where the first buffer includes protease inhibitors, proteases, and/or BSA; preparing single nuclei using a buffer including 10 mM Tris, 0.49% CHAPS, 146 mM NaCl, 1 mM CaCl2, 21 mM MgCl2, and 0.01% BSA (CST), or alternatively, using a buffer including 10 mM Tris, 0.03% Tween-20, 146 mM NaCl, 1 mM CaCl2, 21 mM MgCl2, and 0.01% BSA (TST). In one example embodiment, the buffers are used during extraction of nuclei from the FFPE tissue.

In one variation, a method for mapping nuclei targets of an FFPE sample can include: receiving an FFPE sample at a substrate including a distribution of functionalized particles for tagging nuclei targets of the FFPE sample; drying the FFPE sample and the substrate for a duration of time; performing a deparaffinization operation upon the FFPE sample at the substrate; performing a reverse crosslinking operation with the FPPE sample at the substrate; photocleaving linkers of functionalized molecules of the distribution of functionalized particles, thereby releasing the functionalized molecules for tagging nuclei targets of the FFPE sample; performing a tissue dissociation and nuclei isolation operation upon the FFPE sample; and generating a spatial map of the nuclei targets of the FPPE sample upon sequencing molecules of the FFPE sample after the tissue dissociation and nuclei isolation operation.

In variations, processing an FFPE sample for target mapping (e.g., of cytoplasmic targets, of nuclei targets, etc.) can include dissolving extracellular matrix (ECM) of the FFPE sample (e.g., with collagenase); performing a reverse crosslinking operation in order to reverse crosslinks of molecular components of the FFPE sample (e.g., prior to polyadenylation of nucleic acid targets of the FFPE sample); implementation of high pH buffers for facilitate polyadenylation and/or deparaffinization of FFPE samples; and performing other suitable steps to increase accessibility of RNA material for tagging and subsequent mapping.

In variations, increasing accessibility of nucleic acid targets (e.g., RNA material of an FFPE sample) can include improving efficacy of nucleic acid extraction from a sample, preventing nucleic acid losses into buffers prior to performing hybridization steps, and increasing efficacy of reverse crosslinking steps. In one such variation, increasing accessibility of nucleic acid targets can include performing RNA processing in situ, followed by performing hybridization of targets with molecules of a distribution of functionalized particles (as described herein). In one example, the method can include: increasing accessibility of RNA targets of a sample, generating cDNA copies of the RNA targets upon performing a reverse transcription operation, adding a reactive site to 3' ends of the cDNA copies with template switching oligonucleotides (TSOs), digesting RNA of the sample, permeabilizing cells of the sample, capturing the cDNA copies with the reactive sites; and extending molecules of the functionalized particles with the cDNA copies.

Aspects of the disclosure also provide embodiments, variations, and examples of systems, methods, and compositions for multi-omic characterizations of a sample, with mapping of cytoplasmic targets, nuclei targets, protein/antibody targets (e.g., with oligo-coupled tagging components for protein targets), cluster regularly interspaced short palindromic repeats (CRISPR) targets (e.g., guide RNAs with A-tails or other features that can be tagged and amplified), and other targets tagged from the same sample.

Applications of the methods described can be used to enhance characterizations of various tissue types and/or single cell and/or single nuclei characterizations. For instance, in relation to neurological tissue or neurological cells, mapping of multiple target types of the sample can characterize neurons, neuron subtypes, neuron membrane aspects, neuron nuclei aspects, dendritic aspects, axon aspects, oligodendrocyte aspects, hillock aspects, myelin sheath aspects, node of Ranvier aspects, synaptic end bulb aspects, axon terminal aspects, and thus neuron processes performed.

Applications of the methods described can also be used to enhance characterizations of various tissue types and/or single cell and/or single nuclei characterizations of sample material including one or more of: nervous system biological material, cardiovascular system biological material, integumentary system biological material, skeletal system biological material, muscular system biological material, respiratory system biological material, digestive system biological material, endocrine system biological material, urinary system biological material, and reproductive system biological material. Cellular material can be associated with normal and diseased states, including one or more of: cancer cells, circulating tumor cells, metastatic cells, benign cells, or any combination thereof. In relation to tissue or cell types, mapping of multiple target types of the sample can characterize nuclei, cell, and tissue subcomponents, as well as cellular functions performed. As such, methods described can enhance single-nuclei analysis, single-cell analysis, and/or tissue characterization analysis, by providing spatial localization information for nuclei and cells of a sample, on top of expression data generated through tagging and sequencing or other techniques:

Aspects of the disclosure also provide embodiments, variations, and examples of systems that can perform complex characterizations, without requiring traditional platforms for performing such characterizations. For instance, in relation to performing single cell characterizations (which traditionally require complex platforms for single cell partitioning, spatial characterization platforms, and sequencing platforms), the disclosure can streamline operations for performing such characterizations. In one embodiment, samples of cells, nuclei, or other cellular components can be barcoded (e.g., with one or more barcode sequences, where a barcode sequence can serve as a spatial address), and one or more portions of the sample can be applied to a substrate with functionalized particles (e.g., after forming a suspension with such components, after centrifugation, after purification, after enrichment, after freezing, after slicing, etc.) for target tagging, sequencing, and mapping, without involvement of complex single cell processing setups (e.g., traditionally involving microwells or other partitioning technologies).

Additional aspects and advantages of the present disclosure will become readily apparent to those skilled in this art from the following detailed description, wherein only illustrative embodiments of the present disclosure are shown and described. The present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference in their entireties for all purposes and to the same extent as if each individual publication, patent, or patent application was specifically and individually indicated to be incorporated by reference. Furthermore, where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

BRIEF DESCRIPTION OF THE DRAWINGS

FIG. 1C depicts a schematic of an embodiment of a system for partitioning single nuclei that have been tagged with handshake sequences.

FIG. 1F depicts arrayed substrate components for characterizing locations of targets in space, using releasable handshake sequences.

FIG. 1G depicts variations of particle subpopulations and molecules for target tagging, of an embodiment of a system for characterizing locations of target analytes in space, using releasable handshake sequences.

FIG. 1H depicts variations of functionalized molecules comprising tagging elements.

FIG. 1I depicts a variation of tagging pre-labelled sample targets having probes with handles corresponding to handshake sequences.

FIG. 5 depicts variations of components that facilitate sample processing with respect to characterizing locations of targets in space, using releasable handshake sequences.

FIG. 7A depicts a flowchart of an embodiment of a method for characterizing locations of targets in space, using releasable handshake sequences.

FIG. 7C depicts a schematic of a flowchart of a method for characterizing locations of targets in space, using releasable handshake sequences and partitioning substrates.

FIG. 7D depicts a schematic of a flowchart of a method for characterizing locations of targets in space, using releasable handshake sequences and partitioning substrates.

FIG. 10 depicts a schematic of a flowchart of a method for sample component processing.

FIG. 11A depicts an exemplary system configuration for preventing smearing artifacts and/or background artifacts.

FIG. 13 depicts a variation of a method for preventing smearing artifacts and/or background artifacts.

DETAILED DESCRIPTION OF THE INVENTION(S)

Figure 1A:
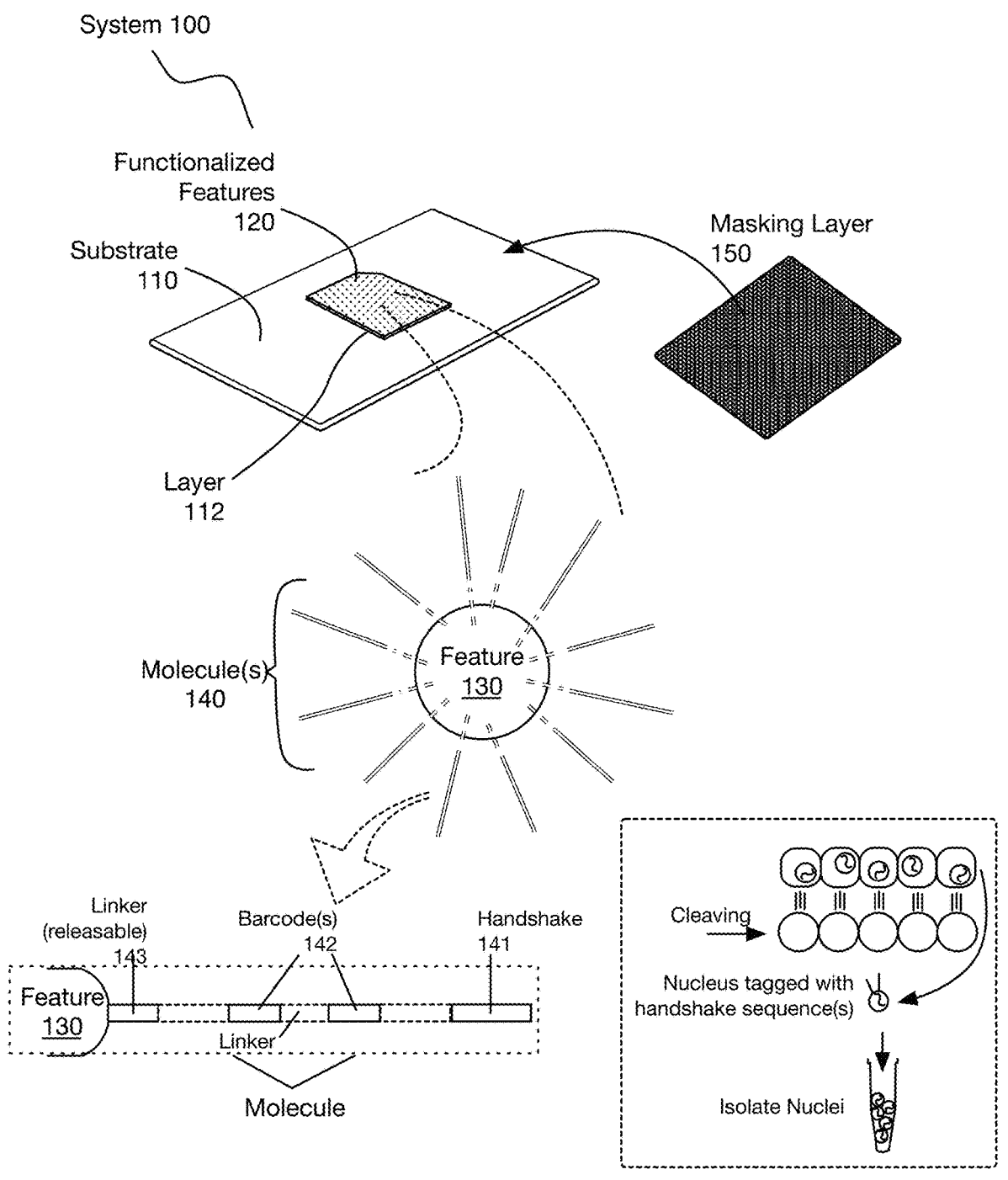
FIG. 1A depicts a schematic of an embodiment of a system for characterizing locations of targets in space, using releasable handshake sequences.

While various embodiments of the invention have been shown and described herein, it will be obvious to those skilled in the art that such embodiments are provided by way of example only. Numerous variations, changes, and substitutions can occur to those skilled in the art without departing from the invention. It should be understood that various alternatives to the embodiments of the invention described herein can be employed.

1. GENERAL OVERVIEW

The present disclosure covers systems, devices, methods performed by such systems and devices, and methods of manufacturing and assembling such devices.

The disclosure provides systems and methods for labeling of nuclei and/or cells of a sample, where an embodiment of a method for labelling can include: processing a sample comprising a set of nuclei or cells with a substrate comprising a distribution of handshake sequences (e.g., with capability for decoding of positions of the functionalized molecules by way of barcode sequences that can serve as spatial addresses of the functionalized particles, as described below); tagging the set of nuclei and/or cells with one or more handshake sequences comprising the barcode sequences (e.g., upon releasing the handshake sequences from the substrate); isolating nuclei/cells of the set of nuclei and/or cells of the sample; and determining positions of nuclei/cells of the set of nuclei/cells upon sequencing molecules generated from the distribution of handshake sequences. Optionally, in some embodiments, methods can include tagging (e.g., microfluidic tagging, tagging within microwells, tagging within partitions, tagging within droplets of an emulsion) and tagging of nuclei targets (e.g., mRNAs, other nuclei targets) with handshake sequences, with characterization of spatial positions using the handshake sequences, after isolation of nuclei. Tagging can involve tagging using a membrane (e.g., nitrocellulose membrane, other membrane, etc.) from which handshake sequences can be released. Identification of nuclei targets can further optionally be performed using optical detection of nuclei targets tagged with probes during tagging and barcoding of nuclei, without sequencing.

In particular, the methods can include generating a spatial map of a distribution of nuclei of a tissue sample, upon releasing a set of handshake sequences paired with a set of barcode sequences for diffusion toward the distribution of nuclei. Generating the spatial map can be performed without use of a camera (e.g., by only using sample processing workflows, sequencing, and bioinformatics systems).

In embodiments, the disclosure also provides systems and methods for characterizing nuclei of a sample, where characterizing nuclei of a sample can include generating a set of labelled nuclei, upon tagging a set of nuclei with a first set of oligonucleotides (e.g., upon release of handshake sequences from a first substrate configured to interact with the sample); seating the set of labeled nuclei at interstitial spaces of a distribution of functionalized particles coupled to a second substrate, wherein each functionalized particle contacts no more than one labelled nucleus of the set of labelled nuclei; generating a single nucleus sequencing library from amplicons generated from a set of reactions involving the set of labelled nuclei and molecules of the distribution of functionalized particles; and returning a single nucleus analysis of the set of nuclei upon processing the single nucleus sequencing library.

In embodiments, the disclosure provides systems and methods for characterizing cells (e.g., single cells) of a sample, wherein characterizing cells of a sample can include: generating a set of labelled cells, upon tagging a set of cells with a first set of oligonucleotides (e.g., upon release of handshake sequences from a first substrate configured to interact with the sample); seating the set of labeled cells at interstitial spaces of a distribution of functionalized particles coupled to a second substrate, wherein each functionalized particle contacts no more than one labelled cell of the set of labelled cells; generating a single cell sequencing library from amplicons generated from a set of reactions involving the set of labelled cells and molecules of the distribution of functionalized particles; and returning a single cell analysis of the set of cells upon processing the single cell sequencing library.

In one embodiment for characterization of a set of single cells or single nuclei in three dimensions, the disclosure provides systems and methods, where a method can include: combining a set of functionalized particles with a set of single cells and/or a set of single nuclei, wherein a ratio of a number of functionalized particles to a number of single cells and/or single nuclei is greater than one (e.g., 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, etc.); retaining single cells and/or single nuclei within recesses (e.g., crevices, pores, other surface features, etc.) of the set of functionalized particles (e.g., where a single cell or single nucleus associates with no more than one functionalized particle of the set of functionalized particles); stabilizing the set of functionalized particles with associated single cells and/or single nuclei within a matrix (e.g., hydrogel matrix, other matrix), wherein the matrix can be transitioned between a set phase and a non-set phase, and wherein the matrix allows for diffusion of material below a first size threshold to and/or between the set of functionalized particles, and prevents material above a second size threshold from diffusion; lysing the set of single cells (if single cells are present) with a lysis buffer, with or without increasing a temperature of the lysis buffer, wherein the lysis buffer is introduced to the set of single cells through the matrix; performing a hybridization operation with content (e.g., mRNA content, other nucleic acid content, conjugated protein content, etc.) of the set of single cells and/or set of single nuclei with the set of functionalized particles, wherein content of a single cell or single nucleus can hybridize with more than one functionalized particle of the set of functionalized particles, wherein the hybridization operation tags target content of a single cell or single nucleus with one or more handshake sequences; transitioning the matrix from the set phase to the non-set phase, in coordination with performing a reverse transcription operation, a second strand synthesis operation, and a cDNA amplification operation after the hybridization operation; generating a sequencing library from amplicons generated from the cDNA amplification operation; and returning a single cell and/or single nucleus analysis of the set of cells/set of nuclei upon processing the sequencing library, wherein subsets of the set of functionalized particles associated with target material from a single cell/single nucleus are associated based upon a barcode (e.g., a barcode that can service as a spatial address, a cell barcode) having a nucleotide sequence (e.g., a stochastic sequence) associated with the single cell/single nucleus. When combined with spatial information (e.g., with use of barcodes that serve as spatial addresses described), the methods described can enable associations between genotypic features and phenotypic features of biological sample material.

The disclosure also provides embodiments of a substrate with functionalized particles, including a first subset of functionalized particles for tagging nuclei targets of a sample, and a second subset of functionalized particles for tagging cytoplasmic targets of the sample. In embodiments, a substrate can include functionalized particles for tagging only nuclei targets (e.g., nuclear RNA) of a sample. In embodiments, a substrate can include functionalized particles for tagging only cytoplasmic targets (e.g., cytoplasmic RNA) of a sample. In embodiments a substrate can be functionalized with functionalized particles to tag whole single cells of a sample. Additionally or alternatively, embodiments of the substrate can be configured to include multiple types of subsets of functionalized particles, where each respective subset is configured to tag a different type of sample target.

In relation to tissue processing, the disclosure provides methods, systems, and devices for spatially labeling targets (e.g., cytoplasmic targets) that are exposed during tissue processing (e.g., tissue slicing, tissue sectioning), as well as spatially labeling of individual nuclei and/or other intracellular components. Methods described can include determining locations of cell bodies (e.g., based upon nuclei positions) of a sample, and performing single-cell analysis techniques in coordination with spatial analysis of single-cell and other targets, where analysis techniques can include single nucleus RNA-seq (snRNA-seq), t-cell receptor (TCR) analyses, b-cell receptor (BCR) analyses (e.g., with receptor-ligand characterizations), ATAC-seq for assessment of chromatin accessibility, processing of nuclei and non-nuclei targets of formalin-fixed and paraffin-embedded (FFPE) samples, analysis of nuclear DNA, analysis of nuclear proteins, generation and analysis of single cell chromatin immunoprecipitation (ChIP) sequencing libraries; generation and analysis of single cell genome sequencing libraries, generation and analysis of single cell DNA-methylation sequencing libraries, generation and analysis of single cell Hi-C sequencing libraries, generation and analysis of single cell enzyme-tethering chromatin profiling sequencing libraries, generation and analysis of single cell genome and transcriptome sequencing libraries (G&T-seq), and other suitable analyses.

Methods can be performed at or below 4 degrees C., or other low temperatures.

Generally, embodiments of the methods, systems, and compositions provide mechanisms for efficient tagging and labeling of target material (e.g., DNA, RNA, miRNA, proteins, small molecules, single analytes, multianalytes, etc.) from single cells, single cells, and/or other biological material, in order to enable analyses for characterizing the biological material (e.g., with respect to locations of target analytes of the biological material in space, with respect to single cell analyses, with respect to single nuclei analyses, etc.).

For nucleic acid targets, tagging probes of compositions described can include complementary molecules to, the nucleic acid targets (e.g., based upon polyA/polyT interactions, based upon interactions between polyadenylated mRNAs and other nucleic acids incorporating U bases and/or T bases based upon complementarity to other sequences of nucleic acid targets). For protein targets or small molecule targets, tagging probes of the compositions described can include antibodies or aptamers conjugated with specific nucleic acid sequences for detection.

Targets can include cytoplasmic targets, intracellular targets, or other targets on the surface of or within a cell (or components of a cell). For instance, targets can include cytoplasmic targets and targets of or associated with nuclei of cells from the same tissue, such that simultaneous mapping of multiple target types in a highly parallel manner can be achieved. In one embodiment, spatial labeling of nuclei of a sample can include: processing a sample comprising a set of nuclei with a substrate comprising a distribution of functionalized molecules (e.g., with decoding of positions of the functionalized molecules by way of barcode sequences that can serve as spatial addresses, as described below); tagging the set of nuclei with handshake sequences comprising the barcode sequences that can serve as spatial addresses (e.g., upon releasing functionalized molecules from the functionalized particles); isolating nuclei of the set of nuclei and/or other targets of the sample; and determining positions of nuclei of the set of nuclei upon sequencing molecules generated from the distribution of functionalized molecules. Optionally, in some embodiments, methods can include tagging (e.g., microfluidics-based tagging, tagging within microwells, tagging within partitions, tagging within droplets of an emulsion) and barcoding of nuclei targets (e.g., mRNAs, other nuclei targets) with handshake sequences comprising barcodes that can serve as spatial addresses. Identification of nuclei targets can further optionally be performed using optical detection of nuclei targets tagged with probes during tagging of nuclei, without sequencing.

In relation to tissue processing, the disclosure provides methods, systems, and devices for spatially labeling targets (e.g., cytoplasmic targets) that are exposed during tissue processing (e.g., tissue slicing, tissue sectioning), as well as spatially labeling of individual nuclei and/or other intracellular components. Methods described can include determining locations of cell bodies (e.g., based upon nuclei positions) of a sample, and performing single-cell analysis techniques in coordination with spatial analysis of single-cell and other targets, where analysis techniques can include single nucleus RNA-seq (snRNA-seq), t-cell receptor (TCR) analyses, b-cell receptor (BCR) analyses (e.g., with receptor-ligand characterizations), ATAC-seq for assessment of chromatin accessibility, processing of nuclei and non-nuclei targets of formalin-fixed and paraffin-embedded (FFPE) samples, analysis of nuclear DNA, analysis of nuclear proteins, generation and analysis of single cell chromatin immunoprecipitation (ChIP) sequencing libraries; generation and analysis of single cell genome sequencing libraries, generation and analysis of single cell DNA-methylation sequencing libraries, generation and analysis of single cell Hi-C sequencing libraries, generation and analysis of single cell enzyme-tethering chromatin profiling sequencing libraries, generation and analysis of single cell genome and transcriptome sequencing libraries (G&T-seq), and other suitable analyses.

The systems, methods, and devices disclosed herein can provide several additional benefits over other systems and methods, and such systems, methods, and devices are further implemented into many practical applications across various disciplines.

The systems, methods, and devices described address limitations that currently plague performance of single nuclei and/or single cell analyses, with respect to isolation of nuclei and cells, rapid partitioning of nuclei and cells (with the ability to process material of a single cell or nucleus that has interacted with multiple functionalized particles), performance of spatial transcriptomics analyses, and other limitations of current state-of-the art methods.

The systems, methods, and devices solve cell segmentation issues and sensitivity issues associated with mapping cell-associated targets (e.g., cytoplasmic targets, nuclei-associated targets, etc.). The systems, methods, and devices solve cell segmentation issues and sensitivity issues associated with mapping of targets in human tissue.

The systems, methods, and devices further improve accuracy of spatial mapping of nuclei targets. In embodiments where a nucleus is tagged using releasable molecules of functionalized particles, tagging of the nucleus can involve tagging the nucleus with different releasable molecules associated with different spatial positions. As such, determining the position of the nucleus can involve determining the position based upon a subset of positions corresponding to a subset of stochastic barcodes of molecules that tagged the nucleus. The position of the nucleus can be determined from an average position of the subset of stochastic barcodes (e.g., a centroid of positions of the subset of stochastic barcodes). In variations, nuclei can be tagged using a combination of cleavable and non-cleavable molecules, such that positions of the nuclei can be determined from stochastic/spatial barcode positions of cleavable and non-cleavable molecules (e.g., as a weighted centroid of positions, where positions of non-cleavable components are weighted more heavily than positions of cleavable components). As such, the position estimated from the barcodes serving as spatial addresses can be an estimation of the location in or on a sample, in or on a feature (e.g., functionalized particle) or a combination thereof.

In relation to tagging nuclei targets with handshake sequences comprising barcodes that can service as spatial addresses, and mapping of nuclei targets that have been tagged with handshake sequences, the systems, methods, and compositions described can generate spatial maps with improved recovery rate for nuclei targets (e.g., in relation to actual numbers of nuclei targets present) to greater than 15%, greater than 20%, greater than 25%, greater than 30%, greater than 35%, greater than 40%, greater than 45%, greater than 50%, greater than 60% or greater In examples, the disclosure provides embodiments, variations, and examples of systems, methods, and compositions for generating spatial maps with improved recovery rate for nuclei targets (e.g., in relation to actual numbers of nuclei targets present), where the number of nuclei recovered from a tissue section (e.g., embryonic tissue section, other tissue section) can be greater than 50,000, greater than 60,000, greater than 70,000, greater than 80,000, greater than 90,000, greater than 100,000, greater than 110,000, greater than 120,000, greater than 130,000, greater than 140,000, greater than 150,000, greater than 160,000, greater than 170,000, greater than 180,000, greater than 190,000, greater than 200,000, greater than 250,000, or greater (e.g., for a tissue section from 5 microns through 40 microns thick, and with a surface area greater than 3 mm×3 mm, greater than 10 mm×10 mm, or of another suitable dimension). Recovery of nuclei can be determined upon dissociation of the sample and counting of nuclei (e.g., through a cytometry-based method). Alternatively, recovery of nuclei can be determined upon performing sequencing of nuclei. Alternatively, recovery of nuclei can be determined upon spatially positioning nuclei during mapping (e.g., after sequencing of nuclei and corresponding barcode sequences that serve as spatial addresses). In particular, nuclei retention is typically poor due to losses during sample processing and isolation of nuclei, and the disclosure provides methods for improved recovery rate and retention of nuclei. The recovery rate can be determined as a percentage of nuclei originally present in the sample.

In relation to tagging of nuclei and/or other targets of a sample with functionalized molecules of functionalized particles, functionalized molecules can include unique molecular identifiers (UMIS). The disclosure provides embodiments, variations, and examples of systems, methods, and compositions for recovering greater than 2000 UMIs per nucleus/target, greater than 2500 UMIs per nucleus/target, greater than 3000 UMIs per nucleus/target, greater than 3500 UMIs per nucleus/target, greater than 4000 UMIs per nucleus/target, greater than 4500 UMIs per nucleus/target, greater than 5000 UMIs per nucleus/target, greater than 5500 UMIs per nucleus/target, greater than 6000 UMIs per nucleus/target, greater than 6500 UMIs per nucleus/target, greater than 7000 UMIs per nucleus/target, greater than 7500 UMIs per nucleus/target, greater than 8000 UMIs per nucleus/target, greater than 8500 UMIs per nucleus/target, greater than 9000 UMIs per nucleus/target, greater than 9500 UMIs per nucleus/target, greater than 10,000 UMIs per nucleus/target, greater than 20,00 UMIs per nucleus/target, or greater. As such, systems, methods, and devices described can achieve higher UMI tags per nucleus/target, in relation to existing single-cell techniques and other state-of-the-art techniques.

The systems, methods, and devices can generate spatial maps of a set of targets of a sample, where the spatial maps have unprecedented resolution performance, ability to map multiple sets of targets for different sample and tissue types, and satisfy quality metrics for high resolution mapping.

The systems, methods, and devices also are designed to promote ease of use by end user(s), in relation to processing different tissue types and/or various sample types (e.g., involving natural and synthetic scaffolds).

The systems, methods, and devices provide and implement non-naturally occurring compositions for facilitating tagging of target biological material from a sample and characterizing locations of target biological material in space (e.g., two dimensional space, three dimensional space). Such compositions can include materials that have been modified from their natural states (e.g., in terms of providing structural differences from natural compositions). Furthermore, the invention(s) relate to combinations of materials, where the combinations of materials are non-naturally occurring (e.g., there is no naturally occurring counterpart to the compositions described and claimed).

The systems, methods, and devices provide improved manufacturing methods for generating systems for characterizing locations of target analytes in space.

The systems, methods, and devices provide improved characterization of locations of targets in multidimensions (e.g., 2D, 3D, 4D with a time component), in relation to one or more of: whole tissue structures, tissue pieces (e.g., as in histology, in relation to biopsied tissues, in relation to seeded natural scaffolds, in relation to seeded synthetic scaffolds (e.g., cell-seeded hydrogel scaffolds, cell-seeded polaxamer scaffolds, etc.) in relation to frozen tissue specimens, in relation to formalin-fixed paraffin-embedded (FFPE) specimens, etc.), organs, whole organisms, cell suspensions, single cells, organelles, within organelles, in relation to mitochondrial targets, viruses, microorganisms, and other natural structures. Cells can include mammalian cells, bacteria, microbes, plant cells, fungal cells, or other cells/cell-like components. Location characterization can additionally or alternatively be performed in relation to non-naturally occurring structures, such as microwells, microarrays, scaffolds, and other non-naturally occurring structures. For instance, the invention(s) can have in situ and/or in vivo applications, with infusion of functionalized particles into a sample (e.g., into a cell, into a tissue, into an organ, etc.). Examples of infusion can include one or more of: injection, electroporation, use of vectors (e.g., viral vectors), and other infusion methods.

In relation to location characterization in multiple dimensions, particles of the composition(s) described can be implemented in monolayer form (e.g., with manufacturing processes to apply composition units in monolayer or near-monolayer form, with systems that apply magnetic or other forces to form particle monolayers, etc.), with sample (e.g., tissue, cells) positioned adjacent the monolayer for subsequent processing and mapping. Alternatively, particles of the composition(s) described can be infused into a sample/specimen (e.g., by magnetic force, by electroporation, by using vectors, etc.). Alternatively, particles of the composition(s) described can be coupled to a surface of a sample/specimen (e.g., by chemical binding, by magnetic binding, by other binding), in order to enable surface mapping. Alternatively, particles of the composition(s) described can be guided or otherwise retained in 3D structures (e.g., in grids, in non-grid structures), such as microwells, microarrays (e.g., with nucleic acids capturing particles), matrices (e.g., hydrogels, scaffolds), or other 3D structures. In a related application, physical or other forces can be used to define structures (e.g., close packed structures) for distributions of particles that interact with samples to enable mapping. Alternatively, in relation to location characterization in multiple dimensions, particles of composition(s) described can be randomly distributed in space.

The systems, methods, and devices provide improved applications in spatial transcriptomics. For instance, compositions, methods, and systems described can be used for mapping of targets in a sample over time, in order to understand disease pathology and progression (e.g., spread of targets and changes in expression over time).

Additionally or alternatively, the systems, devices, or methods described can confer any other suitable benefit.

2. SYSTEMS

As shown in FIG. 1A, an embodiment of a system 100 for characterizing positions of targets of a sample can include: a substrate 110; and a distribution of functionalized features 120 associated with the substrate 110, wherein a representative feature 130 of the distribution of functionalized features includes: one or more functionalized molecules 140 coupled to the representative feature 130, the one or more molecules 140 including at least: a handshake sequence 141 comprising a reactive portion, a barcode segment 142, where the barcode segment 142 can serve as a spatial address, and a cleavable linker 143 configured to allow the handshake sequence 141 to be released from the representative feature 130 (e.g., in response to a stimulus). Variations of the system 100 can optionally include a masking layer 150 (e.g., sticker) that functions to protect functionalized features from prematurely being exposed to stimuli or otherwise damaged in a manner that prevents the handshake sequences from being controllably released from the distribution of functionalized features 120 for tagging targets of a sample.

Figure 1B:
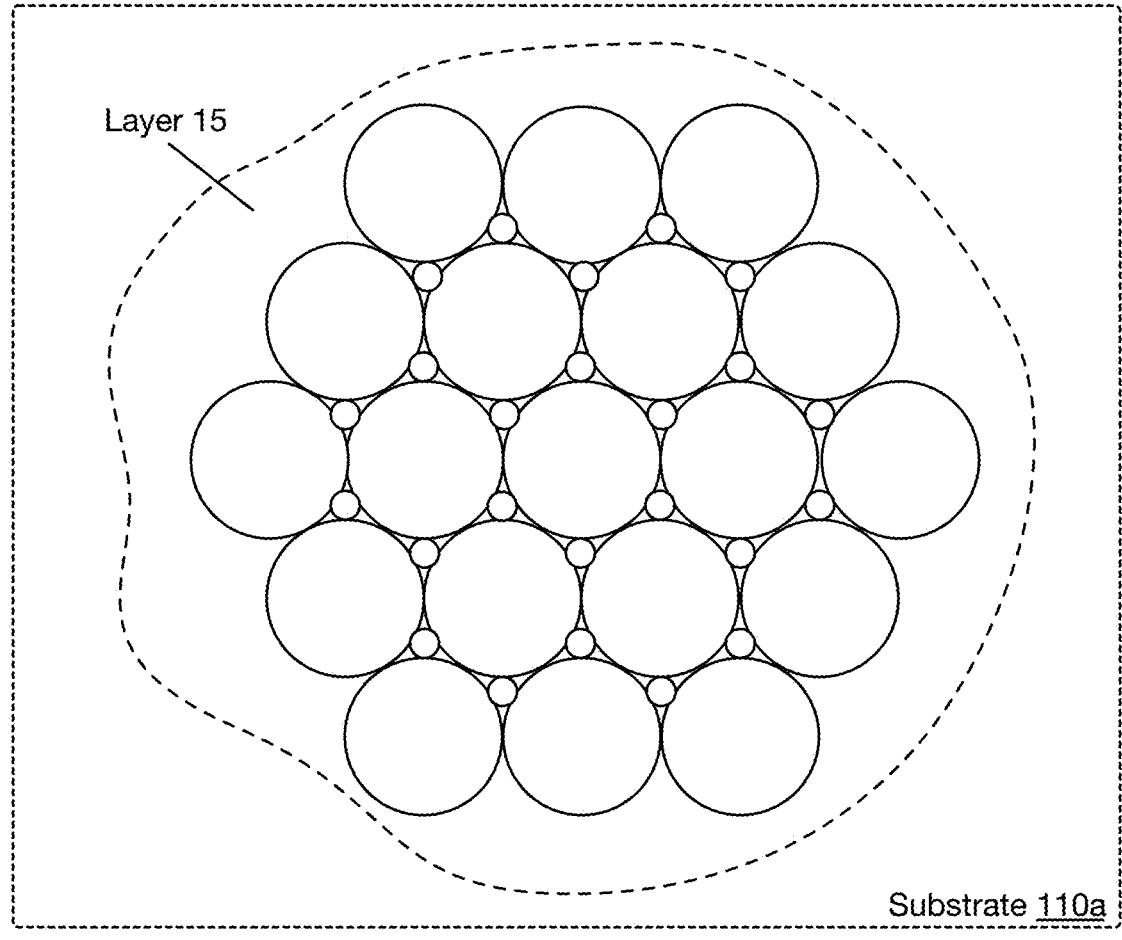
FIG. 1B depicts a schematic of an embodiment of a system for partitioning single cells that have been tagged with handshake sequences.

In a variation, as shown in FIG. 1B, a system for performing single cell analyses can include: a substrate 110a; a distribution of functionalized particles 120a coupled to the substrate 110a (e.g., with an adhesive); and a set of cells 10 positioned at interstitial spaces of the distribution of functionalized particles.

In a variation, as shown in FIG. 1C, a system for performing single nuclei analyses can include: a substrate 110b; a distribution of functionalized particles 120b coupled to the substrate 110b (e.g., with an adhesive); and a set of nuclei 15 positioned at interstitial spaces of the distribution of functionalized particles.

Embodiments, variations, and examples of the system 100 function to interact with, spatially define, and label target analytes of a sample upon release of handshake sequences structured to interact with target analyes of the sample, in order to enable characterization of such target analytes of the sample (e.g., with respect to spatial analyses, with respect other analyses, such as single cell or single nuclei analyses). Embodiments, variations, and examples of the system 100 can also spatially separate and isolate sample particles (e.g., single cells, nuclei, molecules, other analytes or particles, etc.) at spaces between features of the system.

In embodiments, the target analytes can include one or more of: nucleic acid material (e.g., DNA, RNA, miRNA, etc.), protein material, amino acid material, other small molecules, other single analytes, other multi-analytes, and/or other suitable target material of a sample. In embodiments, the sample can include whole tissue structures, tissue portions (e.g., histological tissue slices, formalin-fixed paraffin-embedded (FFPE) tissue, frozen tissue (e.g., fresh frozen tissue), fixed tissue, permeabilized tissue, biopsied tissues, fresh frozen plasma, seeded natural scaffolds, seeded synthetic scaffolds, etc.), organs, whole organisms, organoids, a cell suspension (e.g., frozen cell suspensions that are separated prior to processing with the system, cell suspensions retained in a medium/hydrogel medium, etc.), single cells, a nuclei suspension, organelles, sub-organelle structures, intra-organelle components, mitochondrial targets, viruses, microorganisms, and other samples. In variations, methods described herein involve tagging targets of a sample using spatial sequences distributed across a plurality of substrates, wherein the sample is not fixed and is not permeabilized prior to tagging targets of the sample. As such, methods described herein can omit fixation, permeabilization, and/or de-crosslinking of samples in relation to generating spatial analyses of targets of the samples.

In some non-limiting examples, sample material from which targets can be tagged with handshake sequences can include one or more of: nervous system biological material, cardiovascular system biological material, integumentary system biological material, skeletal system biological material, muscular system biological material, respiratory system biological material, digestive system biological material, endocrine system biological material, urinary system biological material, and reproductive system biological material. Cellular material can be associated with normal and diseased states, including one or more of: cancer cells, circulating tumor cells, metastatic cells, benign cells, or any combination thereof. In embodiments, the sample can include solid/contiguous tissue material obtained from a subject.

Details of the system 100 and use thereof are described in further detail in the following sections.

2.1 System—Substrate

The substrate 110 functions to provide one or more surfaces onto which the distribution of functionalized features 120 is patterned or otherwise deposited (as described below). The substrate 110 thus functions to support the distribution of functionalized features 120 in a reliable manner during sample handling and processing. The substrate 110 can additionally or alternatively function to support mechanisms for controlled interactions with the distribution of functionalized particles (e.g., with respect to controllable binding and release mechanisms, etc.). The substrate 110 can additionally or alternatively function to facilitate detection of optical signals generated from interactions between the distribution of functionalized particles 120 and tagged target analytes of the sample, by having suitable optical characteristics for transmission of light signals to an optical signal sensing apparatus. The substrate 110 can additionally or alternatively function to enable transmission of heat to a sample interacting with the system 100 during use, in order to promote interactions between the target analytes and the distribution of functionalized features 120 at the substrate 110. Additionally or alternatively, the substrate 110 can have other suitable functionality.

In one embodiment, the substrate 110 is composed of glass/silica (e.g., a borosilicate glass), which offers desired properties for manufacturing (e.g., in relation to surface functionalization, in relation to processing, in relation to separation of composition units, etc.), thermal characteristics (e.g., in terms of thermal conductivity, electrical characteristics (e.g., in terms of supporting charge, in terms of electrical conductivity, etc.), optical characteristics (e.g., providing mechanisms for optical recognition, characterized by one or more optical features encoding a set of nucleic acid bases, the set of nucleic acid bases identifiable upon detection of the one or more optical features, etc.), magnetic properties (e.g., in relation to providing or supporting magnetic fields for manipulation of sample components and/or aspects of the distribution of functionalized features 120), biocompatibility characteristics, and/or other suitable characteristics. Alternatively, the substrate 110 can include, or be composed of one or more of: plastic/polymer materials (e.g., acrylic, cyclic olefin polymer, polycarbonate, poly(methyl methacrylate) (PMMA), cyclo olefin polymer (COP), polystyrene, polypropylene, polyethylene terephthalate glycol-modified (PEGT), etc.); ternary compositions (e.g., indium tin oxide); and/or other suitable materials.

In variations, the substrate 110 has a characteristic roughness less than or equal to 1 micrometer (e.g., 0.8 micrometer), but can alternatively have another suitable roughness. For instance, variations of the substrate 110 can have a desired roughness (e.g., greater than 1 micrometer) to provide a desired texture or serve other suitable functionality.

The substrate 110 can have a thickness from 0.5 millimeters to 3 millimeters.

Additionally or alternatively, the substrate 110 can be flexible (e.g., composed of a flexible material) in order to enable applications involving flexible application to a sample surface (e.g., wrapping around a tissue body, etc.).

Figure 1D:
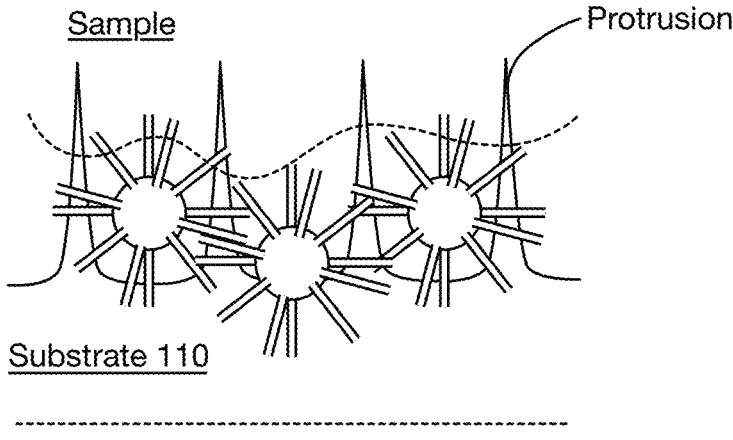
FIG. 1D depicts first variations of structural features for characterizing locations of targets in space, using releasable handshake sequences.

In some variations, as shown in FIG. 1D, the substrate 110 (and/or functionalized particle surfaces) can include a set of protrusions establishing an interface between the sample and the distribution of functionalized particles during use. As such, during operation, protrusions of the substrate 110 can be configured to extend into the sample (e.g., into tissue) to promote desired interactions between deeper portions of the sample and the distribution of functionalized particles at the substrate 110. In a related variation, the protrusions can be hollow (e.g., as in microneedles), to aid transmission of fluid material to the sample (e.g., for sample processing) and/or to promote target analyte tagging with handshake sequences.

Figure 1E:
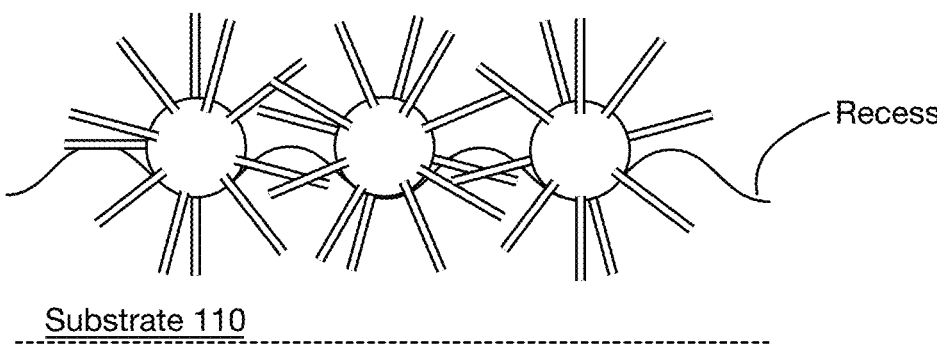
FIG. 1E depicts second variations of structural features for characterizing locations of targets in space, using releasable handshake sequences.

Additionally or alternatively, as shown in FIG. 1E, the substrate 110 can include a set of recesses configured to receive or otherwise support the distribution of functionalized particles 120, for instance, for positioning of the distribution of functionalized particles 120 at the substrate 110 in a desired configuration (e.g., patterned manner, with desired density, in a monodisperse manner, in monolayer, etc.).

Additionally or alternatively, the substrate 110 can include or be positioned adjacent to a set of fiducials, where the set of fiducials can provide observable markings for manufacturing (e.g., in relation to scribing/sawing of the substrate to separate units). Additionally or alternatively, the set of fiducials can define addressable locations of the system 100/distribution of functionalized particles for characterizing locations of target analytes of the sample tagged using the system 100.

Additionally or alternatively, the substrate 110 can be optically recognizable (e.g., such that the substrate can be observed with optical apparatus to provide a signal). In variations, the substrate can be characterized by one or more optical features encoding a set of nucleic acid bases, the set of nucleic acid bases identifiable upon detection of the one or more optical features.

2.2 System—Functionalized Features

As shown in FIG. 1A, the system 100 further includes a distribution of functionalized features 120 associated with the substrate 110, in order to enable analyses for characterizing locations of target material in space. In variations, the distribution of functionalized features 120 can comprise functionalized particles (e.g., 120a, 120b in FIGS. 1B and 1C) that can also function to provide interstitial spaces for receiving particles (e.g., nuclei, single cells, cell clusters, sample particles, etc.) of a sample, in order to enable tagging of such particles for further analyses. The distribution of functionalized features 120 can thus function to retain in position particles from the sample, and to provide functionality for decoding aspects of the target analytes and/or locations of target analytes of the sample particles in space, upon sequencing.

A representative functionalized feature 130 can include one or more functionalized molecules 140 coupled to the representative feature 130, the one or more molecules 140 including at least: a handshake sequence 141 comprising a reactive portion, a barcode segment 142, where the barcode segment 142 can serve as a spatial address, and a cleavable linker 143 configured to allow the handshake sequence 141 to be released from the representative feature 130 (e.g., in response to a stimulus).

In embodiments, the distribution of functionalized features 120 can include one or more of: a distribution of particles, a distribution of wells, a distribution of protruding features, a distribution of recessed features, a distribution of pegs, a distribution of etched features, a distribution of printed features, a distribution of spots, a distribution of microspheres, a distribution of capillaries, and/or other forms of features. Feature(s) of the distribution of features may take the form of resins, metals, polymers, ceramics, or other forms or materials.

In embodiments, the distribution of functionalized features 120 is arranged at the substrate 110 (e.g., using a templating process, using another suitable process) with a polygonal footprint; however, in other variations the distribution of functionalized features 120 can be arranged with other suitable morphology (e.g., a circular footprint, an ellipsoidal footprint, a rectangular footprint, a polygonal footprint, an amorphous footprint, etc.). In one such example, the distribution of functionalized features 120 is arranged with a square footprint having a corner notch for orientation purposes. In still other variations, the distribution of functionalized features 120 can be patterned onto the substrate 110 in an arrangement corresponding to the sample(s) being processed using the system 100. For instance, in some variations, the distribution of functionalized features 120 can be patterned in a manner corresponding to a characteristic sample shape (e.g., tissue biopsy shape), characteristic sample structural features (e.g., tissue fiber orientations), characteristic sample container shape (e.g., tube shape, well shape, etc.), and/or other suitable feature.

In variations, a characteristic dimension (e.g., diameter, width, length, etc.) of the arrangement in bulk of the distribution of functionalized features 120 can range from 1 to 10 mm (or alternatively, greater than 10 mm, in order to enable handling of larger sample sizes), and in specific examples, the characteristic dimension of the distribution of functionalized features 120 can range from 2 to 4 mm (e.g., width or length of a polygonal footprint).

In variations, a distribution of functionalized features 120 comprising a distribution of functionalized particles can have a length or width of 1 millimeter, a length or width of 2 millimeters, a length or width of 3 millimeters, a length or width of 4 millimeters, a length or width of 5 millimeters, a length or width of 6 millimeters, a length or width of 7 millimeters, a length or width of 8 millimeters, a length or width of 9 millimeters, a length or width of 10 millimeters, a length or width of 11 millimeters, a length or width of 12 millimeters, a length or width of 13 millimeters, a length or width of 14 millimeters, a length or width of 15 millimeters, a length or width of 16 millimeters, a length or width of 17 millimeters, a length or width of 18 millimeters, a length or width of 19 millimeters, a length or width of 20 millimeters, an intermediate length or width, or another suitable length or width (e.g., greater than 20 millimeters).

In one example, a distribution of functionalized features having a footprint of 3 mm×3 mm can be used for simultaneous tagging of nuclei targets and other targets (e.g., cytoplasmic targets). In another example, a distribution of functionalized features having a footprint of 10 mm×10 mm can be used for simultaneous tagging of nuclei targets and other targets (e.g., cytoplasmic targets).

Features can be provided on the substrate 110 as a grid of spots or patches. The features can be distributed in a repeating pattern or in an irregular, non-repeating pattern. Optionally, repeating patterns can include hexagonal patterns, rectilinear patterns, grid patterns, patterns having reflective symmetry, patterns having rotational symmetry, or the like. Asymmetric patterns can also be implemented. The pitch of an array can be the same between different pairs of nearest neighbor features or the pitch can vary between different pairs of nearest neighbor features. A substrate 110 can have multiple distributions of functionalized features arranged as separate arrays, where the separate arrays can be individually manipulated, separated, or otherwise processed.

In examples, larger substrates can be used to accommodate larger tissue samples, in order to generate spatial maps of larger tissue samples. However, the distribution of functionalized features 120 can alternatively have another suitable characteristic dimension.

Furthermore, a substrate 110 can have more than one distribution of functionalized features 120, as shown in FIG. 1F, where different distributions (e.g., 20a through 20i shown in FIG. 1F) can be arranged in an array or otherwise arranged. In variations, the different distributions can be arranged in a 2×2 array, a 3×3 array, or any other suitable array (ordered or non-ordered) on a substrate 110. Arrays of distributions of features can be used to accommodate larger tissue samples, in order to generate spatial maps of larger tissue samples. As such, methods using arrayed distributions can include applying a sample (e.g., tissue sample), to an array of distributions of functionalized particles, and processing the sample according to embodiments, variations, and examples of method steps described.

Furthermore, one or more distributions of functionalized particles at a substrate 110 can include differences in barcode sequences (e.g., each subunit of the array can have a different barcode sequence associated with a particular subunit), which can be used for selective amplification and sequencing of different regions of a sample applied to the array. In one example, a region of interest associated with a first subunit of the array can be selectively amplified and sequenced using the unique barcode sequence of the unit. If results from the region of interest are promising or otherwise satisfy a condition (e.g., quality condition related to determination of UMI read characteristics, quality condition related to determination of barcode read characteristics) that warrants additional investigation, then the method can include selective amplification and sequencing of other regions of the sample, using the unique barcode sequences of the other units.

In more detail, implementation of multiple distributions of functionalized particles (e.g., different sub-arrays each having the same or different footprints) can enable regional subsampling (e.g. selective amplification, interrogation, and/or detection of targets at a specific sub-array). Different sub-arrays can be configured to tag different target types (e.g., a first sub-array can be configured to tag a first target type with first handshake sequences, and a second sub-array can be configured to tag a second target type with second handshake sequences). Alternatively, different sub-arrays can each be configured to tag multiple target types (e.g., a first sub-array can be configured to tag multiple target types with respective handshake sequences).

Selective amplification can be enabled by implementation of functional molecules for tagging different target types, where molecules can have different PCR handles corresponding to different target types intended to be tagged (as described in relation to functional molecules described in further detail below).

The distribution of functionalized features 120 is preferably arranged at the substrate 110 with a high degree of density (e.g., random close packing, hexagonal close packing, rectangular close packing, near-close packing, etc.). In specific examples, the distribution of functionalized features 120 is characterized by a high level of packing density at the surface of the substrate 110. In relation to close packing of particles (e.g., random close packing), the packing density at the substrate can be from 55% to 74%, such that the empty or dead space between particles is from 26% to 45%. As such, the configuration of the distribution of functionalized features 120 achieves minimal dead space, as permitted by physics. Additionally or alternatively, in relation to implementation of functionalized particles having different subpopulations of body sizes, interstitial spaces or other gaps between particles of a first size can be covered with particles of a second size, in order to further increase density of packing and thus, resolution of maps generated (e.g., as in FIG. 1G) or the ability to simultaneously tag targets from different sources (e.g., cytoplasmic targets, nuclei targets, protein targets, other targets). Still alternatively, gaps or other interstitial spaces between functionalized features (e.g. particles) can be configured (e.g., sized) to receive sample components (e.g., single cells, single nuclei, clusters, etc.) for single component or cluster retention and processing, as described herein. In embodiments where the distribution of functionalized features 120 includes particle configurations for retention of individual cells, nuclei, clusters, or other particles, a configuration of the system 100 can further include a layer 15 (described in further detail below), where the layer 15 can promote retention of individual cells, nuclei, clusters, or other particles that are positioned at gaps or other interstitial spaces between functionalized particles. The layer 15 can also support reliable diffusion of process reagents to sample components of interest retained at the substrate 110 during a stage of sample processing.

The distribution of functionalized features 120 can, however, be characterized by another suitable percent packing density at the surface of the substrate. The distribution is preferably also monodisperse (e.g., uniformly distributed and with particles/features of substantially uniform size, with a critical distance between particles/features below a threshold); however, the distribution can alternatively be non-monodisperse/random. As such, the distribution of functionalized features can be random or governed by morphology of the substrate (e.g., with meshes, with wells, with protrusions, with recesses, with textures, etc.).

Furthermore, the distribution of functionalized features 120 is preferably arranged at the substrate 110 in a monolayer (e.g., without stacking); however, in variations, the distribution of functionalized features 120 can be arranged at the substrate 110 with a different degree of density (e.g., non-packed) and/or in non-monolayer format. In one such variation, the distribution of functionalized features can be arranged in one or more sub-arrays (e.g., patterned for a specific application of use). In examples, the sub-arrays can include a different sub-arrays functionalized for different target analytes, different forms of target analytes (e.g., such as for different epitopes), control regions, or other suitable regions. Additionally or alternatively, multiple distributions can be arranged at a single substrate (e.g., an array or matrix of distributions of functionalized features, arranged in discrete zones at the substrate).

In variations, a distribution of functionalized features 120 comprising a distribution of functionalized particles can be coupled to the substrate 110 using an adhesive layer 112 to which particles can adhere (e.g., in a reversible manner, in a permanent manner). In variations, the distribution of functionalized particles can be coupled to the substrate 110 by way of the adhesive layer 112 (shown in FIG. 1A) in a coupled operation mode, and separated from the substrate 110 in a separated operation mode. The adhesion or pull-off force for separation can range from 200 to 500 nano-Newtons; however, in other variations, the adhesion or pull-off force can be less than 200 nano-Newtons or greater than 500 nano-Newtons. Preferably, the distribution of functionalized particles 120 remains reliably coupled to the substrate when interfaced with the sample and during sample processing operations (e.g., hybridization, 2nd strand synthesis, etc.).

In variations, separation can be achieved using a detergent that separates the distribution of functionalized features 120 from the adhesive layer 112 and/or substrate 110 directly. As such, by coupling of the distribution of functionalized particles can be provided by at least one of a hydrophobic interaction and a hydrophilic interaction that is reversible by addition of a detergent separation. Additionally or alternatively, separation can be achieved with linkers (e.g., cleavable linkers) coupling the functionalized particles to the layer or substrate (e.g., by a chemical modification at the substrate), where the linkers are configured to be cleaved in response to one or more of: a thermal cleavage mechanism, a pH shift, a photocleaving mechanism, a chemical cleaving mechanism, an enzymatic cleaving mechanism (e.g., as in molecular scissors), separation based upon changes in charge (e.g., as in an electrostatic interaction), or another suitable cleaving/separation mechanism.

The adhesive layer 112 can provide an adhesive strength having a threshold force level (e.g., 100 nano-Newtons, 200 nano-Newtons, greater than 200 nano-Newtons, etc.) for detachment of functionalized particles. In variations, the adhesive layer 112 can reliably retain functionalized particles in position during a first set of steps of a process, and reliably allow release of all (or a desired portion) of functionalized particles in coordination with performing a second set of steps of a process. For instance, in an example, the adhesive layer 112 can reliably retain functionalized particles in position at a substrate (e.g., glass slide) during steps involving application of a sample (e.g., tissue sample) to be positioned adjacent to functionalized particles, and release of handshake sequences of from functionalized particles for tagging of sample targets.

The adhesive layer 112 can additionally or alternatively allow detachment of functionalized particles during sample clearing (e.g., dissolution of tissue samples) and/or release and resuspension of functionalized particles for further processing of tagged target material. Detachment of particles can be performed with use of a detergent or other processing to facilitate particle release from the adhesive layer 112. Alternatively, the adhesive layer 112 can be configured to be removed from the substrate 110 with the functionalized particles still attached.

The adhesive layer 112 can have a surface roughness less than 1 micrometer, less than 0.9 micrometers, less than 0.8 micrometers, less than 0.7 micrometers, less than 0.6 micrometers, less than 0.5 micrometers, less than 0.4 micrometers, less than 0.3 micrometers, less than 0.2 micrometers, less than 0.1 micrometers, less than 0.05 micrometers, less than 0.01 micrometers, or lower. Low surface roughness values can promote distribution uniformity of functionalized particles at the substrate (e.g., in relation to the level of close packing achieved). Low surface roughness values can also provide higher levels of clarity/transparency, which can allow for optical detection of signals through a surface of the substrate 110 that is opposite to a surface of the substrate 110 to which functionalized particles are coupled, and/or optical detection of signals through a surface of the substrate 110 that on the same side as a surface of the substrate 110 to which functionalized particles are coupled (e.g., for sample analysis, for optical focusing, etc.).

The adhesive layer 112 can be electrostatic (e.g., positively charged), to support biological sample adhesion.

The adhesive layer 112 can provide a level of hydrophobicity above a threshold, and in variations, the layer 112 can provide a contact angle greater than 10 degrees, greater than 15 degrees, greater than 20 degrees, greater than 25 degrees, greater than 30 degrees, greater than 35 degrees, greater than 40 degrees, greater than 45 degrees, greater than 50 degrees, greater than 55 degrees, greater than 60 degrees, greater than 70 degrees, greater than 80 degrees, greater than 90 degrees, or greater.

The adhesive layer 112 can be composed of a rubber (e.g., thermoplastic rubber) and/or other suitable polymer, and in specific examples, includes one or more of: an isoprene-based material, a styrene-based material, a propylene-based material, an ethylene-based material, a nylon-based material, and other suitable rubber/polymer materials. However, in other variations, the layer 112 can alternatively be composed of another suitable material.

In examples, the adhesive layer 112 can include one or more of: liquid electrical tape, latex, rubbers, elastomers, acrylate polymers, cyanoacrylate, gels, rubberized sealant, silicone conformal coatings, other conformal coatings, or other materials.

The adhesive layer 112 can support fabrication processes (e.g., using a spraying process, using a vapor deposition process, using a spin-coating process, using a printing process, etc.) and coupling of the distribution of functionalized particles to the layer. The layer 112 can further be composed of a thermoplastic material, or can alternatively be composed of a thermosetting material. The adhesive layer 112 can be processed in liquid form (e.g., with suitable solvents) and applied to the substrate 110 using one or more processes (described in further detail below); however, the adhesive layer 112 can additionally or alternatively be applied to the substrate 110 in another suitable manner (e.g., as a pre-generated film, using a printing process, using a patterning process, etc.). For instance, in some examples, the adhesive layer 112 can be applied to the substrate 110 with a pattern or texture that promotes preferential coupling of the distribution of functionalized particles 120 to the adhesive layer 112 with a desired pattern and/or density (e.g., by using hydrophobic characteristics, hydrophilic characteristics, chemical bond characteristics, etc.).

Additionally or alternatively, adherence can be supported and/or reversed using magnetic forces. For instance, as described above, functionalized particles can have or be composed of magnetic materials, and manipulated (e.g., retained in position or separated from a substrate) by application, reversal, and/or removal of magnetic forces.

In relation to manufacturing processes described in further detail below, multiple distributions of functionalized particles can be arranged at a bulk substrate, and separated from each other to create units of the system 100. Additional details of manufacturing are described in more detail below.

Furthermore, during use, and in an application of use involving spatial characterization of target analytes in 3D, stacks of substrates with distributions of functionalized particles can be implemented (e.g., with layering of samples/slices of tissue and units of the system 100). As such, the system 100 can include additional substrates with distributions of functionalized particles (e.g., a second substrate with a second distribution of functionalized particles, a third substrate with a third distribution of functionalized particles, etc.), with layering of sample and reconstruction of 3D volumes by stitching data derived from implementation of the various substrates.

Embodiments, variations, and examples of the distribution of functionalized features can additionally or alternatively include compositions described in U.S. application Ser. No. 17/376,396 filed on 15 Jul. 2021, which is herein incorporated in its entirety by this reference. Such functionalized features for determining nearest neighbor interactions can thus be provided with substrates or other natural/synthetic structures in order to characterize locations of target analytes in space.

2.2.1 Particles

In embodiments where the distribution of functionalized features 120 comprises functionalized particles, a representative functionalized particle can have a body 30. The body 30 functions to provide a surface to which the one or more molecules 140 can be coupled, in order to provide functionalization for sample target tagging (e.g., from tissues, from cells, from nuclei, from other biological sample components) upon release of a handshake sequence from the body 30, sample processing, and/or subsequent location characterization operations.

In relation to morphology, the body 30 can have the form of a microsphere. Alternatively, the body 30 can have the form of a non-spherical (e.g., ellipsoidal, prismatic, polyhedral, amorphous, nanotube, etc.) body, where a cross section taken through the body 30 is non-circular. However, the body 30 can alternatively have another suitable form. For instance, in variations, the bodies 30 can be quantum dots responsive to excitation by different types of energy (e.g., wavelength ranges of electromagnetic energy for various applications.

The body 30 can alternatively include features (e.g., surface features, internal features) that support tagging or retention of sample components (e.g., single nuclei, single cells, etc.) for further processing. In variations, such features can include recesses (e.g., dimples, crevices, holes with a base), pores, gaps created within clusters of particles used to form a body, etc. In variations, such features can have a characteristic dimension (e.g., width, length, depth, height, diameter, pore dimension, etc.) of approximately 5 micrometers, 6 micrometers, 7 micrometers, 8 micrometers, 9 micrometers, 10 micrometers, 12 micrometers, 14 micrometers, 16 micrometers, 18 micrometers, 20 micrometers, 22 micrometers, 24 micrometers, 26 micrometers, 28 micrometers, 30 micrometers, 35 micrometers, 40 micrometers, 45 micrometers, 50 micrometers, 55 micrometers, 60 micrometers, 70 micrometers, 80 micrometers, 90 micrometers, 100 micrometers, or another value based upon features of target particle(s) of interest. Features can include affinity molecules coupled to surfaces of the features, physical properties (e.g., surface texture, extracellular matrix components), mechanical properties (e.g., stiffness, elastic moduli, viscoelastic properties, etc.), electrical properties (e.g., electrostatic charge), biochemical properties, or other suitable properties for facilitating retention of tagged particles and/or target analytes from tagged particles at the features. Features can include physical properties, mechanical properties, electrical properties (e.g., electrostatic charge), biochemical properties, or other suitable properties for repelling sample content that is not of interest from the features, in order to improve efficiency of tagging.

In relation to dimensions, the body 30 can have a diameter (or characteristic width) on the order of nanometers (e.g., for intracellular target tagging or other small-scale applications) to micrometers in dimension, where particle size determines the resolution of target analyte location characterization. Dimensional characteristics of the body 30 correspond to scales appropriate for characterization of target analyte locations for various structures (e.g., cells, tissues, and organs, sub-cellular structures, whole organisms, other components, etc.). In variations, the body 30 can have a diameter that is sub-micron up through 10 micrometers; however, alternative variations of the body 30 can have other suitable dimensions (e.g., less than sub-micron, greater than 10 micrometers in diameter). In specific examples, the dimensions of the bodies can be from 3-15 micrometers. In relation to body dimensions below 6 micrometers, tissue processing steps (e.g., permeabilization steps) can be optimized to prevent leakage of targets toward particles not proximal to their respective originating positions at the sample. Exemplary permeabilization reagents can include: organic solvents (e.g., acetone, ethanol, and methanol), cross-linking agents (e.g., paraformaldehyde), detergents (e.g., saponin, Triton X-100™, Tween-20™, or sodium dodecyl sulfate (SDS)), and enzymes (e.g., trypsin, proteases (e.g., proteinase K).

Alternatively, the sample may not be permeabilized, such that the method involves positioning a non-permeabilized tissue sample at the substrate, thereby avoiding target diffusion away from origination positions in the sample, and preventing background noise (i.e., producing high SNR values) during spatial mapping. As such, use of particles having smaller dimensions can still be used to achieve accurate mapping without producing background noise attributed to target leakage or other noise sources.

In variations, the body 130 can have a diameter of 1 micrometer, 2 micrometers, 3 micrometers, 4 micrometers, 5 micrometers, 6 micrometers, 7 micrometers, 8 micrometers, 9 micrometers, 10 micrometers, 11 micrometers, 12 micrometers, 13 micrometers, 14 micrometers, 15 micrometers, 16 micrometers, 17 micrometers, 18 micrometers, 19 micrometers, 20 micrometers, intermediate diameter dimensions, or greater diameter dimensions. For instance, greater diameter dimensions may support features (e.g., recesses, crevices, holes, pores, etc.) described above.

In variations, the distribution of bodies can include different subpopulations of bodies/subpopulations of functionalized particles (e.g., as in FIG. 1G). For instance, the distribution of bodies can include a first subpopulation of bodies having a first diameter (e.g., a diameter below 5 micrometers, another suitable diameter) and/or other first characteristic, and a second population of bodies having a second diameter (e.g., a diameter above 5 micrometers, another suitable diameter) and/or other second characteristic. Additionally or alternatively, the distribution of bodies can include a third subpopulation of bodies having a third diameter and/or other third characteristic, a fourth subpopulation of bodies having a fourth diameter and/or other fourth characteristic, and/or other suitable subpopulations of bodies.

In one application, bodies of a first subpopulation can be functionalized (e.g., with a first handshake molecule type) for release and tagging of a first target type (e.g., cytoplas-mic targets, sample component targets, mRNAs by polyA/polyT interactions, mRNAs by interactions with polyadenylated components, protein targets, other targets that are able to be tagged with a reactive molecule site, etc.). Bodies of the first subpopulation can have a first diameter (e.g., a diameter above 5 micrometers, another suitable diameter). Bodies of a second subpopulation can be functionalized (e.g., with a second handshake molecule type) for release and tagging of a second target type (e.g., targets comprising nuclei or nuclei-associated targets, for instance, with randomer segments, segments that are gene-specific to nuclei targets, segments that tag extended nuclei targets, segments that tag polyadenylated nuclei targets, or other tagging segments for nuclei targets). Bodies of the second subpopulation can have a second diameter (e.g., a diameter below 5 micrometers, another suitable diameter). Bodies of the second subpopulation can be dispersed interstitially (e.g., in spaces between) or amongst the first population at a substrate. As such, in this application, multiple subpopulations of functionalized particles can be implemented in order to tags different targets simultaneously, for characterizations of distributions of different targets using the same system.

In more detail, molecules for tagging a first target type (e.g., cytoplasmic targets, sample surface targets, mRNAs by polyA/polyT interactions, mRNAs by interactions between polyadenylated components and corresponding molecules, etc.) can include: a linker sequence 21, an adaptor sequence 22 (e.g., for a next generation sequencing platform, for library preparation), a first barcode sequence 23, a UP sequence 24, a second barcode sequence 25, a UMI sequence 26, and a polyA-reactive sequence 27 (e.g., dT, dTVN, dU, combination of dT and dU, etc.) for mRNA targets. Molecules structured for mRNA tagging can further include a VN anchor 28 including a dV and a dN (i.e., a V sequence including an A, C, or G nucleotide positioned next to an N sequence including an A, G, C, or T nucleotide) at or near the 3' end. The addition of a VN anchor 28 can promote tagging of mRNAs further into a polyA portion of the mRNA molecule, closer to the 5' end. The addition of the VN anchor 28 can also support approaches for capturing polyadenylated (A-tailed) nucleic acids (e.g., polyadenylated micro RNAs, polyadenylated small nuclear RNAs, polyadenylated viral RNAs, polyadenylated microbial RNAs, polyadenylated RNAs non-host RNAs, polyadenylated coding and non-coding RNAs, etc.), where polyadenylation can involve use of yeast polyA polymerase or other suitable components for polyadenylation. An example of a molecule for mRNA tagging is shown in FIG. 1H (bottom), with sequences positioned in a 5' to 3' direction.

In more detail, molecules for tagging of a second target type (e.g., targets comprising nuclei or nuclei-associated targets, for instance, with randomer segments, segments that are gene-specific to nuclei targets, segments that tag extended nuclei targets, segments that tag polyadenylated nuclei targets, or other tagging segments for nuclei targets) with the goal of spatially mapping the second target type can include: a first linker sequence 31, a PCR handle 32, (e.g., for a next generation sequencing platform, for library preparation), a first barcode sequence 33, a second linker sequence 34, a second barcode sequence 35, a UMI sequence 36, and a handshake sequence 37 for tagging nuclei targets/other targets, upon release of the molecules with cleavage of the first linker sequence 31. In an example, a handshake sequence 37 for tagging of nuclei targets can include a sequence of 5' GCTT-TAAGGCCGGTCCTAGCAA 3'.

An example is shown in FIG. 1H (top), with sequences positioned in a 5' to 3' direction. Molecules for capturing a second target type can be released from their respective bodies 130 (e.g., by way of a cleavage mechanism, such as a photocleavage mechanism, a thermal cleavage mechanism, a chemical cleavage mechanism, an enzymatic cleavage mechanism, etc.) for diffusion toward and for tagging a proximal sample target (e.g., nucleus) with the handshake sequence 37.

In still other variations, one of which is shown in FIGS. 1B and 1C, a distribution of functionalized particles can be configured, such that spaces between functionalized particles serve as features for retaining, partitioning, and/or isolating sample components (e.g., cells, nuclei, cell clusters, single analytes, grouped analytes, etc.) in position at the substrate, for spatial mapping and other characterizations of targets associated with the isolated sample components. As shown in FIGS. 1B and 1C, the sample components can be individually isolated interstitially in spaces between functionalized particles. Alternatively, sample components can be seated upon regions defined by borders of adjacent functionalized particles. In an example, sample components can include single cells. In another example, sample components can include nuclei (e.g., nuclei tagged with barcodes and isolated, as described).

In variations, sample components that are isolated relative to a distribution of functionalized particles at the substrate can be covered (e.g., sealed), with a layer, such as layer 15 described below. In variations, the layer 15 can be composed of optimal cutting temperature (OCT) compound (e.g., OCT compound alone, OCT compound combined with other process reagents, etc.), an oil, an aqueous material, a mesh, a hydrogel, or another suitable material. Covering can thus serve protective functions with respect to maintenance of cell or other target viability and general sample handling, and/or sample processing functions.

With respect to functionalized particles described, the body 130 can have suitable density characteristics (e.g., with density less than, greater than, or equal to various process liquids associated with processing and characterization operations); porosity (e.g., with pore sizes of 100-2000 Angstroms, etc.); thermal properties (e.g., with respect to melting temperatures, with respect to conductivity, with respect to temperature sensitivity/responsiveness, etc.); physical properties (e.g., with respect to swelling characteristics, with respect to leaching characteristics, with respect to hydrophilicity, with respect to crosslinking, etc.); surface properties (e.g., binding sites for linker molecules, functional chemical groups, charge, etc.); magnetic properties (e.g., magnetic properties, and/or paramagnetic properties, for instance by incorporation of magnetic nanoparticles, etc.); and/or other properties. In variations, use of magnetic functionalized particles can be used to deliver functionalized particles into a sample (e.g., into a sample of suspended cells, into a sample of suspended nuclei, into a hydrogel sample, into a tissue sample), upon application of a magnetic force to the functionalized particles. Bodies can additionally or alternatively be dyed or coupled with dyed molecules, where the dyed bodies or molecules can have respective excitation and emission spectrums.

With respect to functionalized particles described, the body 130 can have suitable fluorescence properties (e.g., non-fluorescence so as to not interfere with optical-based detection assays, fluorescent/optical feature properties, such as fluorescence-embedded labels, encoding nucleic acid bases identifiable upon detection of the optical features, etc.); buoyant properties (e.g., in order to arrange particles at a surface due to buoyancy, and applying the sample to the buoyant distribution at the surface to which the buoyant particles migrate); mechanical properties (e.g., hardness, rigidity, elastic behavior, viscoelastic behavior, fatigue resistance, fracture resistance, shear strength, compressive strength, tensile strength, rheological behavior, etc.); solubility (e.g., dissolvable in a solvent, etc.); pH sensitivity; and/or other suitable properties, embodiments, variations, and examples of which are described in U.S. application Ser. No. 17/376,396 filed on 15 Jul. 2021, which is herein incorporated in its entirety by this reference.

In relation to composition, the body 130 can be composed of one or more of: polymers (e.g. polystyrene, polystyrene-divinylbenzene, polymethylmethacrylate (PMMA), etc.), hydrogels, silica, silicon, non-porous glass, porous glass, coated glass, agarose, acrylamide, polyacrylamide, iron, steel, or ceramic materials and/or a combination of one or more suitable materials. Body compositions include those used in peptide, nucleic acid and organic moiety synthesis, including, but not limited to, plastics, ceramics, glass, polystyrene, methylstyrene, acrylic polymers, paramagnetic materials, thoriasol, carbon graphite, titanium dioxide, latex or cross-linked dextrans such as Sepharose, cellulose, nylon, cross-linked micelles, Teflon, and others. Different regions of the body 130 can be composed of different materials (e.g., a core region can be composed of a first material and a shell region can be composed of a second material). Additionally or alternatively, the body can be treated or otherwise compatible with phosphoramidite chemistry for synthesis of oligonucleotides onto the body 130. In specific examples, synthesis can be performed by: synthesizing constant sequences in a single column, followed by deprotection, then distribution of bodies across four columns, each configured to add one of an A, T, G, or C phosphoramidite to the bodies. Then, the bodies can be pooled, mixed well, and redistributed across the four columns for addition of an A, T, G, or C phosphoramidite to the bodies. As such, the barcode sequence added to each bead is randomized, but all oligonucleotides on each bead will have the same sequence. Synthesis can implement use of exonucleases to remove or otherwise avoid undesired levels of truncated oligonucleotides of the functionalized particles. Synthesis can include split pool synthesis or other synthesis approaches (e.g., by linking the 5' end of oligonucleotides containing adaptor sequences to particles to generate functionalized particles, followed by emulsion PCR using primers containing unique barcode sequences).

In some embodiments the body 130 can include multiple regions either as multiple shell regions, or in other configurations such as amorphous or ordered spatial arrangements. In still further examples, the body 130 can include or take the form of a polymeric/molecular body (e.g., DNA nanoball, dendrimer, etc.), where, in applications, the dendrimers can be reduced in size to a "functional monomer" (i.e., as a smallest functional molecular assembly unit).

While particles are described as being positioned on a substrate (e.g., slide), alternative embodiments can include providing distributions of functionalized particles in solution, for interactions with a sample.

2.2.2 Oligonucleotide Segment Aspects

Each body has one or more molecules 140 coupled thereto and structured to provide functionality as described below. The occupancy of molecules at the surface of each particle can be configured to prevent crowding, prevent self-hybridization, and/or enable access of target analytes and/or enzymes as required during processing. In embodiments, a representative functionalized molecule of a distribution of functionalized molecules includes at least: a handshake sequence 141 comprising a reactive portion configured to tag or otherwise bind to a sample target (e.g., nucleus of a cell from a tissue sample), a barcode segment 142, where the barcode segment 142 has a barcode sequence that can serve as a spatial address, and a cleavable linker/releaseable linker 143 configured to allow the handshake sequence 141 to be released from the representative feature 130 (e.g., in response to a stimulus). As described below, the one or more molecules 140 can include or omit regions based upon application of use. The density of the one or more molecules can be at least 10 times more than the amount of target analyte intended for tagging from the sample(s), or otherwise configured with another suitable density in other applications of use.

In examples, the number of functionalized molecules on a particle can be at least 10, 100, 103, 104, 105, 106, 107, 108, 109 or more. It will be understood that each of the molecules on the respective particle or other feature can be present in several copies, for example, when the molecules have been amplified to form a cluster. Thus, the above ranges can describe the number of different nucleic acid clusters on a bead or other nucleic acid-presenting substrate/feature.

2.2.2.1 Handshake Sequences

The handshake sequence 141 functions to tag a target component of the sample (e.g., tissue section), upon release from a functionalized feature and diffusion toward the target component (e.g., nucleus) of the sample. The handshake sequence 141 thus includes a reactive site corresponding to (e.g., complementary to) a molecule of the target component of the sample. The reactive site can thus bind to the target component with a suitable bond, upon release of the handshake sequence and diffusion of the handshake sequence toward the target component (passively, or under active control). The handshake sequence 141 is preferably positioned at a terminal end of a respective molecule, however, the handshake sequence 141 can alternatively be otherwise positioned along a molecule. The handshake sequence can have one or more reactive sites.

A reactive site of a handshake sequence 141 can correspond to (e.g., be complementary to) a nuclei target. A reactive site of a handshake sequence 141 can correspond to (e.g., be complementary to) a cell surface target. A reactive site of a handshake sequence 141 can correspond to (e.g., be complementary to) an intracellular target. A reactive site of a handshake sequence 141 can correspond to (e.g., be complementary to) a nucleic acid target. A reactive site of a handshake sequence 141 can correspond to (e.g., be complementary to) a DNA target (e.g., genomic DNA). A reactive site of a handshake sequence 141 can correspond to (e.g., be complementary to) an RNA target (e.g., mRNA). A reactive site of a handshake sequence 141 can correspond to (e.g., be complementary to) a polyadenylated target.

A reactive site of a handshake sequence 141 can correspond to (e.g., be complementary to) a sample protein target and comprise an NHS ester (i.e., succinimidyl ester) component. A reactive site of a handshake sequence 141 can correspond to (e.g., be complementary to) a tissue extracellular matrix target. A reactive site of a handshake sequence 141 can correspond to (e.g., be complementary to) another spatially distributed target of the sample.

A reactive site of a handshake sequence 141 can be attached to other types of molecules (e.g., antibodies, proteins, peptides, chemicals, etc.), antibodies, aptamers, and/or other suitable target binding segments.

A reactive site of a handshake sequence 141 can correspond to a sequence of a target without 100% complementarity.

A first variation of a handshake sequence 141 can include a sequence for tagging a first target type (e.g., targets comprising nuclei or nuclei-associated targets, for instance, with randomer segments, segments that are gene-specific to nuclei targets, segments that tag extended nuclei targets, segments that tag polyadenylated nuclei targets, or other tagging segments for nuclei targets). An example of a first variation of a handshake sequence 141 is shown in FIG. 1H, top. An example of a handshake sequence 141 for tagging nuclei targets of a sample can include a sequence of 5' GCTTTAAGGCCGGTCCTAGCAA 3'.

A second variation of a molecule with a handshake sequence 141 can include a polyT sequence 27 (e.g., dT, dTVN, etc.) for tagging of mRNA targets (an example of which is shown in FIG. 1E, bottom). Molecules structured for mRNA tagging can further include a VN anchor 28 (shown in FIG. 1H, bottom) including a dV and a dN (i.e., a V sequence including an A, C, or G nucleotide positioned next to an N sequence including an A, G, C, or T nucleotide) at or near the 3' end. The addition of a VN anchor 28 can promote tagging of mRNAs further into a polyA portion of the mRNA molecule, closer to the 5' end. The addition of the VN anchor 28 can also support approaches for tagging polyadenylated (A-tailed) nucleic acids (e.g., polyadenylated micro RNAs, polyadenylated small nuclear RNAs, polyadenylated viral RNAs, polyadenylated microbial RNAs, polyadenylated RNAs non-host RNAs, polyadenylated coding and non-coding RNAs, etc.), where polyadenylation can involve use of yeast polyA polymerase or other suitable components for polyadenylation.

A third variation of a handshake sequence 141 can include a reactive segment configured to support tagging of targets in a manner that does not compete with mRNA tagging (e.g., by other molecules structured for mRNA tagging where the other molecules are coupled to the same particle). A specific example of the third variation of the handshake sequence 141 can include a sequence of 5' AAGCAGTGGTAT-CAACGCAGAGTG 3'. In exemplary use cases, the third variation of the handshake sequence 141 can support applications involving CRISPR screening, antibody tagging, VDJ immune repertoire sequencing, and other applications.

A fourth variation of a handshake sequence 141 can include a reactive segment configured to support 5' tagging of single targets. A specific example of the fourth variation of the handshake sequence 141 can include a sequence of 5' TTTCTTATATrGrGrG 3'. In exemplary use cases, the fourth variation of the handshake sequence 141 can be used to tag 5' ends of targets by taking advantage of non-templated rC nucleotides.

The handshake sequence 141 can, however, be configured for tagging of other targets. For instance, as shown in FIG. 1I, in some variations, targets 5 (e.g., any target type of a sample that can be molecularly labelled) can be labeled (e.g., pre-labeled) with a probe 6 that has a handle corresponding to a handshake sequence, and release of handshake sequences 141 from features of the substrate 110 can allow diffusion of released handshake sequences to the labeled targets, such that the labeled targets can be tagged with barcodes that serve as spatial addresses. As such, methods described can include pre-labeling a set of targets of a sample with a set of probes having handles corresponding to a set of handshake sequences, followed by releasing the handshake sequences for diffusion toward and tagging of the pre-labeled targets of the sample with barcodes that serve as spatial addresses.

Related to the variations described, a functionalized feature at the substrate can include a first subset of molecules with handshake sequences of a first type and a second subset of molecules with handshake sequences of a second type. Fabrication of a particle with different subsets of molecule types can include incorporating a mixture of a recognizable element (e.g., phosphoramidite, such as dt-DMT) and a protecting group (e.g., dA-Lev, where the ratio of the recognizable element and the protecting group in the mixture can be used to control the ratio of the first subset of molecules and the second subset of molecules at a particular functionalized features. The recognizable element and the protecting group can both be configured to couple to running ends of synthesized molecules at the particular functionalized particle. Then, synthesis of the molecules of the first subset of molecules can continue from running ends incorporating the recognizable element, followed by capping (e.g., after final detritylation for dT molecules). Synthesis of molecules of the second subset of molecules can continue from running ends incorporating the protecting group, after deprotection of the protecting group (e.g., removal of the dA-Lev group).

Ratios of the first molecule type to the second molecule type at a functionalized feature can be: 50:50, 49:51, 48:52, 47:53, 46:54, 45:55, 44:56, 43:57, 42:58, 41:59, 40:60, 39:61, 38:62, 37:63, 36:64, 35:65, 34:66, 33:67, 32:68, 31:69, 30:70, 29:71, 28:72, 27:73, 26:74, 25:75, 24:76, 23:77, 22:78, 21:79, 20:80, 19:81, 18:82, 17:83, 16:84, 15:85, 14:86, 13:87, 12:88, 11:89, 10:90, 9:91, 8:92, 7:93, 6:94, 5:95, 4:96, 3:97, 2:98, or 1:99.

In variations where multiple types of molecules are coupled to the same functionalized features, only a subset of molecules can be configured to be releasable cleavable from the functionalized feature (e.g., depending upon intended assay).

Handshake sequences, linker sequences, and/or other adaptor sequences can support downstream single-nucleus RNA-seq (snRNA-seq) assays, single-nucleus ATAC-seq (snATAC-seq) assays, T-cell receptor (TCR) sequencing assays, and/or other assays.

Further embodiments, variations, and examples of the handshake sequence 141 can have overlapping structures with sequences described in U.S. application Ser. No. 17/376,396 filed on 15 Jul. 2021, as incorporated by reference above.

2.2.2.2 Barcode Segment

The barcode segment 142 can serve many functions. The barcode segment 142 can be continuous, or comprise multiple subsegments (e.g., where individual subsegments are separated by one or more linkers or spacers). One or more subsegments of the barcode segment 142 can serve as a spatial address (e.g., upon decoding of the barcode segment and identifying a position of the corresponding molecule at the substrate 110 prior to release of the molecule from the substrate 110 for diffusion toward and tagging of a target of the sample. The barcode segment 142 and/or individual subsegments function to enable identification of the functionalized feature at the substrate with which it is associated, upon sequencing of the barcode segment 142. In some variations, the barcode segment 142 and/or other variations of the barcode segment 142 can also function to enable identification of the substrate 110, entire distribution of functionalized features 120 associated with the substrate 110, and/or other aspects (e.g., upon sequencing). As such, readout of the barcode segment 142 can facilitate characterization of the distribution of targets tagged using the substrate 110 and/or other aspects of the substrate 110 and distribution of functionalized features 120.

The barcode segment 142 is preferably configured to be unique to each functionalized feature. However, some barcode segments 142 associated with different functionalized features at the substrate 110 may overlap across features, as long as spatial information for various target components can still be generally mapped using the substrate. Furthermore, the barcode segments 142 associated with different functionalized features are configured to have diversity such that each functionalized feature or group of functionalized features associated with the substrate 110 can be uniquely identified. In particular, the diversity of the barcode library can be at least 10-fold more than the number of functionalized particles deposited at the substrate, such that almost every functionalized feature has unique barcode on the substrate. Alternatively, the barcode segment 142 can be characterized in terms of diversity in another suitable manner. In embodiments, the barcode segment 142 can have from 5-100 bases in order to provide a sufficient number of unique sequences for a desired number of particles in solution for a given process (i.e., such that each particle can be uniquely identified); however, in alternative variations, the barcode segment 142 can have other suitable numbers of bases (e.g., less than 5 bases, more than 100 bases). Additionally or alternatively, the barcode segment 142 can have a number of bases designed to occupy a percentage (e.g., 10%, 20%, 30%, etc.) of the length of a unit of a respective molecule of a functionalized particle. Barcode segment(s) of functionalized features 120 at a substrate can be decoded to identify a position of a functionalized feature, and thus, any target tagged using the functionalized feature or multiple functionalized features (e.g., relative to the substrate 110, relative to a position within a tissue sample, relative to another suitable datum).

Furthermore, in some variations, a percentage of functionalized features can have known barcode sequences and can be spiked in amongst the distribution of functionalized particles to serve quality control functions for downstream sequencing operations (e.g., in situ sequencing operations).

In examples, functionalized molecules for a feature of the substrate can have the same barcode segment (i.e., each location has identical barcode segments), but have different total molecule lengths. Different lengths allow for identifying the spatial location of a target tagged with a handshake sequence in three dimensions because shorter nucleic acids will diffuse farther into a sample (e.g., tissue section) than a longer nucleic acid. In example embodiments, computational methods can be used to determine the location of tagged targets in a sample with multiple layers of targets, such as by analyzing the number and lengths of functionalized molecules that have tagged each target.

In use, decoding of the barcode segment 142/associated location can be performed using an optical approach (e.g., sequencing-by-synthesis with or without reversible terminators, in-situ sequencing that is ligation based, hybridization based, rolling circle amplification-based, fluorescence in situ hybridization-based, etc.), using a nearest-neighbor approach with a next generation sequencing readout (as described in the applications incorporated by reference), using morphology of the functionalized particles (e.g., using a pattern etched on the particle or other uniquely identifiable particle morphological feature, each feature associated with one barcode), using a combination of fluorescent colors emitted from the functionalized particle (e.g., each combination of fluorescent colors corresponding to a barcode), and/or using another suitable method.

Decoding can thus produce a sequence-verified array of features, such that the sequence of the barcodes that serve as spatial addresses at each feature location, or, greater than a percentage (e.g., 50, 60, 70, 80, 90%, 95%, 99%) of locations, is known. In an example embodiment, the sequences of the barcodes at each location on the substrate are determined by in situ sequencing. In an example embodiment, the features are sequence verified by in situ sequencing before placing a tissue sample on the substrate. In example embodiments, in situ sequencing is performed by sequencing by ligation or sequencing by synthesis directly on the array and captured by microscopy. Alternatively, the array is sequence verified because the barcodes attached to the array at each location were specifically placed at each location.

In examples, decoding of the barcode segment 142/ associated location can include performing a sequencing by ligation (SOLID) operation to decode nucleic acid labels (e.g., with sequencing primer sites, with UP primer sites, etc.) and positions of associate labels on functionalized particles at the substrate. Sequencing/decoding can be performed using a microfluidic device having a flow cell by which units the system 100 are processed for decoding prior to packing and delivery (e.g., in series, in parallel). The microfluidic device can thus control flow of materials for interactions with units of the substrate, in coordination with an imaging system having a field of view encompassing the substrate(s) configured to capture images from which sequences of the barcode segments can be determined in relation to substrate positions.

In examples, decoding of the barcode segment can use other sequencing-based approaches. For instance, decoding can be performed using sequencing with error-reduction by dynamic annealing and ligation (SEDAL), sequencing from a 5' to 3' direction, sequencing from a 3' to 5' direction, and/or other sequencing processes. In variations, decoding can include performing a set of iterations of SEDAL sequencing, performing a set of iterations of sequencing from a 5' to 3' direction, and performing a set of iterations of sequencing from a 3' to 5' direction. The iterations of sequencing can use the same reagents and/or different reagents (e.g., using different primers). In variations, the number of iterations of each sequencing approach can be 1 iteration, 2 iterations, 3 iterations, 4 iterations, 5 iterations, 6 iterations, 7 iterations, 8 iterations, 9 iterations, 10 iterations, 15 iterations, or more iterations, where the numbers of iterations of each sequencing process can be the same or different.

The decoding passing rate can be greater than 50%, greater than 60%, greater than 70%, greater than 80%, greater than 90%, or greater, where the decoding passing rate can be determined based on a set of criteria.

The set of criteria can include one or more of: a particle number criterion, a shape score criterion, a substrate coverage criterion, a criterion regarding amount of empty space (e.g., patches) on the substrate; a dominant barcode fraction per bead/feature criterion, a base call quality criterion, an image registration criterion, a region of interest correlation criterion, a region of interest area criterion, and an overall pass/fail criterion.

Particle number criterion: This criterion is based upon a number of enumerated particles on the substrate, where, in an example, the number of particles can be from 60,000-80,000 particles for a 3 mm×3 mm distribution of particles to pass the particle number criterion.

Shape score criterion: This criterion is based upon evaluation of a region of interest of the substrate spanning a portion of the distribution of particles on the substrate, and relates to an expected morphology of the distribution of particles on the substrate. In an example, the shape score can indicate that the region does not have square morphology (or other undesired morphology) in order to pass the shape score criterion.

Substrate coverage criterion: This criterion relates to density of coverage of the distribution of particles on the substrate, with respect to an expected density of coverage (e.g., for a random close-packed distribution, for another close-packed distribution, for another distribution). In an example, the substrate coverage can be greater than 90% (or more) of the expected density of coverage in order to pass the substrate coverage criterion.

Criterion regarding amount of empty space: This criterion relates to presence of observable empty spaces, such as empty patches on the substrate. In an example, an empty patch can be defined as a contiguous patch that is missing more than 5 particles, more than 6 particles, more than 7 particles, more than 8 particles, more than 9 particles, more than 10 particles, or greater.

Criterion regarding a dominant barcode fraction per bead/feature: In an example, each respective particle should only have one dominant barcode segment sequence across all oligonucleotides on the respective particle that serves as the spatial address. If the average (e.g., mean, median, etc.) barcode segment sequence is not above a certain percentage of barcode segment sequences on the respective particle, the criterion is not passed. In an example, the passing rate can be greater than 50% identical barcode segment sequences on the particle, greater than 55% identical barcode segment sequences on the particle, greater than 60% identical barcode segment sequences on the particle, greater than 65% identical barcode segment sequences on the particle, greater than 70% identical barcode segment sequences on the particle, greater than 75% identical barcode segment sequences on the particle, etc.

Base call quality criterion: This criterion captures a signal to noise ratio (SNR) for base call quality. In examples, the base call quality (e.g., SNR) is greater than 2, greater than 3, greater than 4, or greater to pass the criterion.

Image registration criterion: This criterion relates to registration of multiple images used for decoding of positions of particles on the substrate. If the images are not captured properly, the image registration criterion characterizes deviation across image edges. Any observable deviation results in not passing the criterion.

Region of interest correlation criterion: This criterion describes a correlation between the expected shape of an ROI and the actual shape, where the correlation must be greater than 90%, greater than 91%, greater than 92%, greater than 93%, greater than 94%, greater than 95%, greater than 96%, greater than 97%, or greater to pass the criterion.

Region of interest area criterion: This criterion evaluates presence of missing particles at the edge of the distribution of functionalized particles, or presence of functionalized particles outside of the intended distribution of functionalized particles.

Overall pass/fail criterion: This is criterion evaluates all the criteria mentioned. In examples, all criteria must be satisfied to pass the overall pass/fail criterion.

Barcode segments 142 can be stochastic or non-stochastic. Barcode segments can have a total length from 6 to 100 bases long, depending upon application of use. Alternatively, barcode segments can have a total length less than 6 bases, or from 100 to 200 bases long, depending upon application of use. In a specific example, a representative barcode segment 142 has a length of 14 bases, and includes a first barcode subsegment having 8 bases and a second barcode subsegment having 6 bases, where the subsegments are separated by a linker.

2.2.2.3 Linker for Molecule Release and Diffusion Toward Target

The cleavable linker 143 is coupled to the body 130 (or alternatively, other functionalized feature of the substrate 110 or the substrate itself 110) and functions to provide a mechanism by which molecules coupled to the body 130 or substrate can be controllably released from the body 130 or substrate in order to diffuse toward and tag a target of the sample. The cleavable linker 143 can also extend units of the one or more molecules 140 out into space, thereby enabling interactions of the one or more molecules 140 with target analytes (e.g., nuclei targets) of the sample that can benefit from tagging with cleavable linkers, or that are difficult to access without use of cleavable molecules.

In embodiments, the first cleavable linker 143 is configured for selectable attachment (e.g., with functional groups specific to specific chemistries) and/or activatable cleavage, to enable controlled release of the one or more molecules 140 from the body 130. In variations, activatable cleavage or separation in another manner can be achieved with linker regions configured to be cleave in response to one or more of: a thermal cleavage mechanism, a pH shift, a photocleaving mechanism, an enzymatic cleaving mechanism (e.g., as in molecular scissors), a chemical cleaving mechanism, separation based upon changes in charge, or another suitable cleaving mechanism.

In variations, photocleaving can be achieved with photocleavable linkers that controllably cleave with specific light characteristics (e.g., wavelengths, intensities, exposure times, etc.). In such variations, controlled cleavage characteristics can prevent undesired cleavage of molecules (e.g., prior to use, such as in storage environments with ambient or other forms of light). In examples, photocleavable linkers can be structured to cleave with exposure to ultraviolet (UV) light (e.g., from 100-400 nm in wavelength), with an exposure time of 1 second, 2 seconds, 3 seconds, 4 seconds, 5 seconds, 10 seconds, 30 seconds, 60 seconds, 90 seconds, 100 seconds, 200 seconds, 300 seconds, or greater. However, the photocleavable linker can alternatively be configured to cleave in response to non-UV light.

An exemplary photocleavable linker can have the following structure and cleave upon being exposed to ultraviolet light with a wavelength of 300-350 nm:

However, other photocleavable linkers or photo-responsive components can be used.

In composition, the cleavable linker 143 can be composed of a polymer (e.g., non-nucleic acid polymer), and in a specific example, the cleavable linker 143 can be composed of polyethylene glycol (PEG) or another suitable polymer. However, the cleavable linker 143 can be composed of another suitable material (e.g., natural material, synthetic material).

In structure, the cleavable linker 143 can have a linear structure that extends units of the one or more molecules 140 into space. Alternatively, the cleavable linker 143 can have a branched or otherwise non-linear structure (e.g., dendrimer segment, dual-linking segment, other branched segment). For instance, in variations in which the cleavable linker 143 is configured to control spacing/density of molecules coupled to the body 130 or other feature, the cleavable linker 143 can have a branched structure that reduces density and/or controls spacing/orientation of molecules coupled to the body 130 or other feature. Additionally or alternatively, the length and/or structure of the o cleavable linker 143 can be configured to prevent steric hindrance of any enzyme or material that would interact with the oligonucleotide molecules during use. Exemplary dual-linker structures can have a free OH group on a 5' end of the structure, or a phosphoramidite on a 5' end of the structure to improve loading density characteristics. Branched structures can include protecting groups (e.g., lev protecting groups).

In relation to properties, the cleavable linker 143 can be configured with a desired charge and/or other characteristic (e.g., level of hydrophilicity, level of hydrophobicity, etc.) that prevents undesired interactions between molecules (e.g., tangling, clumping, undesired structures, etc.). As such, the cleavable linker 143 can be configured to extend molecules of the one or more molecules 140 into space (e.g., perpendicular from a surface of the body 130); however, the cleavable linker 143 can be configured to extend from the body 130 or other feature in another suitable manner.

In variations, units of the one or more molecules can omit or include additional segments as needed. For instance, one or more of the one or more molecules 140 can include segments configured for amplification reactions (e.g., PCR handles, etc.). Additionally or alternatively, one or more of the one or more molecules 140 can include unique molecular identifiers (UMIs). Additionally or alternatively, one or more of the one or more molecules 140 can include fluorescence-embedded labels (e.g., in order to provide a mechanism where components tagged with handshake sequences, such as nuclei, can be identified and sorted out from non-tagged components, in order to provide a mechanism for determining the efficiency of component with handshake sequences by quantitating a percentage or ratio of tagged component to untagged components). Additionally or alternatively, one or more of the one or more of the one or more molecules can include segments configured to simplify library preparation steps or sequencing processes of specific sequencing platforms. In more detail, molecules of the one or more molecules can include adapter segments (e.g., associated with P5/P7 adapters for Illumina™ platforms), index sequences associated with adapters, and/or other sequences. Additionally or alternatively, additional segments can be added during sample processing (e.g., during reverse transcription, etc.). Units of the one or more molecules 140 can additionally or alternatively include other sequences (e.g., for other fragmentation, sequencing, and/or processing platforms). In embodiments, the molecules can be produced or otherwise synthesized by at least one of split pool synthesis (e.g., chemically, with an oligo synthesizer, etc.), enzymatic synthesis (e.g., with ligation and polymerase extension), by emulsion PCR, by template-free synthesis (e.g., using terminal transferase, etc.), and/or by other suitable methods, as described in more detail below.

Functionalized molecules can further include a nucleotide modification to enhance diffusion to targets (e.g., nuclei) of a sample. In examples, functionalized molecules can include or be coupled to a lipophilic or amphiphilic moiety that can interact with and/or insert itself into lipid membranes such as cell membranes and nuclear membranes. Examples of lipophilic molecules can include sterol lipids (e.g., cholesterol, tocopherol, derivatives, etc.); lignoceric acid, palmitic acid, and other moieties. Other lipophilic molecules suited to applications described can include amphiphilic molecules wherein the charge, aliphatic content, aromatic content, and/or fatty acid chain length can be varied. In examples, fatty acid side chains (e.g., C12, C14, C16, or C18) can be coupled to glycerol or glycerol derivatives, which can also include a cationic head group.

Functionalized molecules can thus be coupled with one or more lipophilic moieties by way of a linker (e.g., a tetraethylene glycol (TEG) linker, a polyethylene glycol (PEG) linker, etc.). Other exemplary linkers can include an Amino Linker (e.g., C6, C12), a space (e.g., C3, C6, C12, 9, 18), or other linker or space. The lipophilic moiety or the linker can be coupled to the functionalized molecule at the 5' end or other suitable portion. The functionalized molecules can be structured to be releasably attached to the linker or lipophilic moiety (e.g., according to variations of mechanisms described) such that a functionalized molecule or a portion thereof can be released from the lipophilic/amphiphilic molecule. In example embodiments, a lipophilic moiety (e.g., a cholesterol) is indirectly coupled to an oligonucleotide (e.g., via hybridization or ligand-ligand interactions, such as biotin-streptavidin).

In relation to capturing of different targets (e.g., cytoplasmic targets, nuclei targets, protein targets, targets from other sample regions, etc.), functionalized particles can have molecules with different PCR handles corresponding to different target types, in order to enable selective amplification, detection, and mapping of different target types.

Functionalized particles can have different subsets of types of molecules coupled thereto (e.g., as in FIG. 1G), where a first subset of molecules can be cleaved (e.g., in order to tag a first target type such a nuclei target) by a first mechanism, and a second subset of molecules may not be cleavable (or cleavable by a second mechanism different than the first mechanism), in order to tag a second target type (e.g., a cytoplasmic target). The first cleaving mechanism or the second cleaving mechanism can include: a thermal cleavage mechanism, a pH shift, a photocleaving mechanism, a chemical cleaving mechanism, an enzymatic cleaving mechanism (e.g., as in molecular scissors), separation based upon changes in charge (e.g., as in an electrostatic interaction), or another suitable cleaving/separation mechanism. In relation to cleaving, samples or processing reagents can include diffusion limiting compounds (e.g., long-chain polymers, such as in polyethylene glycol solutions), in order to prevent diffusion of cleaved functionalized particles beyond a threshold distance away from originating positions. Diffusion limiting compounds can thus enable accurate mapping of targets, even when cleavable tagging molecules are implemented to tag targets post cleaving. In use cases where a nuclei target is tagged with functionalized molecules originating from different functionalized particles (e.g., as determinable using barcode sequences or other spatial tag sequences), bioinformatics can be used to characterize locations of such nuclei targets, as well as diffusion behavior of cleaved molecules (e.g., average distances diffused in order to arrive at a target), which can be used to improve SNR of maps generated.

For instance, in embodiments where a nucleus is tagged using cleavable molecules of functionalized particles, tagging of the nucleus can involve tagging the nucleus with different cleavable molecules associated with different spatial positions. A bioinformatics approach can involve determining the position of the nucleus based upon a subset of positions corresponding to a subset of stochastic barcodes of molecules that tagged the nucleus. The position of the nucleus can be determined from an average position of the subset of stochastic barcodes (e.g., a centroid of positions of the subset of stochastic barcodes). In variations, nuclei can be tagged using a combination of cleavable and non-cleavable molecules (or molecules cleaved in different stages and in response to different stimuli), such that positions of the nuclei can be determined from stochastic/spatial barcode positions of cleavable and non-cleavable molecules (e.g., as a weighted centroid of positions, where positions of non-cleavable components are weighted more heavily than positions of cleavable components). As such, the position estimated from the barcodes serving as spatial addresses can be an estimation of the location in or on a sample, in or on a feature (e.g., functionalized particle) or a combination thereof.

In situations where a tagged nucleus, tagged cell, or other tagged sample component has more than one tag, noise can be filtered by generating positional data using sequences associated with only one UMI or a subset of UMIs for tagged components.

Different molecules configured to tag different targets can be coupled to the same particle/feature/body. Alternatively, different subpopulations of particles/features/bodies can be paired with different molecules configured to tag different targets.

For instance, in one embodiment, the distribution of functionalized features at the substrate 110 can have different subsets of types of molecules coupled thereto (e.g., as in FIG. 1H), where the different subsets of types of molecules include different platform-specific sequences. For instance, a first subset of molecules can include sequences specific to a first platform, a second subset of molecules can include sequences specific to a second platform, a third subset of molecules can include sequences specific to a third platform, etc. The platforms (e.g., the first platform, the second platform, the third platform, etc.) can be different single-cell analysis platforms (e.g., involving different adaptor sequences, different priming sequences, etc.), different sequencing platforms (e.g., involving different adaptor sequences, different priming sequences, etc.), different single-nuclei analysis platforms (e.g., involving different adaptor sequences, different priming sequences, etc.), different partitioning platforms, and/or different platforms of another type. The different platforms can be from the same manufacturer/supplier and/or different manufacturers/suppliers. In the embodiment shown in FIG. 1H the subsets of molecules can be configured to tag the same type of target (e.g., nuclei target, cytoplasmic target, cell surface target, intracellular target, etc.) and differ with respect to spatial sequences and platform-specific sequences. Alternatively, the subsets of molecules can be configured to tag the different types of targets (e.g., nuclei target, cytoplasmic target, cell surface target, intracellular target, etc.) and differ with respect to the tagging sequences configured to bind with (e.g., hybridize with, etc.) the different targets, spatial sequences, and platform-specific sequences.

With respect to individual functionalized features, different subsets of types of molecules can be coupled to the same functionalized feature. Alternatively, an individual functionalized feature can have only one type of molecule subset (e.g., molecules specific to one platform) coupled thereto. With respect to the different subsets of types of molecules, each subset can be configured to be cleaved from its respective functionalized feature using the same cleaving mechanism, or different cleaving mechanisms (e.g., in order to provide differential control over cleaving of the different subsets of types of molecules). Cleaving mechanisms for the different subsets of types of molecules can include: a thermal cleavage mechanism, a pH shift, a photocleaving mechanism, a chemical cleaving mechanism, an enzymatic cleaving mechanism (e.g., as in molecular scissors), separation based upon changes in charge (e.g., as in an electrostatic interaction), or another suitable cleaving/separation mechanism.

With respect to a first subset of molecules and a second subset of molecules for instance, the first subset of molecules can be configured to be cleaved in response to a first stimulus including one of: a thermal cleavage mechanism, a pH shift, a photocleaving mechanism, a chemical cleaving mechanism, an enzymatic cleaving mechanism (e.g., as in molecular scissors), separation based upon changes in charge (e.g., as in an electrostatic interaction), or another suitable cleaving/separation mechanism. The second subset of molecules can be configured to be cleaved in response to a second stimulus including one of: a thermal cleavage mechanism, a pH shift, a photocleaving mechanism, a chemical cleaving mechanism, an enzymatic cleaving mechanism (e.g., as in molecular scissors), separation based upon changes in charge (e.g., as in an electrostatic interaction), or another suitable cleaving/separation mechanism, different from the first cleaving/separation mechanism.

Alternatively, with respect to a first subset of molecules and a second subset of molecules for instance, the first subset of molecules and the second set of molecules can be configured to be differentially cleaved in response to different parameters of the same type of stimulus or mechanism. For instance, in relation to a photocleaving mechanism, the first subset of molecules can be configured to cleave in response to a first wavelength of light, and the second subset of molecules can be configured to cleave in response to a second wavelength of light different than the first wavelength of light. Different exposure times for different photocleaving mechanisms can also be used. In another example, in relation to a thermal cleaving mechanism, the first subset of molecules can be configured to cleave in response to a first thermal stimulus, and the second subset of molecules can be configured to cleave in response to a second thermal stimulus different than the first thermal stimulus. In another example, in relation to a chemical cleaving mechanism, the first subset of molecules can be configured to cleave in response to a first chemical stimulus (e.g., first enzyme), and the second subset of molecules can be configured to cleave in response to a second chemical stimulus (e.g., second enzyme) different than the first chemical stimulus.

Molecules can be coupled to functionalized particles with a suitable density of molecules per particle. For instance, a particle can have on the order of 10 s to 100 s of molecules for mapping nuclei targets and/or other target types.

Additionally or alternatively, molecules can be coupled to functionalized particles with a suitable percentage of surface area covered by molecules, where the percentage can be 5%, 10%, 15%, 20%, 25%, 30%, 35%, 40%, 45%, 50%, 55%, or another suitable percent coverage. Percent coverage, in addition to other sample processing aspects described, can improve recovery rate of nuclei targets mapped (e.g., in relation to actual numbers of nuclei targets present) to greater than 15%, greater than 20%, greater than 25%, greater than 30%, greater than 35%, greater than 40%, greater than 45%, greater than 50%, or greater.

Some embodiments, variations, and examples of molecule segments are further described in U.S. application Ser. No. 17/376,396 filed on 15 Jul. 2021, which is incorporated by reference above.

2.3 System—Support Structure and Use

Figure 2A:
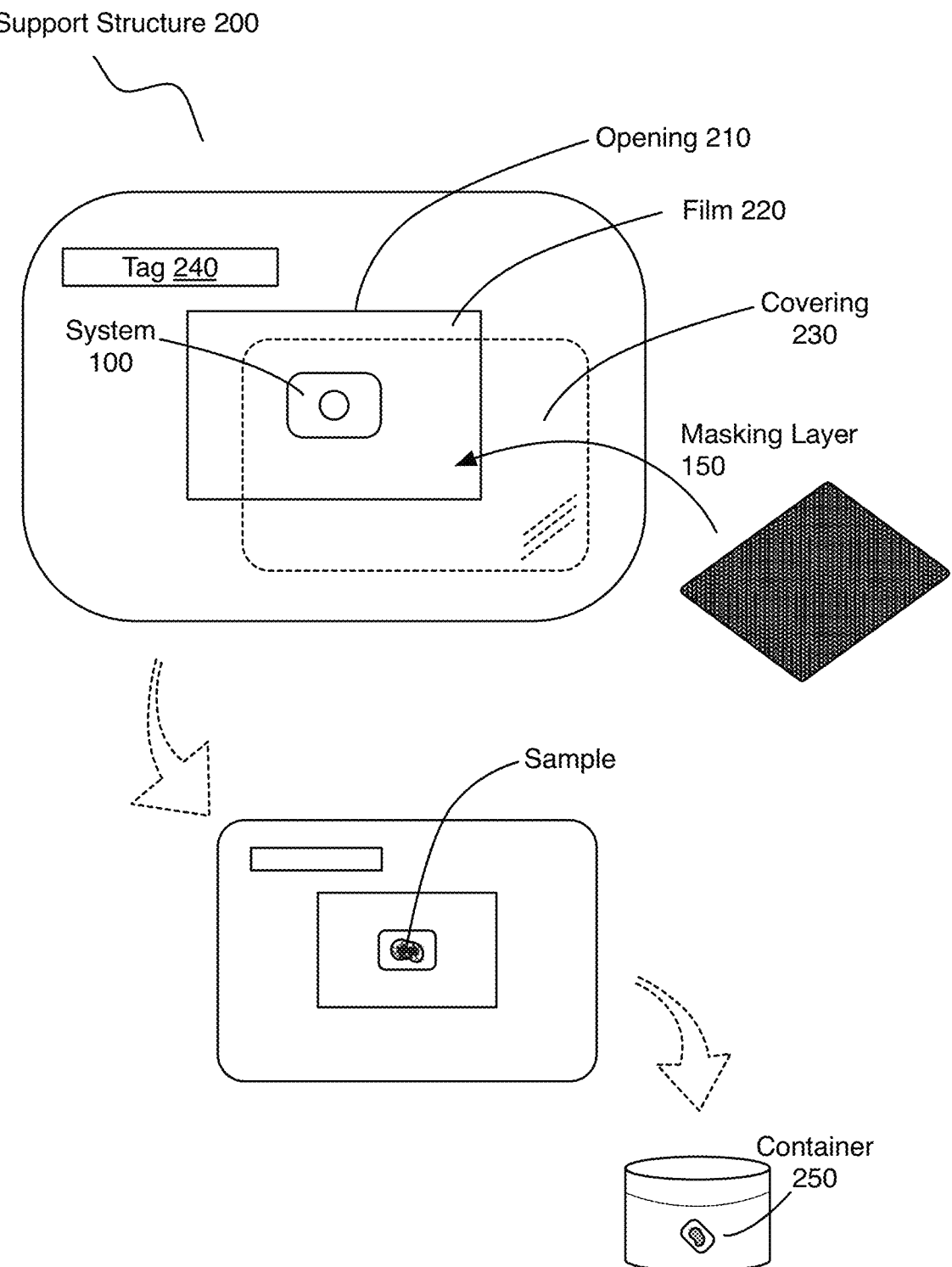
FIG. 2A depicts a schematic of an embodiment of a support structure for a system for characterizing locations of targets in space, using releasable handshake sequences.

As shown in FIG. 2A, the invention(s) can further include a support structure 200, which functions to support one or more units of the system 100 and to facilitate usage of the system 100 by a sample-processing entity. In embodiments, the support structure 200 can retain one or more units of the system 100 in position, facilitate contacting of units of the system 100 by a tissue sample or other sample, and enable release of the one or more units of the system 100 from the support structure 200 for further processing, post-interactions with sample material.

Figure 2B:
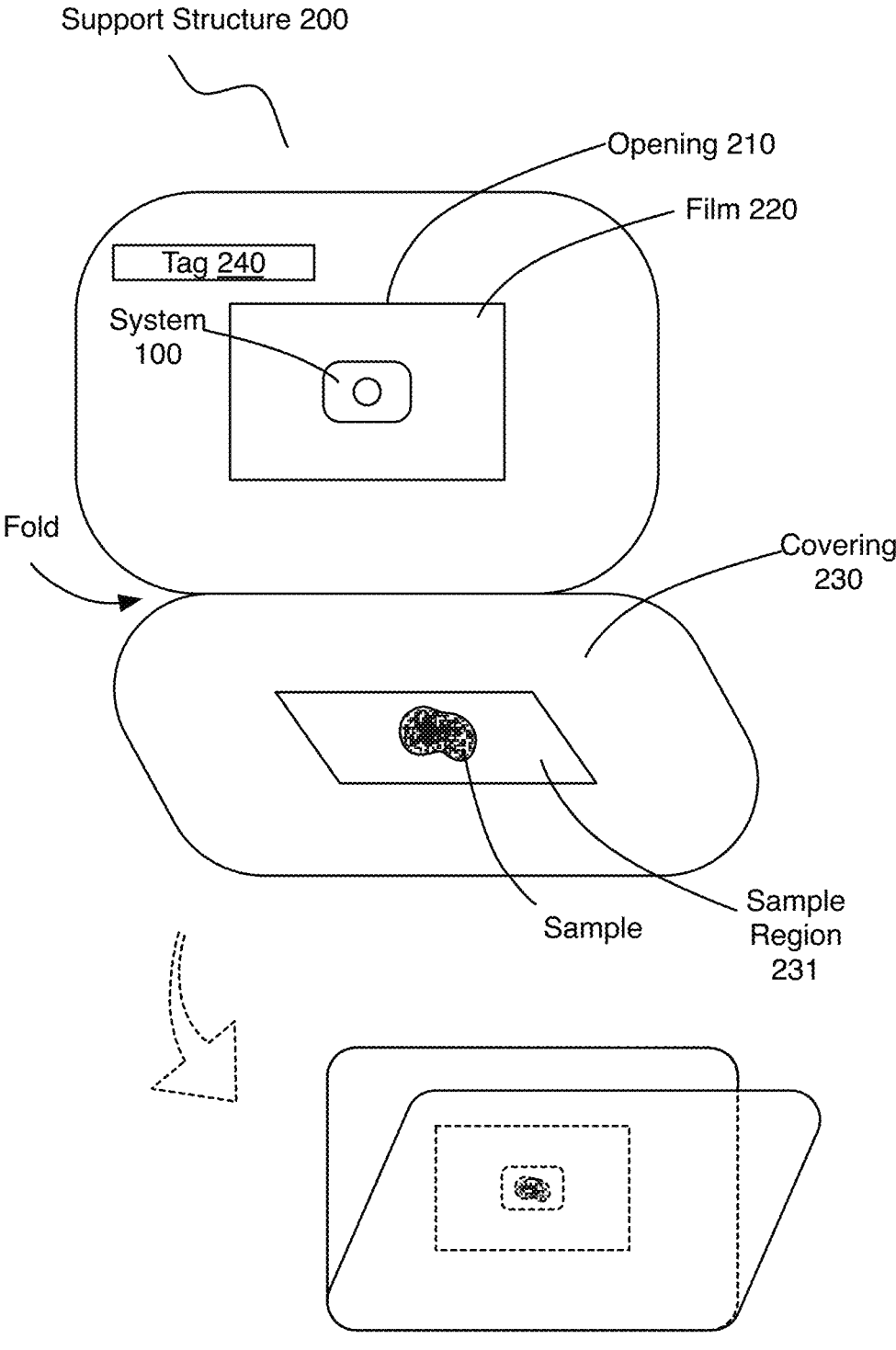
FIG. 2B depicts a schematic of a variation of a support structure for a system for characterizing locations of targets in space, using releasable handshake sequences.

In embodiments, as shown in FIGS. 2A and 2B, the support structure 200 includes: an opening 210, and a flexible film 220 coupled to the support structure about the opening 210 at a first surface of the support structure, and supporting one or more units of the system 100 (e.g., substrate 110 with functionalized particles 120, array of substrates with functionalized particles, etc.) within the opening 210. In variations, the support structure 200 can further include one or more of: a protective covering 230 opposing the flexible film 220 at the opening 210, and a tag 240 encoding information associated with the system 100/ substrate 110. In variations, the support structure 200 can be configured for use with masking layer 150 described in further detail below.

Details of embodiments, variations, and examples of the support structure 200 and related structural components are further described as follows:

In embodiments, the support structure 200 is composed of a material that provides protection from environments associated with transportation and/or use of the system 100. As such, the support structure 200 can function to provide one or more of: impact resistance (e.g., to protect fragile portions of the system 100), flame-proofing/resistance; sealing (e.g., as in a hermetic seal, in order to prevent intrusion of moisture prior to use, in order to prevent intrusion of gases prior to use, etc.); optical properties (e.g., with respect to shielding from electromagnetic energy, with respect to allowing transmission of light for enabling optical detection or visual observation through the support structure 200, etc.); electrical properties (e.g., with respect to shielding from electric fields, etc.); and/or other suitable properties. In examples, the support structure 200 can be composed of a polymer material, a fibrous material, a foam, or another suitable material.

In morphology, the support structure 200 can have a broad surface, where the broad surface is rectangular in morphology; however, in other variations, the support structure 200 can have another suitable defined morphology (e.g., circular morphology, ellipsoidal morphology, polygonal morphology, amorphous morphology, etc.). In examples, the support structure 200 can have a characteristic length from 1-15 centimeters, a characteristic width from 1-15 centimeters, and a characteristic thickness from 0.5-5 millimeters; however, the support structure 200 can alternatively have other suitable dimensions.

In variations, the support structure 200 can include features configured to facilitate handling by an operator. For instance, the support structure 200 can include surface regions with high-friction (e.g., to facilitate gripping by a human or robotic operator), markings (e.g., to provide indications of orientation, to guide proper usage of the support structure 200 in relation to various operation modes, etc.), and/or other features.

The opening 210 functions to enable an operator to interact with the system 100 according to operation modes described below, when the system 100 is supported by the support structure 200. In particular, the opening 210 can allow the operator to transmit heat to a sample (e.g., through the flexible film 220 described in more detail below) and/or to displace the system 100 from the support structure 200 (e.g., by application of a mechanical force to the flexible film 220 described in more detail below). The opening 210 can be rectangular in morphology; however, in other variations, the opening can have another suitable defined morphology (e.g., circular morphology, ellipsoidal morphology, polygonal morphology, amorphous morphology, etc.). In examples, the opening 210 can have a characteristic length from 0.2-10 centimeters, a characteristic width from 0.2-10 centimeters, and a characteristic depth from 0.5-5 millimeters; however, the support structure 200 can alternatively have other suitable dimensions.

The support structure 200 can include a single opening 210. Alternatively, the support structure 200 can include a set of openings (e.g., arranged as an array, arranged in another suitable manner), where each opening of the set of openings is configured to support one or more units of the system 100.

The flexible film 220 functions to support the system 100 within the opening 210 (or multiple openings), and to enable operation modes described in more detail below. Properties of the flexible film 220 can allow an operator to transmit heat to a sample (e.g., through the flexible film 220 and/or substrate 110) and/or to displace the system 100 from the support structure 200 (e.g., by application of a mechanical force to the flexible film 220).

In embodiments, the flexible film 220 is retained in position about the opening 210 (e.g., coupled to a broad surface of the support structure 210, retained between layers of the support structure 210, etc.). The flexible film 220 can be retained without any slack or under tension. Preferably, the flexible film 220 is retained in a manner such that application of force or heat to the flexible film 220, as intended during use during operation modes described below, does not compromise coupling of the flexible film 220 to the support structure 200 or compromise its functionality. Alternatively, the flexible film 220 can be retained in position about the opening 210 in another suitable manner.

The flexible film 220 is preferably composed of a material processed with: suitable mechanical properties (e.g., in relation to tear strength, in relation to strain behavior, in relation to allowing plastic deformation for displacement of the system 100 from the support structure 200, in relation to allowing elastic deformation for displacement of the system 100 from the support structure 200, etc.), optical properties (e.g., degree of transparency to allow observation of a a unit of the system 100 coupled to the flexible film 220 during use), thermal properties (e.g., in relation to conductivity for transmission of heat to a sample through the flexible film 220 and substrate 110, in relation to melting temperature, etc.), surface and bulk properties (e.g., in relation to charge, in relation to degree of hydrophobicity, in relation to porosity, etc.), electrical properties, and/or other suitable properties. The flexible film 120 can have a thickness from 75 to 150 micrometers (or alternatively, another suitable thickness).

In embodiments, the flexible film 120 is a flexible polymer film composed of polyvinyl chloride (PVC), polyolefin, polyethylene, polyethylene terephthalate (PET), nylon, and/or another suitable polymer material. In variations, the flexible film 120 further includes an adhesive layer coupled thereto, in order to provide a mechanism for coupling with units of the system 100 in a non-permanent manner. In variations, the adhesive layer is composed of an acrylic adhesive; however variations of the adhesive layer can be composed of another suitable material. The adhesive layer can have an adhesive strength configured based upon size and mass characteristics of the system 100 and/or in relation to specified force required to displace a unit of the system 100 from the flexible film 120 during use. In a specific example, the flexible film 120 is a PVC dicing tape used during manufacturing of the substrate 110 (e.g., with respect to scribing and sawing of the substrate 110); however, in variations of the specific example, the flexible film 120 can be otherwise composed and configured.

For instance, as an alternative to mechanical breaking of adhesive bonds, the adhesive layer can be structured such that adhesive bonds are broken upon exposure to specific wavelength ranges of light (e.g., ultraviolet light, etc.), thermal stimulation (e.g., upon exposure to heat at certain temperature ranges), and/or another suitable mechanism.

The protective covering 230 functions to protect units of the system 100 supported by the support structure 200 (e.g., during transportation, during phases of use, etc.). In some embodiments the protective covering 230 is composed of the same material as the bulk material used for the support structure 200; however, the protective covering can alternatively be composed of another suitable material, embodiments, variations, and examples of which are described above.

The protective covering 230 can be an element separate from the bulk material of the support structure 200, such that the protective covering 230 can be provided with the support structure 200 (e.g., in relation to the kit/package described in more detail below), and removed from the support structure 200 during use. Alternatively, the protective covering 230 can be physically contiguous with the bulk material of the support structure 200 and/or transitionable between a covered mode (e.g., in which units of the system 100 are covered) and an uncovered mode (e.g., in which units of the system 100 are uncovered), where transition between modes can be enabled through folding, sliding, or another mechanism facilitated by structural relationships between the protective covering 230 and the bulk material of the support structure 200. In one such variation, as shown in FIG. 2B, the protective covering 230 can be folded over the opening 210 in the covered mode, and unfolded in the uncovered mode.

Sample retention and positioning for interactions with the system 100 can, however, be enabled by other suitable sample positioning structures.

Furthermore, in relation to operation modes described in more detail below, the protective covering 230 can include a sample region 231 configured to support or retain a sample, as shown in FIG. 2B, where the sample can be positioned at the sample region 231, and then transition of the protective covering 230 to the covered mode (e.g., through folding, through another mechanism) can position the sample into contact with the system 100 for sample processing in a consistent and reliable manner.

The tag 240 functions to encode information pertaining to one or more of the support structure 200, units of the system 100 supported by the support structure 200, reagents being provided with a kit including the support structure 200, the sample(s) being processed using the support structure 200, molecular barcode information (e.g., spatial locations associated with different molecular barcodes of distributions of functionalized features 120, etc.). In variations, information encoded by the tag 240 can include one or more of: batch number (e.g., of the support structure 200, of a system 100 unit, of reagents), lot number (e.g., of the support structure 200, of a system 100 unit, of reagents), sample-identification information, patient or subject information associated with a sample, molecular barcode information (e.g., spatial locations associated with different molecular barcodes of distributions of functionalized particles 120, etc.), other spatial information (e.g., associated with a position of a system 100 unit at the support structure, associated with spatial locations of material at the system 100 unit), other molecular information, and/or other suitable information.

In embodiments, the tag 240 can be a computer-readable tag. In embodiments, the tag 240 can thus have the form of a barcode, a QR code, a code including characters (e.g., alpha-numeric characters, other characters, etc.), or another suitable code that is readable upon scanning (e.g., with an optical detection subsystem). Additionally or alternatively, the tag 240 can be a digitally-readable tag (e.g., decoded upon transmission of electrical signals).

Figure 3:
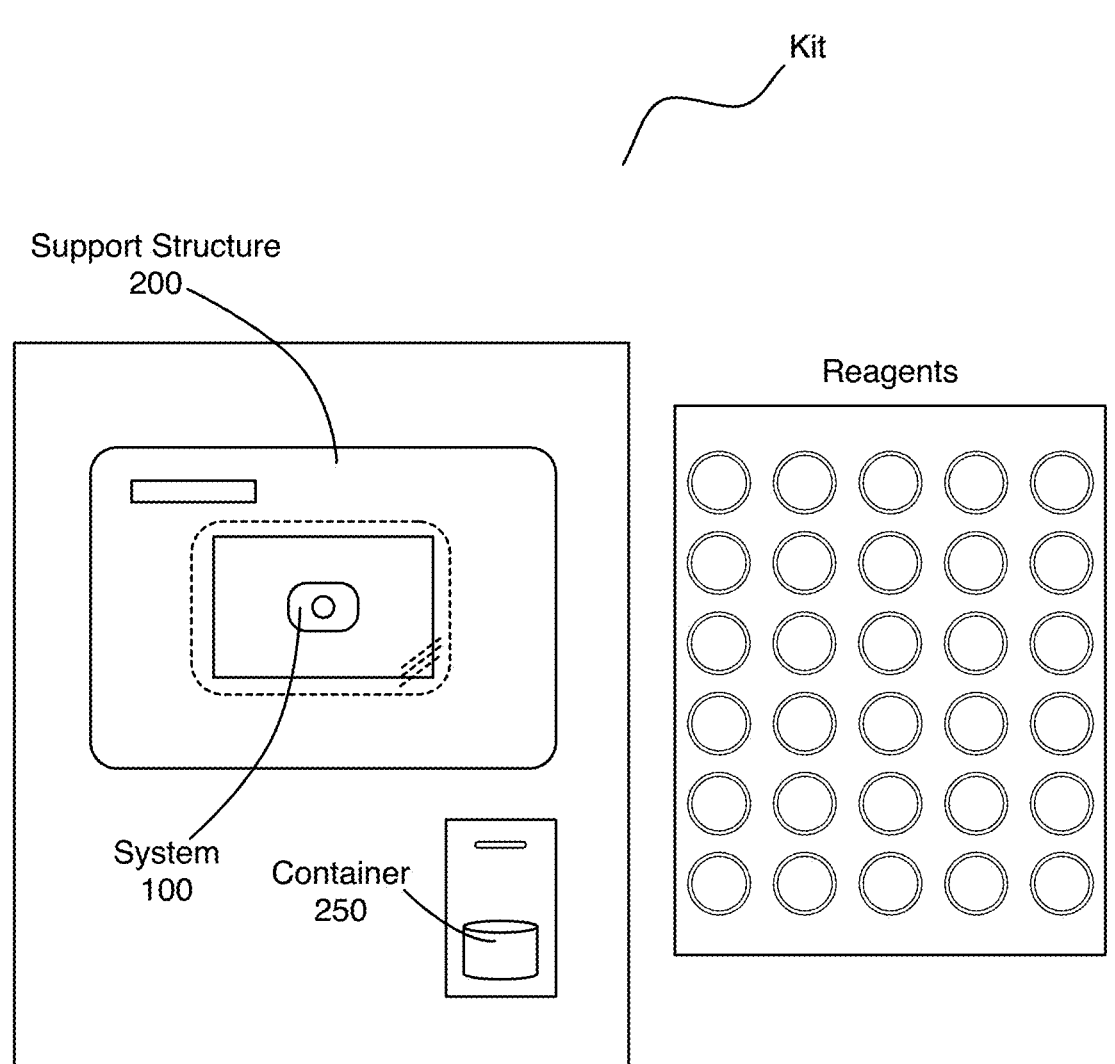
FIG. 3 depicts a schematic of a kit including elements for characterizing locations of targets in space, using releasable handshake sequences.

In embodiments, the support structure 200 with one or more units of the system 100 can be provided as a kit (as shown in FIG. 3), where the support structure 200 is assembled (e.g., pre-packaged) with the one or more units of the system 100, including the substrate 110 with the distribution of functionalized features 120. The kit can further include a process container 250 configured to receive one or more units of the system 100 (e.g., in relation to operation modes described below where the system 100 is displaced from the support structure into a container 250, such as a process container or collecting container).

Additionally or alternatively, the kit can further include one or more reagents for sample processing operations and/or for library preparation operations. One or more of the reagents can be provided in separate containers; additionally or alternatively, one or more of the reagents can be provided in container 250 (e.g., pre-packaged in container 250), in order to stabilize or store material captured at a unit of the system 100 (e.g. prior to transportation or other downstream processing operations).

In a variation, provided reagents can be configured for one or more of: sample target component isolation (e.g., nuclei isolation post-tagging of nuclei with handshake sequences), sample component washing (e.g., nuclei washing), sample processing (e.g., with Bovine Serum Albumin, with RNase inhibitor), or other components. Optional components/reagents can include one or more of: ethyl alcohol, dyecycle or AO/PI or DAPI stains, Trypan Blue, or other reagents.

Optional components provided with the kit can include one or more of a cryostat, a microscope, a light source (e.g., UV lamp) for release of functionalized molecules, light source components (e.g., drivers, power supplies, lamp holders), a refrigerated centrifuge, aspiration and delivery devices (e.g., pipettes, pipette tips, irrigators, such as Water-pik™ devices, etc.), a mini centrifuge, a vortexer, a tweezer, containers, razor blades, optimal cutting temperature (OCT) compound, particle strainers, etc.

In other variations, provided reagents can be designed for reception/storage of the system 100 at a first temperature (e.g., –20 C). In examples, the reagents can include one or more of: RNase inhibitor, superscript/reverse transcriptase buffer, reverse transcriptase enzyme, dNTPs, reverse transcription enzyme, template switching oligonucleotides, exosome isolation reagents, TC enzyme/buffer, superscript enzyme, amplification primers, PCR reagents (e.g., PCR buffer, PCR primer mix, PCR enzyme, etc.), proteinase $K_2$, exonuclease, cDNA amplification buffer, cDNA amplification primer mix(es), cDNA amplification enzyme, TE, and/or other suitable reagents.

In other variations, provided reagents can be designed for reception/storage of the system 100 at a second temperature (e.g., 4 C, etc.). In examples, the reagents can include one or more of: functionalized particle washing buffer, TC enzyme/buffer, water (e.g., nuclease-free water), hybridization buffer, tissue clearing buffer, Tris buffer, sodium hydroxide, and/or other suitable reagents.

In other variations, provided reagents can be designed for reception/storage of the system 100 at a third temperature (e.g., room temperature, etc.). In examples, the reagents can include one or more of: functionalized particle washing buffer, TC enzyme/buffer, water (e.g., nuclease-free water), hybridization buffer, and/or other suitable reagents.

Additionally or alternatively, reagents can be configured for library preparation and/or other assays. In examples, library preparation materials can support hybridization (e.g., hybridization with whole genome sequencing primer sites, with universal primer (UP) sites, etc.), template switching reverse transcription (RT), sample and bead removal (e.g., within process container 250), exonuclease treatment or other methods of removing single stranded oligonucleotides from functionalized particles, denaturation steps (e.g., involving sodium hydroxide), second strand synthesis, and/or other aspects of library preparation.

Reagents of the kit can be provided in a separate housing (e.g., container, box, etc.) from the support structure 200 and/or other system elements, examples of which are shown in FIG. 3. Additionally or alternatively, reagents of the kit can be provided in the same housing (e.g., container, box, etc.). Additionally or alternatively, the kit can include open receptacles (e.g., for optional or custom reagents), or can otherwise omit reagent provision.

Additionally or alternatively, the kit can include training substrates (e.g., substrates with or without functionalized particles, and/or with or without decoding of functionalized particle positions at the substrate), which can be used by new users to practice application of a sample to the substrate and/or to practice other aspects of using the kit.

Other examples of the kit can include: one or more units of a substrate with functionalized particles for tagging nuclei of a sample (embodiments, variations, and examples of which are described above), a set of reagents (e.g., dissociation buffers, extraction buffers, wash buffers, RNase inhibitors, etc.) for nuclei isolation of a sample, and/or other components.

In a first example, a substrate of a kit can include a population of bodies having a first diameter (e.g., a diameter of 10 microns) and/or other first characteristic, where bodies of the subpopulation can be functionalized (e.g., with a first tagging molecule type comprising a first handshake sequence type) for tagging a sample target (e.g., targets comprising nuclei or nuclei-associated targets, for instance, with randomer segments, segments that are gene-specific to nuclei targets, segments that tag extended nuclei targets, segments that tag polyadenylated nuclei targets, or other tagging segments for nuclei targets). Bodies of the population can be randomly or non-randomly distributed across the active region of the substrate. Variations of the first example can provide populations of bodies in multiple formats (e.g., as a 3 mm×3 mm array, as a 10 mm×10 mm array, etc.).

In a second example, a substrate of a kit can include a first subpopulation of bodies having a first diameter (e.g., a diameter of 10 microns, a diameter of 3 microns) and/or other first characteristic, and a second subpopulation of bodies having a second diameter (e.g., a diameter of 10 microns, a diameter of 3 microns) and/or other second characteristic. In the first example, bodies of the first subpopulation can be functionalized (e.g., with a first tagging molecule type) for tagging a first target type (e.g., cytoplasmic targets, sample surface targets, mRNAs by polyA/polyT interactions, mRNAs by interactions between polyadenylated portions and corresponding molecules, etc.). Bodies of the second subpopulation can be functionalized (e.g., with a second tagging molecule type) for tagging a second target type (e.g., targets comprising nuclei or nuclei-associated targets, for instance, with randomer segments, segments that are gene-specific to nuclei targets, segments that tag extended nuclei targets, segments that tag polyadenylated nuclei targets, or other tagging segments for nuclei targets). Bodies of the first subpopulation and the second population can be randomly or non-randomly distributed across the active region of the substrate.

In a third example, a substrate of a kit can include a first subpopulation of bodies having a first diameter (e.g., a diameter of 10 microns) and/or other first characteristic, and a second subpopulation of bodies having a second diameter (e.g., a diameter of 3 microns) and/or other second characteristic. In the first example, bodies of the first subpopulation can be functionalized (e.g., with a first tagging molecule type) for tagging a first target type (e.g., cytoplasmic targets, sample surface targets, mRNAs by polyA/polyT interactions, mRNAs by interactions between polyadenylated portions and corresponding molecules, etc.). Bodies of the second subpopulation can be functionalized (e.g., with a second tagging molecule type) for capturing a second target type (e.g., targets comprising nuclei or nuclei-associated targets, for instance, with randomer segments, segments that are gene-specific to nuclei targets, segments that tag extended nuclei targets, segments that tag polyadenylated nuclei targets, or other tagging segments for nuclei targets). Bodies of the second subpopulation can be dispersed interstitially (e.g., in spaces between) or amongst the first population at a substrate without compromise of mapping resolution for all target types. As such, in this application, multiple subpopulations of functionalized particles can be implemented in order to tag different targets simultaneously, for characterizations of distributions of different targets using the same system.

In a fourth example, a substrate of a kit can include bodies with a first subset of molecules functionalized (e.g., with a first tagging molecule type) for capturing a first target type (e.g., cytoplasmic targets, sample surface targets, mRNAs by polyA/polyT interactions, mRNAs by interactions between polyadenylated portions and corresponding molecules, etc.) and a second subset of molecules functionalized (e.g., with a second tagging molecule type) for tagging a second target type (e.g., targets comprising nuclei or nuclei-associated targets, for instance, with randomer segments, segments that are gene-specific to nuclei targets, segments that tag extended nuclei targets, segments that tag polyadenylated nuclei targets, or other tagging segments for nuclei targets). An example is shown in FIG. 1G with respect to particles of a second particle type.

A workflow associated with the first, the second, and the third examples of the kit can involve: receiving a sample at the substrate with the distribution of functionalized particles; performing a hybridization reaction with tagging portions of functionalized molecules of the functionalized particles with targets of a first target type (e.g., nuclei targets) and targets of a second target type (e.g., cytoplasmic targets) of the sample (e.g., with release of functionalized molecules in response to a stimulus); performing a tissue dissociation operation and a nuclei processing operation; and performing sequencing operations for generating spatial maps of the first target type and the second target type across the sample.

2.3.1 Masking Layer

As shown in FIGS. 1A and 2A, the system 100 or support structure 200 can include a masking layer 150 that functions to protect functionalized features from prematurely being exposed to stimuli or otherwise damaged in a manner that prevents the handshake sequences from being controllably released from the distribution of functionalized features 120 for tagging targets of a sample. The masking layer 150 can have the form of a sticker or other label that can be applied (e.g., to the support structure, to the flexible film, to a side of the substrate, etc.) in order to protect functionalized features 120 of the substrate 110 prior to use.

In variations, the system 100 or support structure 200 can include multiple masking layers or a masking layer that includes sections that can be separated from each other (e.g., with perforations). In these variations, controlled release of handshake sequences from different regions of a substrate 110 can involve removal of individual masking layers and/or sections of a separatable masking layer, followed by exposure to a suitable stimulus (e.g., light wavelength) to release handshake sequences. As such, methods described below can include covering the distribution of functionalized molecules of the substrate with a masking layer and removing the masking layer prior to applying the stimulus.

2.3.2 Support Structure—Example Operation and Variations

During use, the support structure 200 can provide a set of operation modes for sample processing (e.g., with respect to protecting aspects of the system 100 during shipping/handling/processing, with respect promoting contact between units of the system 100 and samples during processing, with respect to enabling release of units of the system 100 from the support structure 200 for downstream processing, etc.).

Figure 4:
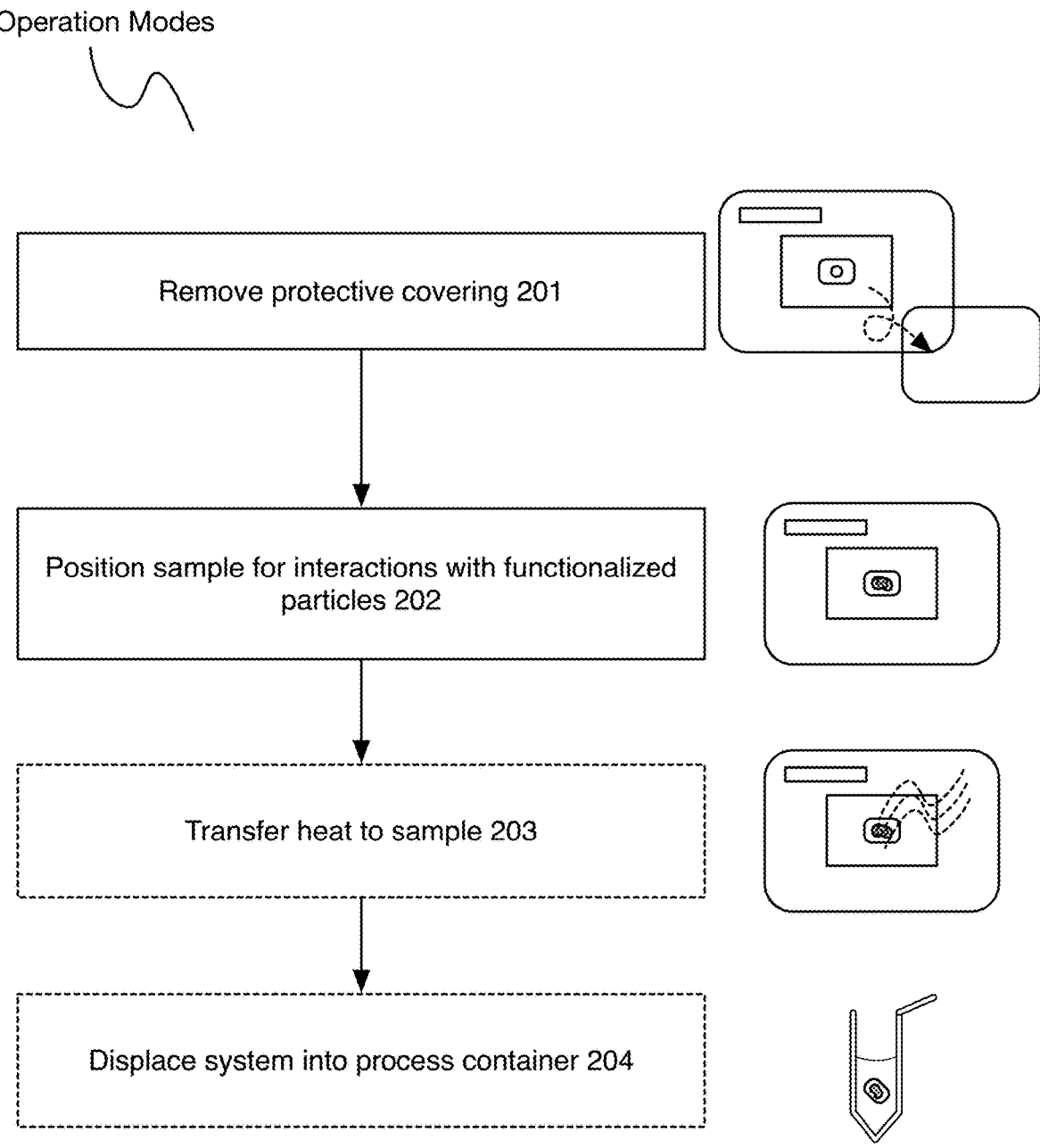
FIG. 4 depicts a flowchart of an example workflow of a system for characterizing locations of targets in space.

In variations, as shown in FIG. 4, the set of operation modes can include a first operation mode 201 in which the protective covering 230 is removed from the support structure 200 or otherwise positioned away from the substrate 110; and a second operation mode 202 in which a sample is positioned in contact with the substrate 110 and the distribution of functionalized particles 120. The set of operation modes can further include a third operation mode 203 in which heat is transferred from the substrate 110 to the sample (e.g., in variations in which the sample is frozen, in variations in which the sample is paraffin-embedded, etc.); and a fourth operation mode in which the flexible film 220 is deformed, thereby displacing the substrate 110, with or without the sample, from the support structure 200 and into a process container 250. Additionally or alternatively, additional operation modes can include facilitating removal of functionalized particles or cleared tissue from the substrate 110, within the process container 250 (e.g., by aspiration and delivery of liquid within the process container 250 to dislodge functionalized particles, nuclei, and/or cleared tissue from the substrate 110 after they have interacted with the sample).

As described above, the first operation mode 201 and the second operation mode 202 can be associated with covered and uncovered modes provided by the protective covering 230, where the protective covering 230 can receive the sample, and transition to the covered mode (e.g., by folding), in order to position the sample into contact with the distribution of functionalized particles 120 at the substrate 110. Operation modes 201 and 202 can be enabled by variations of the support structure 200 in another suitable manner (an example of which is described in relation to variation of the support structure 200b below).

In relation to operation mode 203, heat can be transferred from the substrate 110 to the sample through the flexible film 220. In a first example, an operator can position a warm object (e.g., finger, heating element, etc.) against the flexible film 220 opposite the system 100, and heat from the warm object can be transmitted to the sample (e.g., to melt the sample). In another example, a platform (e.g., automated platform) can transmit heat to the sample with a heat source (e.g., plate heater, convective heater, etc.) in thermal communication with the sample (e.g., through the flexible film, through the support structure, through the substrate, etc.). In particular, in relation to operation modes described, at least one of the flexible film 220, the substrate 110, and the support structure 100 has a thermal conductivity of greater than a thermal conductivity threshold (e.g., 0.05 W/mK), providing a thermal transmission pathway to the sample during operation.

In relation to operation mode 204, the flexible film 220 is deformed, to displace the substrate 110 from the support structure 200 and into a process container 250 for transportation, storage and/or further processing (e.g., sequencing, etc.). In one variation, an operator can apply a force to the flexible film 220 (e.g., backside of the flexible film 200), to displace the substrate 110 from an adhesive layer coupled to the flexible film 220. In another variation, a robotic apparatus can apply a force (e.g., using a tip or other extremity) to the flexible film 220 (e.g., backside of the flexible film 200), to displace the substrate 110 from an adhesive layer coupled to the flexible film 220. In alternative variations, operation mode 204 can omit implementation of a mechanical force, and instead application of light within a specified wavelength range (e.g., UV light) and/or application of heat (e.g., at a specified temperature range) can promote separation of the substrate 110 from the film 220.

Additionally or alternatively, in relation to operation mode 204, the system can include a magnetic component 24 (e.g.) coupled to the substrate 110, or to which the substrate 110 with the distribution of functionalized particles is transferred, prior to transfer of the substrate 110 into the process container, as shown in FIG. 5 (Top). Furthermore, the system 100 or other entity performing sample processing can apply magnetic forces (e.g., by actuating a magnetic wand/stylus 25) to the substrate 110, in order to control motion of the substrate 110 into, out of, or within the process container 250 during sample processing steps.

Additionally or alternatively, in relation to operation mode 204, the system can include a cage/cassette 26 into which the substrate 110 with the distribution of functionalized particles is transferred in coordination with interacting the distribution of functionalized particles with the sample, where the cage/cassette can be manipulated more easily than the substrate, for controlling motion of the substrate 110 into, out of, or within the process container 250 during sample processing steps, as shown in FIG. 5 (Bottom).

In variations the film may not be flexible and can instead be rigid.

The invention(s) described can support further operation modes and/or include other elements. For instance, the invention(s) can include a flow cell configured to receive one or more units of the system 100 (e.g., post-interaction with samples, and post-displacement from a support structure), where the flow cell enables sequencing of target analytes, material derived from tagged and processed target analytes, and/or other sample processing steps. Such a flow cell can thus include a fluid channel in communication with the distribution of functionalized particles at the substrate of a unit of the system, and enable optical detection of signals generated from tagged and/or processed target analytes of the sample. Furthermore, the flow cell can enclose one or more units of the system for higher throughput and/or multiplexed operations.

Figure 6:
FIG. 6 depicts schematics of another variation of a support structure for a system for characterizing locations of targets in space and method of use.

Alternative Variation: In an alternative variation, as shown in FIG. 6, the support structure 200b can include a tip 210b supporting one or more units of the system 100, where, during use, the tip 210b can be positioned into contact with a sample, and the unit(s) of the system 100 can be displaced from the tip 210b to contact a specific portion of the sample. In examples, the unit(s) of the system 100 can be coupled to the tip 210b using a layer (e.g., adhesive layer), where contact with the sample provides a force that separates the system 100 from the layer to interact with the sample. Additionally or alternatively, the tip 210b and/or other portion of the support structure 200b can provide a controlled release mechanism using, for example, a plunger (e.g., mechanical plunger that displaces the system 100 from the tip 210b), magnetic forces (e.g., in which reversible polarity or removal of magnetic forces displaces the system 100 from the tip 210b), or other forces are used to separate the system 100 from the tip 210b.

Furthermore, the variation of the support structure 200b described can include multiple tips individually supporting units of the system 100, where the multiple tips can be synchronously controlled and/or individually controlled to displace respective units of the system 100 to promote sample interactions, target tagging, target location characterization, and/or other aspects of sample processing.

In a specific application of use, a sample/tissue can still be integrated with a patient or other subject (e.g., not removed from the patient/subject), and in specific examples, the sample/tissue can include a skin sample (e.g., lesion) or other section of tissue made accessible (e.g., during a procedure for biopsy, during orthoscopy, during endoscopy, etc.), allowing sampling of the tissue without removal from the patient. For instance, in one specific use case, during removal of cancerous tissue, the support structure 200b can apply one or more system units to the neighboring tissue to help confirm if the cancerous tissue is completely removed. Alternatively, the support structure 200b can apply a unit of the system to a tissue, followed by cleavage to tage targets of the tissue, and then biopsy of the tissue post-tagging. The support structure 200b can, however, be applied in other suitable manners.

Still other variations of the support structure can be otherwise configured with respect to promoting interactions with samples for target tagging, target analyte location characterization, and/or other aspects of sample processing. For instance, the system can include a sample positioning structure configured to retain the sample in position relative to the substrate.

3. METHODS AND EXAMPLE APPLICATIONS OF USE

Figure 7B:
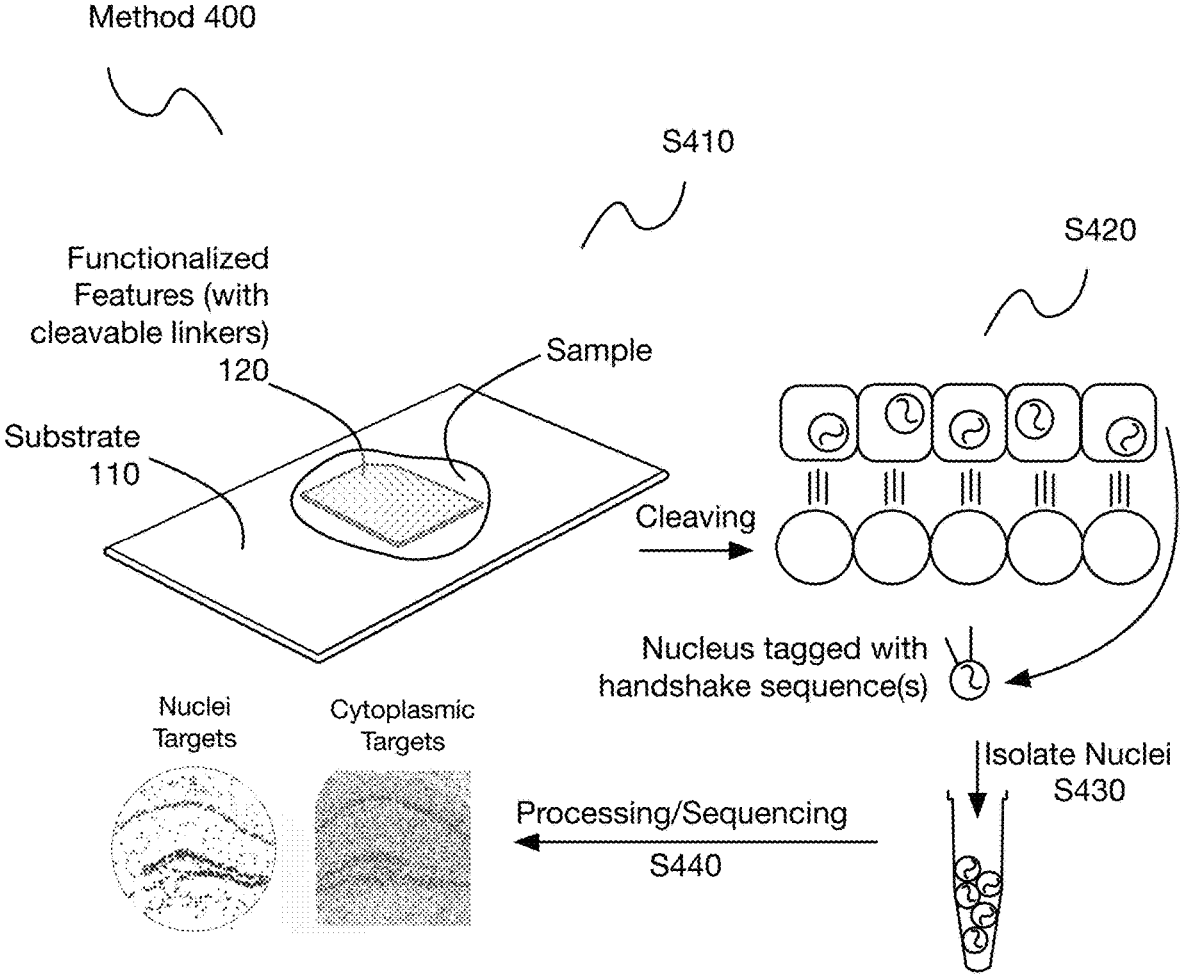
FIG. 7B depicts a schematic of an embodiment of a method for characterizing locations of targets in space, using releasable handshake sequences.

As shown in FIGS. 7A and 7B, an embodiment of a method 400 for generating a spatial analysis of a sample can include: processing a sample comprising a set of targets (e.g., nuclei, cells) with a substrate comprising a distribution of tagging molecules comprising barcode sequences that serve as spatial addresses S410; tagging the set of targets with handshake sequences of the distribution of tagging molecules (e.g., upon cleaving the distribution of tagging molecules (e.g., with application of a stimulus) and allowing them to diffuse toward the set of targets) S420; isolating targets (e.g., nuclei, cells) of the set of targets of the sample S430; and determining positions of targets of the set of targets upon sequencing molecules generated from the distribution of tagging molecules S440 (e.g., by determining a set of sequences of resultant molecules generated from the set of nuclei and the distribution of functionalized molecules, thereby determining a set of spatial positions of the set of nuclei based upon the barcode sequences associated with each of the set of nuclei). Optionally, in some embodiments, methods can include tagging (e.g., microfluidic tagging, tagging within microwells, tagging within partitions, tagging within droplets of an emulsion) and barcoding of targets (e.g., mRNAs, other targets of nuclei and/or cells) after isolation of targets in step S430.

As shown in FIG. 7C, an embodiment of a method 500 for generating an analysis of single cells of a sample can include: generating a set of labelled cells, upon tagging a set of cells with a first set of oligonucleotides S510; seating the set of labeled cells at interstitial spaces of a distribution of functionalized particles coupled to a substrate S520 (wherein each functionalized particle contacts no more than one labelled cell of the set of labelled cells); generating a single cell sequencing library from amplicons generated from a set of reactions involving the set of labelled cells and molecules of the distribution of functionalized particles S530; and returning a single cell analysis of the set of cells upon sequencing the single cell sequencing library S540.

As shown in FIG. 7D, an embodiment of a method 600 for generating an analysis of single nuclei of a sample can include: generating a set of labelled nuclei, upon tagging a set of nuclei with a first set of oligonucleotides S610; seating the set of labeled nuclei at interstitial spaces of a distribution of functionalized particles coupled to a substrate S620, wherein each functionalized particle contacts no more than one labelled nucleus of the set of labelled nuclei; generating a single nucleus sequencing library from amplicons generated from a set of reactions involving the set of labelled nuclei and molecules of the distribution of functionalized particles S630; and returning a single nucleus analysis of the set of nuclei upon sequencing the single nucleus sequencing library S640.

Embodiments, variations, and examples of the methods 400, 500, and 600 function to provide an efficient and high-performance method for tagging distributed targets (e.g., nuclei, cells) of a sample with oligonucleotide tags that encode spatial positions (e.g., spatial positions corresponding to originating positions of the oligonucleotide tags on a substrate, spatial positions corresponding to coordinates of the distributed targets across the sample, etc.). As such, the methods 400, 500, 600 generate spatially tagged and isolated single nuclei from samples (e.g., tissue samples, other sample types), as described.

The methods 400, 500, and 600 can also provide profound enhancements to single nuclei and single cell analyses, by pre-processing single nuclei targets and single cell targets with spatial tags, prior to processing single nuclei targets and single cell targets with single nuclei and single cell sample processing workflows that characterize genomics, transcriptomics, proteomics, metabolomics and/or other features of single nuclei/cells. The methods 400, 500, and 600 also provide significant improvements in performance with respect to retrieval and isolation of single nuclei/cells after spatially tagging such single nuclei/cells.

Embodiments, variations, and examples of the methods 400, 500, and 600 also function to improve workflows for performing single cell, single nucleus, or other single-particle analyses, by providing new mechanisms for tagging and spatially-isolating individual cells, nuclei, and/or other particles, while requiring less control and less complicated setups for singularizing biological content under analysis and combining singularized biological content with reagents (e.g., reagent particles) for analyzing singularized biological content. Embodiments, variations, and examples of the methods 400, 500, and 600 function to enhance single cell, single nuclei, and/or other single particle analyses, with the addition of spatial localization information (e.g., involving spatial characterizations in situ, in vitro, involving cyto-architectural organizational information, etc.).

In particular, the methods described can provide single-cell and single-nuclei spatial analysis results without having to re-invent existing molecular assays in a spatial context, and without having to re-invent solutions for addressing problems with cellular mixing. Furthermore, the method(s) described can consistently achieve (e.g., at commercial scale) efficient tagging of cell and nuclei profiles from tissue sections, with retention of spatial localization information, at high resolution, with applicability to any single cell or single nucleus methodology. Resolution of mapping of single cells and single nuclei can be achieved according to performance specifications described above.

The methods can thus include generating a spatial map of a distribution of nuclei isolated from a tissue sample, upon tagging the distribution of nuclei with a set of handshake sequences paired with a set of barcode sequences that serve as spatial addresses, wherein generating the spatial map comprises recovering and mapping positions of more than a percentage (e.g., 20%, 30%, 40%, 50%, 60%, 70%, 80%, 90%, etc.) of nuclei originally present in the tissue sample.

The methods can generate high-resolution spatial sequencing maps of single cells, single nuclei, or other targets of the sample(s), where, in examples, the methods can achieve resolutions of: greater than one target mapped per 500 $um^2$, greater than one target mapped per 400 $um^2$, greater than one target mapped per 300 $um^2$, greater than one target mapped per 200 $um^2$, greater than one target mapped per 150 $um^2$, greater than one target mapped per 100 $um^2$, greater than one target mapped per 50 $um^2$, greater than one target mapped per 40 $um^2$, greater than one target mapped per 30 $um^2$, greater than one target mapped per 20 $um^2$, greater than one target mapped per 10 $um^2$, or any intermediate number of targets mapped per unit area.

The methods can generate high-resolution spatial maps of targets of the sample(s), where, in examples, the method 400 can achieve resolutions of: greater than one target mapped per 500 $um^2$, greater than one target mapped per 400 $um^2$, greater than one target mapped per 300 $um^2$, greater than one target mapped per 200 $um^2$, greater than one target mapped per 150 $um^2$, greater than one target mapped per 100 $um^2$, greater than one target mapped per 50 $um^2$, greater than one target mapped per 40 $um^2$, greater than one target mapped per 30 $um^2$, greater than one target mapped per 20 $um^2$, greater than one target mapped per 10 um², or any intermediate number of targets mapped per unit area.

The methods can provide rapid, high-performance workflows for spatial mapping of nuclei, cells, and/or other sample components, where the entire workflow from sample handling (and application to a substrate with functionalized features) to sequencing (e.g., snRNA-seq, scRNA-seq, RNA-seq, TCR, etc.) and mapping can be accomplished within a low duration of time. As such, the methods cover generating a spatial map of a distribution of nuclei isolated from a tissue sample, upon tagging the distribution of nuclei with a set of handshake sequences paired with a set of barcode sequences that serve as spatial addresses, wherein generating the spatial map is performed within a duration of less than 10 hours, less than 9 hours, less than 8 hours, less than 7 hours, less than 6 hours, less than 5 hours, less than 4 hours, less than 3 hours, less than 2 hours, or less than 1 hour.

In particular, with respect to nuclei mapping, nuclei dissociation from the substrate can have a duration less than 1 hours, less than 45 minutes, less than 30 minutes, less than 20 minutes, less than 10 minutes, less than 5 minutes, or less.

With respect to nuclei tagging, a nuclei tagging workflow can have a duration less than 3 hours, less than 2 hours, less than 1 hour, less than 45 minutes, less than 30 minutes, less than 20 minutes, less than 10 minutes, less than 5 minutes, or less.

Mapping can be performing for each of a set of at least 2 targets, 3 targets, 4 targets, 5 targets, 6 targets, 7 targets, 8 targets, 9 targets, 10 targets, 11 targets, 12 targets, 13 targets, 14 targets, 15 targets, 16 targets, 17 targets, 18 targets, 19 targets, 20 targets, 25 targets, 30 targets, 40 targets, 50 targets, 100 targets, 1000 targets or any intermediate number of targets simultaneously, at resolutions described.

The methods can further achieve generation of spatial maps that have a resolution of less than a threshold distance between features (e.g., beads or other particle bodies, rods, protrusions, recesses, ridges, valleys, channels, wells, oligonucleotide spots, etc.) of a substrate for target tagging interactions. Embodiments, variations, and examples of spatial maps generated have a resolution of less than 50 picometers between features, less than 40 picometers between features, less than 30 picometers between features, less than 20 picometers between features, less than 10 picometers between features, less than 5 picometers between features, or less than 1 picometer between features In embodiments, the targets characterized spatially according to the methods can include one or more of: nucleic acid material (e.g., DNA, RNA, miRNA, etc.), protein material, amino acid material, other small molecules, other single analytes, other multianalytes, and/or other suitable target material of a sample. In embodiments, the sample can include whole tissue structures, tissue portions (e.g., histological tissue slices, formalin-fixed paraffin-embedded (FFPE) tissue, frozen tissue, biopsied tissues, fresh frozen plasma, seeded natural scaffolds, seeded synthetic scaffolds, etc.), organs, whole organisms, organoids, cell suspensions (e.g., frozen cell suspensions that are separated prior to processing with the system, cell suspensions retained in a medium/hydrogel medium, etc.), nuclei suspensions, single cells, organelles, sub-organelle structures, intra-organelle components, mitochondrial targets, viruses, microorganisms, and other samples.

Slices of tissues, cells, or suspensions (e.g., cell suspensions, nuclei suspensions, etc.) can be 0.1 micrometers thick, 0.25 micrometers thick, 0.5 micrometers thick, 0.75 micrometers thick, 1 micrometer thick, 2 micrometers thick, 3 micrometers thick, 4 micrometers thick, 5 micrometers thick, 6 micrometers thick, 7 micrometers thick, 8 micrometers thick, 9 micrometers thick, 10 micrometers thick, 11 micrometers thick, 12 micrometers thick, 13 micrometers thick, 14 micrometers thick, 15 micrometers thick, 16 micrometers thick, 17 micrometers thick, 18 micrometers thick, 19 micrometers thick, 20 micrometers thick, 25 micrometers thick, 30 micrometers thick, or of other suitable thickness.

Slices can be generated using a microtome system, freehand sectioning, tissue slicers for submerged samples, tissue dissociation systems, and/or other techniques.

For cell or nuclei suspensions, chosen sample thickness can improve recovery rate of tagged nuclei targets (e.g., percent of nuclei targets mapped in comparison to actual number of nuclei targets), based upon exposure of nuclei, ability to separate samples from functionalized particles at a substrate, or other factors. Additionally or alternatively, samples can be sandwiched between different substrates with functionalized particles, in order to improve recovery rate of tagged nuclei targets using the distribution of functionalized particles. Recovery rate of nuclei targets can additionally or alternatively be improved by implementation of magnetic functionalized particles (e.g., which can be applied to samples with force, injected into samples, or otherwise used), where magnetic retrieval after target tagging can result in improved recovery rates. Functionalized particles (e.g., magnetic functionalized particles) can implement antibodies configured against nuclear membrane components, to further enhance interactions with nuclei targets and improve recovery rates. Sample processing can further include use of electroporation (e.g., application of an electric field) or membrane permeabilization techniques when samples are in contact with functionalized particles, in order to increase access to nuclei for tagging of nuclei targets for mapping (in addition to cytoplasmic targets). Viral vectors can also be used in order to deliver tagging probes for nuclei targets. Additionally or alternatively, handshake sequences include single stranded oligonucleotides, which can effectively diffuse into or toward nuclei more efficiently than double stranded oligonucleotides. Additionally or alternatively, functionalized molecules can include or be coupled to lipophilic or amphiphilic moieties that enhance passing membranes (e.g., cell membranes, nuclear membranes) for interacting with such targets.

In embodiments involving sandwiching of samples between two substrates, in order to tag targets at both sides of the sample, one or both substrates can include features that allow reagents to access interior sample portions during sample processing. In variations, one or both substrates can be composed of a porous material (e.g., porous glass) that allows reagents to cross the substrates) to interior sample portions. Additionally or alternatively, in variations, reagents can be stored within bodies of functionalized particles (e.g., as vesicles), where controlled release of such reagents in response to a trigger (e.g., chemical stimulus, mechanical stimulus, light stimulus, pH stimulus, temperature stimulus, etc.) allows reagents to access interior sample portions. Additionally or alternatively, bodies of particles (e.g., the functionalized particles, particles positioned among the functionalized particles and configured to be sacrificial) can be controllably degraded in response to a trigger (e.g., chemical stimulus, mechanical stimulus, light stimulus, pH stimulus, temperature stimulus, etc.), in order to allow reagent penetration through spaces created upon degradation, to interior sample portions.

Samples can be further processed to efficiently isolate nuclei of a sample (before and/or after spatial tagging of nuclei). In specific examples, nuclei isolation efficiency can be achieved using improved buffer compositions, using mechanical shearing of tissue to expose nuclei, using photocleaving parameters to improve nuclei tagging efficiency, and/or other nuclei isolation mechanisms. For instance, nuclei can be coupled to buoyant particles (e.g., microbubbles) functionalized to bind to/tagging nuclei, which can be retrieved by buoyancy-based separation (e.g., nuclei bound to such buoyant particles float and are thus isolated from other sample components). Additionally or alternatively, nuclei can be coupled to magnetic particles (e.g., magnetic microparticles, magnetic nanoparticles, etc.) functionalized to bind to/tag nuclei, which can be retrieved by magnetic-based separation (e.g., nuclei bound to such magnetic particles are isolatable from other sample components upon application of a magnetic field).

Samples can further be processed in other suitable manners prior to interactions with the system. For instance, sample processing can include one or more of: preserving sample material (e.g., through freezing, through fixing, through embedding, etc.), lysing sampling material, washing sample material, inducing cell/tissue swelling/expansion or shrinking (e.g., through hypertonic/hypotonic solutions), inducing cell/tissue gelling, clarifying cells/tissues (e.g., using lipid clarification), and/or other suitable processing steps. In relation to mapping of nuclei, sample processing can include freezing of nuclei (e.g., in suspension, in a layer), followed by application onto a substrate with functionalized particles, and optionally, sealing of the nuclei sample at the substrate with a membrane or material (e.g., gel material).

In order to facilitate nuclei isolation and recovery post-tagging with handshake sequences, a layer (e.g., of OCT compound) can be applied to the tissue to help with hydration, thereby facilitating subsequent tissue clearing, trituration, homogenization, and/or irrigation steps. As such, the method can include covering the tissue sample with a layer of optimum cutting temperature (OCT) compound between a) tagging the set of nuclei with handshake sequences of the distribution of functionalized molecules and b) isolating the set of nuclei of the tissue sample.

Alternatively, the layer (e.g., of OCT compound) can be positioned between the set of features (e.g., functionalized particles) and the sample (e.g., tissue sample) to facilitate ease of sample dissociation (e.g., with various sample thicknesses, such as 5 micron thicknesses, 10 micron thicknesses, 20 micron thicknesses, etc.).

Polyacrylamide can be used as a coating (e.g., over feature surfaces, over sample surfaces) to improve nuclei dissociation robustness.

In order to improve recovery and/or loss of targets, samples can be gently fixed, in order to reduce stickiness and support ease of peeling a sample from a substrate with functionalized particles, for further processing. Further processing can include using a device to further expose nuclei in order to improve recovery rate of nuclei targets, where such a device can homogenize samples in a manner that preserves and enables separation of nuclei (e.g., with nuclei targets tagged using functionalized particles described below) for further characterization and mapping.

In relation to frozen sample material, the methods can include freezing of sample material in a manner that lyses cell membranes and/or other sample structures. Alternatively, the methods can include freezing of sample material in a manner that preserves cell membranes and/or other sample structures. For instance, freezing in a preserving manner can implement one or more of: rapid freezing (e.g., in liquid nitrogen, in another freezing medium, at another freezing temperature); nucleating proteins, low molecular weight solutes, saccharides (e.g., glucose), or other compounds that draw water from cells (thereby reducing the amount of water turned to ice and reducing volumetric expansion during freezing); and/or other anti-freeze compounds, in order to implement the method without lysis or structural compromise (e.g., with respect to characterizing surface target analytes without disrupting original structures, etc.). Affecting the nature of sample freezing can further affect water volume and/or analyte concentration during sample processing.

In variations, tagged targets can be processed and observed upon harvesting such target analytes and/or their derivatives after they have interacted with embodiments, variations, and examples of the system(s) and support structure(s) described above. Additionally or alternatively, the method can implement steps for observing and mapping locations of target analytes in space without harvesting of target analytes or derivatives from host tissues, cells, or other host material.

In some non-limiting examples, sample material from which targets can be tagged and processed according to embodiments of the methods can include natural tissue including one or more of: nervous system biological material (e.g., brain tissue, spinal cord tissue, nerve tissue, etc.) spanning single or multiple layers (e.g., cortical layers) of tissue and/or in relation to different types of neurons (e.g., excitatory neurons, inhibitory neurons), lymphatic system biological material (e.g., spleen tissue, lymph material, tonsil tissue, etc.) spanning zone 1, zone 2, and/or zone 3 tissue, cardiovascular system biological material, integumentary system biological material, skeletal system biological material, muscular system biological material, respiratory system biological material, digestive system biological material, endocrine system biological material, urinary system biological material, and reproductive system biological material. Additionally or alternatively, sample material can include plant tissue material, fungal tissue material, or other material. Cellular material can be associated with normal and diseased states, including one or more of: cancer cells, circulating tumor cells, metastatic cells, benign cells, or any combination thereof. In embodiments, the sample can include solid/contiguous tissue material obtained from a subject.

Sample material can include material from most-all eukaryotic organisms. In examples, sample material can include mouse tissue (e.g., brain tissue, spleen tissue, liver tissue, embryo tissue, kidney tissue, etc.). In examples, sample material can include human tissue (e.g., melanoma tissue, breast cancer tissue, brain tissue, etc.). Tissue can be derived from other multicellular organisms. Exemplary multicellular organisms include, but are not limited to a mammal, plant, algae, nematode, insect, fish, reptile, amphibian, fungi or *Plasmodium falciparum*. The tissue can be freshly excised from an organism, or it may have been previously preserved for example by freezing, embedding in a material such as paraffin (e.g. formalin fixed paraffin embedded samples (FFPE)), formalin fixation, infiltration, dehydration or the like. Optionally, a tissue section can be cryosectioned. As a further option, a tissue can be permeabilized to allow nuclei to be accessible by spatial barcode nucleic acids. As used herein, the term "tissue" is intended to mean an aggregation of cells, and, optionally, intercellular matter. Exemplary tissue types include muscle, nerve, epidermal and connective tissues. Tissues can also be from a diseased subject, such as but not limited to an autoimmune disease or cancer (e.g., a tissue from irritable bowel disease (IBD) or MS, or a tumor tissue).

In some non-limiting examples, sample material from which targets can be tagged and processed according to the methods described can include synthetic tissue including cell-seeded scaffolds or other composite material.

Receiving the sample at the substrate can additionally or alternatively include implementing one or more structures for retention of the sample in position relative to the functionalized particles, where, in examples, structures can include substrates (e.g., substrates patterned with the distribution of functionalized particles), microwells, microarrays (e.g., with nucleic acids capturing particles), scaffolds, or other 2D/3D structures. Additionally or alternatively, one or more of the sample and the functionalized particles can be retained in position by use of forces (e.g., magnetic forces, electrical forces/charged surfaces, gravitational forces, forces applied using acoustic or other vibration, centrifugal forces, buoyancy forces, chemical binding, etc.). In such variations, retention can be reversed by releasing retained functionalized particles from a support structure or substrate by one or more of: application of magnetic forces of reverse polarity or removal of a magnetic field (e.g., for functionalized magnetic particles), application of reverse polarity charge or other removal of electrical forces, removal of gravitational forces, removal of forces applied using acoustic or other vibration, application of a detergent to remove chemical bonds, and/or other suitable mechanisms. As such, retention and release of a sample from a substrate can be performed in a reversible or non-reversible manner (e.g., to facilitate enzymatic reactions at the substrate and/or within a process container after transfer of the substrate to the process container).

Figure 8:
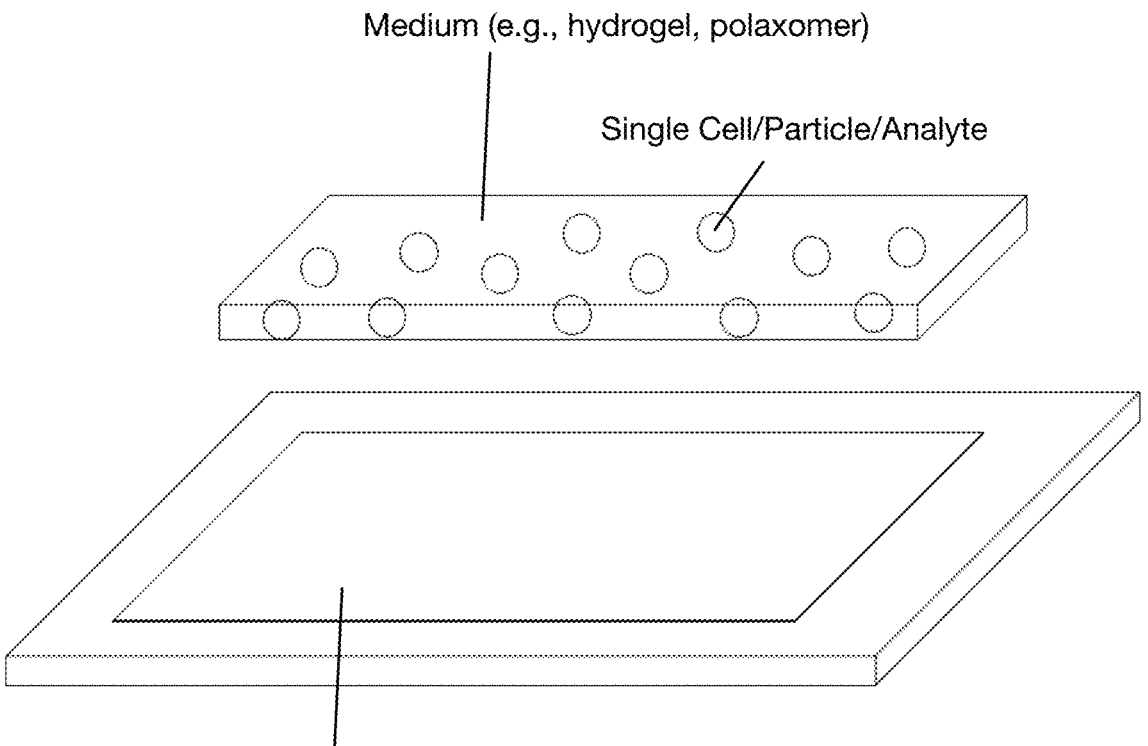
FIG. 8 depicts an example of processing steps associated with characterizing a distribution of single cells/particles/analytes dispersed across a medium or scaffold.

As shown in FIG. 8, a variation of receiving the sample at the substrate can include receiving a composite sample, including a distribution of single cells (or alternatively, single particles, single, analytes, etc.) distributed within or across a medium (e.g., hydrogel medium, polaxomer medium), at the substrate, and performing embodiments, variations, and examples, of the method(s) described accordingly. Such a variation can thus enable single-cell or single particle spatial multi-omics without droplet-based or microwell-based systems, thereby producing shorter hands on time and/or less complex single-particle processing apparatus. Furthermore, such a variation can implement various substrate sizes in order to overcome doublet, triplet, quadruplet, etc. rates and increase throughput.

Additionally or alternatively, promoting interactions between functionalized particles of the system and a sample can include infusing functionalized particles and/or a system unit into or onto a sample (e.g., into a tissue, into an organ, etc.). Examples of infusion can include one or more of: injection, electroporation, use of vectors (e.g., viral vectors), and other infusion methods. Additionally or alternatively, Additionally or alternatively, promoting interactions between functionalized particles of the system and a sample can include coupling functionalized particles to a surface of a sample/specimen (e.g., by chemical binding, by magnetic binding, by other binding).

Additionally or alternatively, during use, and in an application of use involving spatial characterization of target analytes in 3D, stacks of substrates with distributions of functionalized particles can be implemented (e.g., with layering of samples/slices of tissue and units of the system 100, with disassembly of sample into sub-portions and interacting sub-portions with various substrates). As such, the system 100 can include additional substrates with distributions of functionalized particles (e.g., a second substrate with a second distribution of functionalized particles, a third substrate with a third distribution of functionalized particles, etc.), with layering or re-assembly of sample pieces and reconstruction of 3D volumes by stitching data derived from implementation of the various substrates.

Additionally or alternatively, during use, and in an application of use involving spatial characterization of target analytes in 3D, methods described can include applying units of the system 100 to a set of sides of a sample (e.g., block of tissue), followed by promoting interactions between the sample and functionalized particles of each unit of the system 100, and reconstructing 2D surfaces and/or 3D volumes by stitching data derived from implementation of the substrates of the units of the system 100. In variations, application of units of the system 100 to a set of sides of the sample can include providing a support structure 200 configured to fold about the set of sides of the sample (e.g., with an origami structure that folds to apply units of the substrate 110 to the set of sides of the sample, and unfolds to release the sample, etc.). Additionally or alternatively, the support structure 200 can be constructed with a shape memory material that responds to environmental conditions (e.g., temperature, electric field, pH, etc.) and adjusts morphology to contact the set of sides of the sample, and/or responds to environmental conditions (e.g., temperature, electric field, pH, etc.) and adjusts morphology to displace units of the system 100 from the set of sides of the sample (e.g., to release the sample for further processing). Such elements and configurations can thus be used to generate spatial distributions of targets of a sample, for samples that have a low level of rigidity. In examples, such tissues can have a Young's Modulus less than 50 kPa, less than 40 kPa, less than 30 kPa, 20 kPa, less than 15 kPa, less than 10 kPa, less than 9 kPa, less than 8 kPa, less than 7 kPa, less than 6 kPa, less than 5 kPa, less than 4 kPa, less than 3 kPa, less than 2 kPa, less than 1 kPa, or other suitable values. Additionally or alternatively, such elements and configurations can be used to generate spatial distributions of targets of a sample, for samples that have a high level of rigidity. In examples, such tissues can have a Young's Modulus greater than 50 kPa, greater than 100 kPa, greater than 1 MPa, greater than 50 MPa, greater than 100 MPa, greater than 500 MPa, greater than 1 GPa, greater than 10 GPa, greater than 20 GPa, greater than 30 GPa, greater than 40 GPa, greater than 50 GPa, greater than 60 GPa, greater than 70 GPa, greater than 80 GPa, greater than 90 GPa, greater than 100 GPa, or other suitable values.

Additionally or alternatively, the method can implement mapping molecules (e.g., delivered using a viral library encoding a diverse collection of RNA sequences) that interact with corresponding sample targets of the sample (e.g., through interactions with exposed target projection regions of the sample), and tracking the mapping molecules (e.g., through downstream sequencing processes) upon promoting an interaction between the sample and a unit of the system described above.

Additionally or alternatively, the method can implement structures (e.g., mesh structures with affinity molecules, mesh structures with primer-like sequences, etc.) positioned in proximity to a sample, where target analytes transfer to the structures during sample processing, and are subsequently processed using a unit of the system described above (e.g., by promoting interactions between the mesh structure and the unit of the system).

In variations, the methods described can include returning outputs. In example applications, returning outputs can include one or more of: returning an output characterizing a stage of cancer (e.g., upon identifying a set of cancer genes and/or spatial distributions thereof) associated with the sample; returning an output characterizing a somatic mutation associated with the sample; returning an output characterizing an immune response associated with the sample; returning an output characterizing a stage of biological development (e.g., development stage associated with clustering of mRNAs, etc.) associated with the sample; returning an output characterizing a pathological state (e.g., associated with liver disease, associated with kidney disease, associated with a neurological disease, associated with another disease state, performing diagnostics without whole transcriptome assessment etc.) associated with the sample; returning an output characterizing a spatial characteristics of a whole transcriptome associated with the sample; returning outputs characterizing gene expression of a targeted set of genes; returning outputs characterizing protein expression (e.g., via oligonucleotide-conjugated antibodies), returning outputs characterizing nucleosomal positioning (e.g., with ATAC-seq), returning outputs characterizing methylation sequences, returning outputs characterizing chromatin structure (e.g., with characterization of open chromatin, with characterization of chromatin accessibility, etc.), returning outputs characterizing transcription factor binding, returning outputs characterizing genomic features (e.g., mutations, copy number variations, etc.), and/or returning other suitable outputs.

As described, spatial characterizations can be performed in 2D and/or 3D (e.g., with 3D structures and/or layering of system units with sample slices, etc.). Furthermore, a set of samples can be processed for a set of subjects/patients in parallel, using different subject/patient barcodes (e.g., molecular barcodes) in a manner that allows for decoding of characterizations corresponding to respective subjects/patients in an efficient manner.

Additional method aspects are described as follows:
3.1 Method—Target Tagging (e.g., Nuclei/Cell Tagging)

As shown in FIG. 7C, step S510 recites: generating a set of labelled cells, upon tagging a set of cells with a first set of oligonucleotides. Relatedly, as shown in FIG. 7D, step S610 recites: generating a set of labelled nuclei, upon tagging a set of nuclei with a first set of oligonucleotides. Generating the set of labeled cells and/or labelled nuclei functions to associate (e.g., hybridize, otherwise associate) tagging oligonucleotides with nucleic acids of nearby cells/nuclei, thereby tagging them in a manner that allows for spatial identification of positions of the cells/nuclei with execution of further processing and sequencing operations described in more detail below.

In one embodiment, as shown in FIG. 7A, labelling can involve: processing a sample comprising a set of targets (e.g., nuclei, cells) with a substrate comprising a distribution of tagging molecules comprising spatial sequences S410; tagging the set of targets with the distribution of tagging molecules (e.g., upon cleaving functionalized molecules of the distribution of spatial sequences for delivery toward the set of targets) S420; isolating targets (e.g., nuclei, cells) of the set of targets of the sample S430; and determining positions of targets of the set of targets upon sequencing molecules generated from the distribution of tagging molecules S440, where the positions are then mapped to spatially characterize the position(s) of all isolated and processed nuclei in space.

In relation to step S410, embodiments, variations, and examples of substrates comprising a distribution of tagging molecules comprising spatial sequences are described above in Section 2. One such embodiment of a substrate comprises a distribution of functionalized particles to which tagging oligonucleotides are coupled with cleavable linkers, where each functionalized particle comprises tagging oligonucleotides that comprise spatial sequences corresponding to positions of the respective functionalized particles, and tagging/handshake sequences that interact with sample targets (e.g., nuclei, cells) upon delivery to proximal sample targets. Variations of the substrate can include tagging oligonucleotides that are spatially distributed, but are not coupled to functionalized particles. For instance, tagging oligonucleotides can be distributed across features of a substrate (e.g., slide), where the features can include spots, pits, wells, pillars, or other features to which tagging oligonucleotides are coupled by cleavable linkers.

Step S410 can include contacting a biological specimen (i.e., a cryosectioned tissue sample) with a unit of the system 100, 200 described, where the identity and location of the each barcode corresponding to a feature on the substrate can be decoded prior to contacting the biological specimen with the system. In variations, the spatial sequences comprise stochastic barcode sequences, where the positions of the stochastic barcode sequences are decoded to generate coordinate positions of each stochastic barcode sequence prior to contacting a sample with the distribution of functionalized particles. In variations, the tagging sequences can comprise tagging sequences (e.g., ligation sequences, hybridization sequences, etc.) with nuclei targets and/or cellular targets (e.g., cytoplasmic targets, intracellular targets, other cellular targets, etc.).

In embodiments of Step S410, the sample can include whole tissue structures, tissue portions (e.g., histological tissue slices, formalin-fixed paraffin-embedded (FFPE) tissue, frozen tissue (e.g., fresh frozen tissue), fixed tissue, permeabilized tissue, biopsied tissues, fresh frozen plasma, seeded natural scaffolds, seeded synthetic scaffolds, etc.), organs, whole organisms, organoids, a cell suspension (e.g., frozen cell suspensions that are separated prior to processing with the system, cell suspensions retained in a medium/hydrogel medium, etc.), single cells, a nuclei suspension, organelles, sub-organelle structures, intra-organelle components, mitochondrial targets, viruses, microorganisms, and other samples.

In relation to steps S410 and S420, tagging the set of nuclei or cells with the tagging oligonucleotides can include cleaving functionalized molecules from the functionalized particles or substrate surface, where the cleaved molecules diffuse toward and interact with proximal nucleic acids of targets (e.g., nuclei targets, cell targets) of the sample. Such an embodiment allows for precise cell/nucleus location determination in downstream steps, by using tagging oligonucleotides that are initially fixed in position at a substrate and that have spatial sequences (e.g., stochastic barcode sequences, address sequences). In embodiments of tagging oligonucleotides where the spatial sequences comprise stochastic barcodes, the sequences of the stochastic barcodes and positions of the barcoded portions can be predetermined, according to embodiments, variations, and examples of sequencing techniques described above.

Tagging of nuclei or cells of the sample in step S420 can include cleaving the tagging oligonucleotides with a photo-cleaving mechanism, an enzymatic cleaving mechanism, a pH shift, mechanical separation, a thermal mechanism, or another suitable cleaving mechanism. Tagging of nuclei or cells can alternatively include delivering functionalized particles comprising spatial sequences to a sample comprising the nuclei or cells, using a magnetic field (e.g., for magnetic or paramagnetic particles), where the tagging oligonucleotides and/or functionalized particles can be retained in position and/or released, with application and/or removal of a magnetic field.

Tagging of nuclei or cells of the sample in step S420 can further include promotion of cytosolic entry or other cross-membrane conveyance for the tagging oligonucleotides, with respect to cellular membranes of the sample. As such, step S420 can include promoting cross-membrane transmission for a tagging oligonucleotide toward a nuclei of a cell of the sample, upon application of a stimulus. Step S420 can also include removal of the stimulus, or application of a second stimulus in order to reduce accessibility across a cell membrane.

Cross-membrane conveyance can involve one or more of: passive diffusion, active transport, use of vectors (e.g., viral vectors) for transmission of tagging oligonucleotides, use of cell-penetrating peptides for transmission of tagging oligonucleotides, use of protein toxins for transmission of tagging oligonucleotides transporter-mediated entry across membrane channels, and/or other suitable mechanisms. In variations, an applied stimulus for improving tagging oligonucleotide transmission toward a nucleus or cell can include one or more of: an electric field (e.g., for electroporation), a temperature reduction (e.g., for cryoporation), a temperature increase, a force that physically disrupts a membrane, an enzyme that disrupts a membrane, a chemical gradient, electromagnetic energy, or another stimulus that increases membrane permeation.

Cleaving parameters are described above.

Isolating targets (e.g., nuclei, cells) of the set of targets of the sample in Step S430 can include performing homogenization and/or trituration with a suitable buffer (e.g., isolation buffer), examples of which are described. Trituration can be performed using an aspiration and delivery device (e.g., pipettor, irrigator) or other suitable device.

Determining positions of targets of the set of targets upon sequencing molecules generated from the distribution of tagging molecules can include processing targets with a particle (e.g., cell/nucleus) processing platform that supports sequencing of targets tagged using the described handshake sequences. For instance, in embodiments where a target (e.g., nucleus, cell) is tagged using handshake molecules of functionalized particles post-cleavage, tagging of the nucleus can involve tagging the nucleus with different cleavable molecules associated with different spatial positions at the substrate.

In example embodiments, nucleic acid sequences generated using single cell/single nuclei-processing platforms can include a CBC and a UMI, and can capture more than one spatial barcode if the single target was in proximity to or overlapping more than one location on the substrate, and thus multiple handshake sequences. As such, given that multiple handshake sequences associated with different substrate positions can tag a single target, a bioinformatics approach can involve determining the position of the nucleus based upon a subset of different positions corresponding to a subset of barcodes of handshake molecules that tagged the nucleus. The position of the nucleus can be determined from an average position of the subset of stochastic barcodes (e.g., a centroid of positions of the subset of stochastic barcodes). In variations, nuclei can be tagged using a combination of cleavable and non-cleavable molecules (or molecules cleaved in different stages and in response to different stimuli), such that positions of the nuclei can be determined from stochastic/spatial barcode positions of cleavable and non-cleavable molecules (e.g., as a weighted centroid of positions, where positions of non-cleavable components are weighted more heavily than positions of cleavable components). As such, the position estimated from the barcodes serving as spatial addresses can be an estimation of the location in or on a sample, in or on a feature (e.g., functionalized particle) or a combination thereof.

In an example, DBSCAN can be applied to distinguish "signal" barcodes (e.g., sequenced barcodes that are likely to provide value in positioning nuclei) from background "noise" barcodes (e.g., sequenced barcodes that are likely to confound nuclei positioning). Application of DBSCAN can output a cluster assignment for each sequenced barcode that serves as a spatial address, where Cluster=0 denotes noise barcodes, and cluster >0 denotes signal barcodes grouped with other signal barcodes that cluster in space. Spatial positions with all spatial barcodes denoted noise are not assigned to targets (e.g., nuclei, cells), or assigned to targets (e.g., nuclei,cells) with multiple signal clusters. From the remaining targets with one distinct spatial barcode signal cluster, a weighted centroid of spatial barcode coordinates in the signal cluster is taken, where weights are the number of unique molecular identifiers (UMIs) for sequenced barcodes. Importantly, DBSCAN requires two parameters: minPts and eps (effectively, radius). To determine the optimal parameter set for each run, 15 different minPts parameters are iterated through, and the parameter set with the highest proportion of targets that are assigned a spatial position is chosen (i.e., one DBSCAN signal cluster). While DBSCAN can position targets with relatively high sensitivity and specificity, alternative approaches for positioning can include: assigning a target (e.g., nucleus, cell) the position of its highest UMI spatial barcode, taking a weighted 2-dimensional median of spatial barcode coordinates, K-means clustering, Affinity propagation, Mean Shift, Spectral Clustering, Agglomerative Clustering, DBSCAN extensions such as HDBSCAN and OPTICS, and/or other methods.

Counting UMIs can also support determination of nuclei/ cell positions. The computational methods can use the distance on the substrate of the different handshake sequence barcodes associated with a target upon sequencing. If the different handshake sequence barcodes are close on the substrate, the location of the target is most likely somewhere in between or overlapping the locations. If the different handshake sequence barcodes are far way, then it is likely that the spatial barcode nucleic acids diffused away from their location and the location is the spatial barcode with the most UMIs because the spatial barcode with higher UMIs was the predominant spatial barcode that diffused into that single cell.

Determined positions can then be used for generating a spatial map of the distribution of nuclei from the set of spatial positions.

3.1.1 First Example of Target Tagging and Isolation-Nuclei/ Cells

In a specific example of step S420, tagging the set of nuclei or cells with the tagging oligonucleotides can include:

0. Preparing materials, which can include: equilibrating a fresh frozen tissue sample and optimal cutting temperature (OCT) compound to −18° C. in a cryostat for at least 20 minutes prior to sectioning. The optimal temperature for sectioning may vary depending on the tissue type. Preparing materials can also including reducing temperature of a centrifuge involved in the procedure (e.g., to 4° C.) and inserting suitable swing bucket accessories for containers (e.g., 1.5 mL tubes) used in the procedure. Preparing materials can also include providing ice and chilling a multi-well container (e.g., a 12-well plate on ice) to reduce the temperature of the multi-well container. Preparing materials can also include reducing the temperature of straining apparatus (e.g., cell strainers) to low temperature (e.g., −20° C., 0° C., below 0° C.). Preparing materials can also include preparing Crystal Violet, if used for tissue staining, to make a solution (e.g., a 25% solution) by dissolving the Crystal Violet in a volume (e.g., 4 mL) of nuclease-free water. Preparing materials can also include preparing a cleavage buffer and storing the cleavage buffer on ice. In an example, the cleavage buffer can be configured for cleavage with a photocleaving mechanism (as described below). The cleavage buffer can comprise a wash buffer with a dye (e.g., 4% Trypan Blue, 0.01% Trypan Blue, etc.). Preparing materials can also include preparing isolation buffer for isolation of nuclei of the sample post-tagging of nuclei of the sample, and storing the isolation buffer on ice. In variations, the isolation buffer can include a combination of nuclei-isolation reagents and RNAse inhibitor. Preparing materials can also include preparing a wash buffer and storing the wash buffer on ice, where the wash buffer can include a combination of storage buffer, bovine serum albumin (BSA), and RNAse inhibitor.

1. Preparing a section of a tissue sample (e.g., fresh frozen tissue sample cryo-sectioned to 20 μm at −18° C.), where variations of section thicknesses and preparation methods are described. When working with a tissue block that is larger than the area of the distribution of functionalized particles/features the substrate, preparing the second of the tissue sample can include, using a square tissue punch to define the desired capture area and optionally further cutting the tissue sample (e.g., using a razor blade to score the borders). If the tissue block was previously stored in the freezer or cryostat for extended periods, it is recommended to section 50-100 μm into the block prior to taking a 20 μm section. Additionally, to protect a sectioned/exposes surface of the tissue block between instances of cutting sections from the tissue block, it is recommended to cover the sectioned/exposed surface of the tissue block with OCT compound. Tissue sample quality can be assessed with respect to RNA quality by collecting one or more sections (e.g., 10 μm sections) of the tissue sample and isolating RNA with an RNA extraction kit, followed by analysis of the RNA to derive a RNA integrity number (RIN). The RIN should have a value greater than a threshold value (e.g., a RIN value of at least 7, a RIN value of at least 8, etc.). Additionally or alternatively, tissue sample quality assessment can involve performance of staining (e.g., H&E staining) on an adjacent section of the tissue sample in order to provide information on tissue structural context and sectioning quality.

2. Contact the tissue section with the distribution of functionalized particles/features at the substrate.

A first option for precise placement of the region of interest includes: placing the substrate with the distribution of functionalized particles in the cryostat to reduce temperature (e.g., for 1 minute), followed by placing the chilled substrate with the distribution of functionalized particles on the cutting stage. Contacting the tissue section with the distribution of functionalized particles can then include arranging the tissue section on top of the substrate using a brush, ensuring that the region of interest is positioned directly over the distribution of functionalized particles. Then, with the substrate and tissue section facing upward, melting the tissue section onto the substrate by moving the substrate off the cryostat stage, and gently placing a finger on the bottom of the substrate. To avoid curling of the tissue section, warming the tissue section can be performed directionally from one edge of the section to another edge of the section (e.g., rather than warming the section from the center). A small brush can be used to hold the other edge of the tissue flat during the initial melting from one end. Do not lift the edges of the substrate off of the flexible film supporting the substrate, while melting the tissue.

A second option for quick placement of the region of interest includes: holding a room temperature substrate with functionalized particles in the support structure with the flexible film, with the distribution of functionalized particles facing downward. Contacting the tissue section can then include hovering the substrate over the region of interest and gently lowering the substrate to bring it into contact with the tissue section. With the second option, the substrate with the tissue section can then be placed back into the cryostat.

When experiencing difficulties in tissue application due to static charge, one can perform one or more of: grounding oneself before sectioning, changing to a new pair of gloves, wiping the back of the flexible film with 100% ethanol followed by drying, cleaning of the entire cryostat chamber with 100% ethanol to reduce charge, placing a piece of a dryer sheet in the corner of the cryostat, and performing other suitable actions to reduce or eliminate static charge that could disrupt tissue application.

3. Prepare the tissue section for storage and/or stimulus-mediated cleavage of functionalized particles. Following step 2 described above, if a masking element (e.g., sticker described above) was used (e.g., at the backside of the substrate), one can remove the masking element prior to removing the substrate from the flexible film. Tweezers or other tools can be used to remove the substrate from the flexible film, followed by placing the substrate within a well of the multi-well plate prepared on ice and described in Step 0. Preparing the tissue section can then involve dispensing (e.g., immediately pipetting) cleavage buffer prepared in step 0 (e.g., 30 μL of cleavages buffer) onto the substrate with the tissue section, ensuring that the entire tissue section is covered in buffer. Then, the multi-well plate and/or substrate can be tilted to spread the buffer over the entire tissue section.

4. Cleave functionalized molecules from the particles/features of the substrate, to release them toward targets (e.g., nuclei, cells) of the sample. Cleaving can include positioning an ultraviolet (UV) light over (e.g., 1-2 centimeters) above the multi-well plate prepared in step 3, ensuring that the UV meter of the UV light is set to a desired current limit (1.2 A) and desired power setting. Then, cleaving can include transitioning the UV light to an on state, and exposing the substrate with the tissue section to UV light for a duration of time (e.g., 30 seconds, 60 seconds), while keeping the multi-well plate on ice. However, other power settings, wavelengths of light, and exposure times can be used, depending upon the structure(s) of the functionalized molecules of the substrate. In coordination with cleaving, step 4 can then include incubating the substrate at low temperature (e.g., on ice) for a duration of time (e.g., 7.5 minutes, 5 minutes, 2.5 minutes, another suitable or intermediate duration of time), prior to tissue clearing and dissociation in workflow operations 5 and 6 described below. Adjusting incubation time can improve accuracy of spatial positioning of nuclei in subsequent workflow operation steps. Cleaving thus releases handshake sequences of the functionalized particles for interactions with nuclei/cells/other targets of the tissue sample.

5. Clear the tissue section from the substrate. After incubation in step 4, clearing the tissue section can include dispensing a volume (e.g., 200 μL) of a lysis buffer with RNase inhibitor onto the distribution of functionalized particles at the substrate, aiming at the tissue sample. Dispensing the volume of lysis buffer with RNase inhibitor can be repeated several times (e.g., 4 times for a total of 1 mL dispensed). Dispensing can include aiming at different regions of the distribution of functionalized particles in order to detach entire tissue section from the substrate. Clearing the tissue section can further include continuing to dissociate the tissue from the substrate by aspirating dispensed buffer still contained within the well, and dispensing it onto the regions of distribution of functionalized particles covered by tissue, keeping the multi-well plate on ice as much as possible. Visual inspection (e.g., using a microscope) can be performed to determine if any tissue remains covering the substrate/distribution of functionalized particles, followed by further aspiration and dispensing of buffer to further remove tissue from the substrate. Clearing the tissue in step 5 can then include transferring the substrate to an empty container (e.g., empty well of a multi-well plate), with care not to scratch the substrate to dislodge functionalized particles into the solution with the cleared tissue. In particular, contamination of functionalized particles can cause issues in downstream single nuclei tagging steps.

6. Dissociate nuclei. Dissociating nuclei can include mechanically dissociating nuclei by way of trituration (e.g., with repeated aspiration and delivery of the nuclei suspension generated from the cleared tissue). Multiple trituration steps can be performed with rest periods between instances of trituration. Dissociating nuclei can include observing (e.g., under a microscope) that the nuclei suspension comprises primarily single nuclei. If tissue chunks remain, additional trituration steps can be performed. Dissociating nuclei can then include dispensing a volume (e.g., 1 mL) of wash buffer with RNase Inhibitor to the nuclei suspension, followed by pipet mixing of the nuclei suspension with the wash buffer and RNase inhibitor and transfer of well contents into one or more centrifuge containers. Dissociating nuclei can then include spinning the one or more centrifuge containers within the pre-chilled centrifuge with spin buckets set to 4 degrees C. (e.g., at 500×g for 5 minutes). Following centrifugation, dissociating nuclei can then include carefully removing the centrifuge containers from the centrifuge and placing them immediately on ice. Dissociating nuclei can include removing the supernatant, being careful not to disturb the pellet. The pellet of nuclei can then be resuspended in a volume (e.g., 1 mL) of Storage Buffer with RNase inhibitor. The resuspension can then be mixed, followed by filtering of the nuclei suspension through a pre-chilled strainer (e.g., pluriStrainer Mini™ 20 μm cell strainer) into an unused centrifuge container. The filtered sample can then be centrifuged (e.g., at 500×g for 5 minutes set to 4 degrees C.), followed by removal of the centrifuge container from the centrifuge and placement of the centrifuge container on ice. The nuclei suspension can then be processed for nuclei counting (e.g., with reservation of a portion of buffer, such as 50 μL of buffer).

7. Nuclei Counting. If performing snRNA-seq with single cell scanner free workflows, nuclei can be counted with AOPI or Ethidium Homodimer-1 with dilution of the nuclei to the desired concentration based on the manufacturer's guidelines. If performing snRNA-seq with a scanner workflow, nuclei can be counted with DyeCycle green. Counting with a fluorescent automated counter or microscope is strongly recommended and the use of Trypan Blue can lead to overestimated nuclei counts. Count nuclei in replicates (2-3 reproducible counts) to ensure accuracy.

7B. (Optional) Evaluation of tissue dissociation completeness. Evaluation can including staining of the substrate that initially had the distribution of funcitonalized particles, post nuclei isolation to assess the completeness of the tissue dissociation. Evaluation can guide determinations of whether to proceed to scRNA-seq according to step 8. In one example, evaluation of tissue dissociation can include: positioning the substrate from step 5 onto a wipe (e.g., absorbent wipe) so that the side with the functionalized particles faces upward. Then, evaluation can include exposing the substrate to a volume (e.g., 75 ul) of dye (e.g., Trypan Blue) and incubating the substrate at room temperature for a period of time (e.g., 5 minutes, more than 5 minutes, less than 5 minutes). Evaluation can then include washing the substrate (e.g., with a 1×PBS wash solution) to wash, with removal of excess liquid from the substrate while being careful to not contact the distribution of functionalized particles. Leftover tissue at the substrate will be stained (e.g., dark blue, for Trypan blue-based evaluation. Remaining functionalized particles will also be stained (e.g., a lighter shade of blue, for Trypan blue-based evaluation).

8. Proceed to single nuclei capture and processing using a single particle (e.g., single cell, single nuclei) capture and processing platform. Single nuclei capture and processing can include performing single nuclei RNA sequencing with suitable library preparation steps (e.g., for whole transcriptome analysis, for AbSeq, etc.), amplification with suitable numbers of amplification cycles (or isothermal amplification processes), In relation to the specific example described above in Section 4.1.1, the steps of the procedure can be performed in at low temperature (e.g., at 0 C, at 4 C, etc.). For instance, the entire procedure can involve manipulating and handling materials using ice, as much as possible, where buffers, tissues, and nuclei suspensions are kept on ice as much as possible. Additionally, with respect to the specific example, the procedure can be performed rapidly followed by immediate single nuclei isolation for single nucleus RNA-seq (snRNA-seq) in order to preserve nuclei quality.

Variations of the method described above can be adapted to single cell tagging with handshake sequences, followed by processing (e.g., with a single cell processing protocol).

9. Sequencing. Sequencing of resultant snRNA-seq libraries can be performed according to the manufacturer's instructions for the chosen single cell RNA-seq platform. Sequencing of resultant snRNA-seq libraries can be performed to generate a number of read pairs (e.g., at least 5,000 read pairs. at least 10,000 read pairs, at least 20,000 read pairs, etc.) per nucleus captured. Exemplary read lengths can be from 12-50 or more reads long.

10. Bioinformatics. Performing bioinformatic pipeline analysis, for spatially mapping nuclei positions based upon sequencing performed in the above step, can be performed. Positions of tagged single nuclei can be determined and subsequently mapped using centroid approaches or other approaches, as described above, where centroids of barcodes serving as spatial addresses are used to approximate positions of each nuclei isolated, and the positions of the corresponding nuclei are then mapped. Variations of position determination are described above (e.g., with respect to DBSCAN, etc.).

Variations of the above example provided in Section 3.1.1 can include modifications, alone or in combination. For instance:

In relation to workflow operation 1, a tissue section being processed can have a different thickness (e.g., a thickness described, a thickness from 25-30 micrometers) to facilitate dissociation in workflow operations 5 and 6 and to increase nuclei yield as determined in workflow item 7, etc.

Adding a layer (e.g., of optimal cutting temperature (OCT) compound, of a hydrogel, of another hydrating material) that has suitable thickness (e.g., 5 microns, 10 microns, 15 microns, 20 microns, etc.) between the tissue section and functionalized particles/features at the substrate in workflow operation 2, to facilitate dissociation in work-flow operations 5 and 6 and to increase nuclei yield as determined in workflow item 7, etc. During operation, the layer can be kept cold (e.g., by positioning the substrate on ice, by using a coolant, etc.).

Adding a layer (e.g., of optimal cutting temperature (OCT) compound, of a hydrogel, of another hydrating material) that has suitable thickness (e.g., 5 microns, 10 microns, 15 microns, 20 microns, 35 microns, 30 microns, 35 microns, etc.) on top of the tissue section in relation to workflow operation 3, in order to limit diffusion and increase signal-to-noise ratios of generated single nucleus/single cell libraries in relation to workflow operation 9. Adding a layer can further facilitate freezing, storing, and thawing of the tissue sample at the substrate at this phase (e.g., in order to facilitate batch processing of multiple substrates), in order to provide a more flexible workflow (e.g., if an operator is not near a cryostat, etc.).

Adding a wash step after UV exposure (e.g., immediately after UV exposure) in relation to workflow operation 4, in order to remove released functionalized molecules that did not get absorbed by the tissue section, in order to reduce noise and to improve the percentage of useful reads in relation to workflow operations 9 and 10. The wash step can involve a suitable wash buffer, embodiments, variations, and examples of which are described.

3.1.2 Second Example of Target Tagging and Isolation—Nuclei/Cells 1. preparing a section of a tissue sample (e.g., fresh frozen tissue sample cryo-sectioned to 20 μm at −16° C.), where variations of section thicknesses and preparation methods are described.

2. Promoting interactions between functionalized particles at a substrate and targets (e.g., single cell targets, nuclei targets) of a sample (e.g., with application of the section to a substrate to which the functionalized particles are coupled, ensuring there are no folds, with use of a brush to flatten the section at the substrate).

3. Transmitting heat to the section through the substrate, thereby melting the section at the substrate.

4. Transmitting heat away from the substrate, with the section, and covering the substrate, with the section, with a dissociation buffer. In an example, the substrate with the section is placed on ice, and 6-10 μL of dissociation buffer is placed on top of the substrate with the section. In an example, the dissociation buffer includes $Na_2SO_4$, $K_2SO_4$, Glucose, HEPES, and $MgCl_2$. In variations, the dissociation buffer can be used in coordination with dissociation of nuclei according to the first example of target tagging and isolation described above.

5. Exposing the substrate with the section under a UV light (e.g., with 365 nm emission) for a period of time (e.g., 30 seconds) in order to cleave the spatial barcode oligo-nucleotides of the functionalized particles, followed by incubating the substrate with the section at low temperature (e.g., on ice) for a duration of time (e.g., for 7.5 minutes).

6. Positioning the substrate with the section into a sample processing container (e.g., 12-well plate, other well plate, tube, channel, flow cell, container, etc.) and dispensing extraction buffer onto the substrate to release the section from the substrate (e.g., using a 200 μL pipette, 10×200 μL aliquots of extraction buffer is dispensed onto the substrate for a total volume of 2 mL. Titurations is performed with the pipette 10-15 times to release the section). In an example, the extraction buffer includes the exemplary dissociation buffer described in Step 4 above, Kollidon®, Triton X-100, bovine serum albumin, and RNase inhibitor.

7. After each round of trituration, examining the substrate (e.g., under the microscope) to confirm that the section is completely removed from the substrate. This step is repeated until the section is completely removed from the substrate.

8. Once the section is removed from the substrate, remov-ing the functionalized particles (e.g., with mechanical dis-sociation performed using a 1 mL pipette 20-25 times trituration).

9. Removing dissociated nuclei from the process con-tainer and rinsing the process container twice with 1 mL of wash buffer, which is added to the nuclei suspension. In an example, the wash buffer includes a portion of the dissocia-tion buffer described above, bovine serum albumin, and RNase inhibitor.

10. Spinning the nuclei suspension (e.g., in a pre-cooled swinging bucket centrifuge at 600 g for 10 min at 4° C.).

11. Removing the supernatant, and optionally pooling nuclei pellets from multiple centrifuge containers.

12. Filtering the nuclei suspension (e.g., using a pre-cooled 40-micron filter wetted with dissociation buffer)

13. Adding DAPI (e.g., 1:1000 DAPI) to the filtered solution and incubating it (e.g., for 8-10 minutes on ice)

14. After incubation, centrifuging the DAPI/nuclei solu-tion (e.g., at 200 g for 10 minutes at 4 C).

15. Removing the supernatant.

16. Counting the nuclei using a hemocytometer a. Comparing the Number of Nuclei Counted to a Passing Criterion (e.g., >10 k nuclei)

In variations, isolating labelled nuclei can include imple-menting automated sample homogenizers for tissue disso-ciation and nuclei isolation. Isolation of nuclei can addition-ally or alternatively involve use of affinity tagging with coupling of nuclei or cells to particles that can be separated from other sample components (e.g., by magnetic attraction, by buoyant forces, by density-based separation methods, by filtration, etc.).

Figure 9:
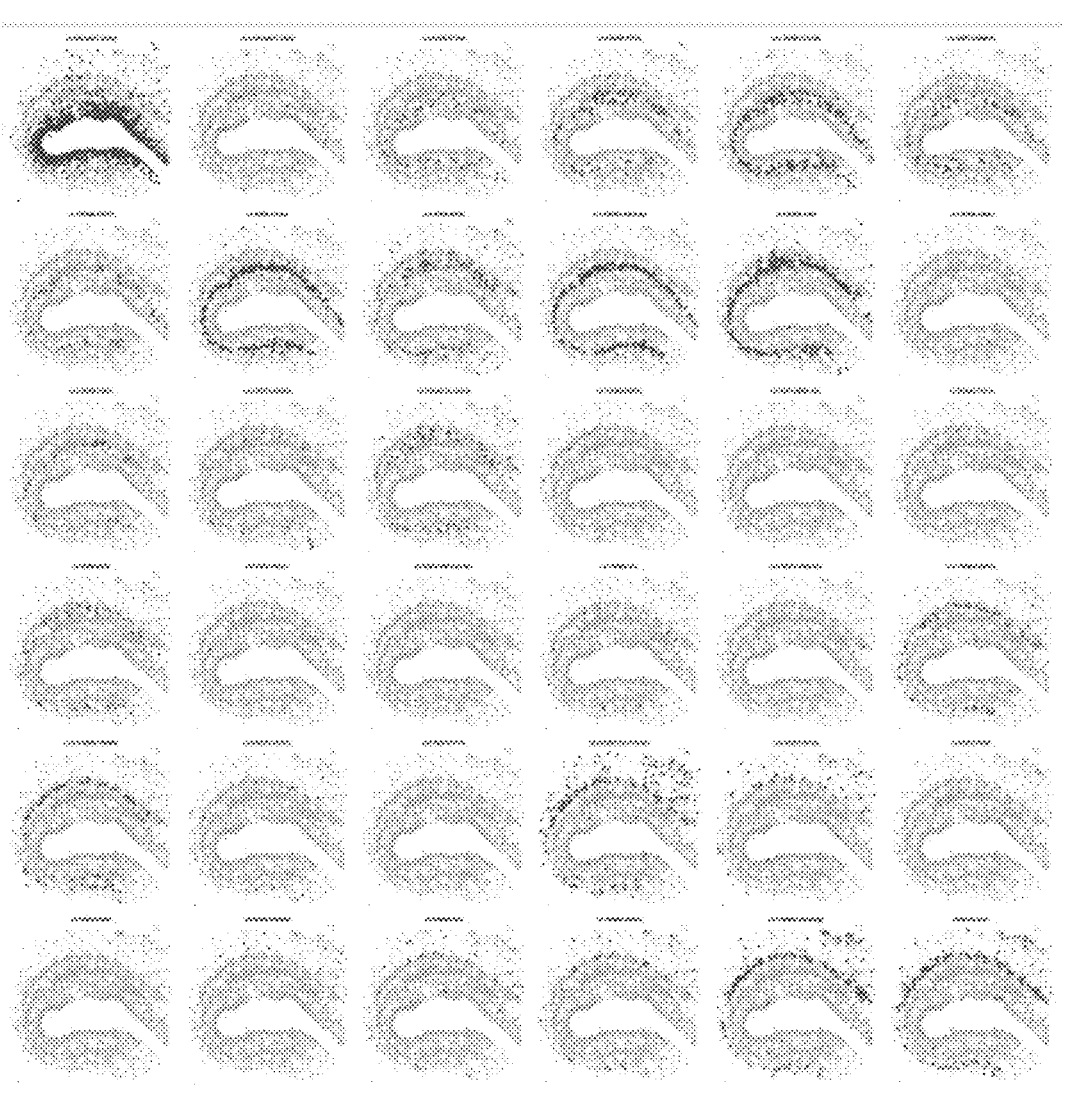
FIG. 9 illustrates exemplary maps of targets from nuclei of a sample processed with a unit of the system.

Exemplary data depicting analyses of over 52,000 nuclei from a sample of human cortex tissue, with a 10 mm×10 mm distribution of functionalized particles for spatially tagging nuclei of a sample is shown in FIG. 9. In the example shown in FIG. 9, the sample of human cortex tissue was processed with tagging of nuclei using handshake sequences, and subsequent analyses according to methods described indi-cated spatial distributions of nuclei corresponding to cell types: astrocytes, endothelial cells, excitatory neurons, inhibitory neurons, microglia, oligodendrocytes, and oligo-dendrocyte precursor cells, along with indications of distri-butions of grey matter and white matter. In the exemplary sample, Astrocytes represented 8.06% of the nuclei tagged and mapped, endothelial cells represented 5.15% of the nuclei tagged and mapped, excitatory neurons represented 15.54% of the nuclei tagged and mapped, inhibitory neurons represented 5.89% of the nuclei tagged and mapped, micro-glia represented 3.92% of the nuclei tagged and mapped, oligodendrocytes represented 35.29% of the nuclei tagged and mapped, and oligodendrocyte precursor cells represented 2.65% of the nuclei tagged and mapped, where log of UMI counts was over 3 in relation to all cell types.

3.2 Method—Spatial Segregation and Further Processing of Cells/Nuclei

Step S520 recites: seating the set of labeled cells at interstitial spaces of a distribution of functionalized particles coupled to a substrate (wherein each functionalized particle contacts no more than one labelled cell of the set of labelled cells). Step S620 recites: seating the set of labeled nuclei at interstitial spaces of a distribution of functionalized particles coupled to a substrate.

Steps S520 and S620 function to reliably capture and position sample components of interest (e.g., cells, nuclei) at a substrate, where features of the substrate simultaneously operate to spatially segregate/isolate the individual components and further tag the components with functionalized oligonucleotides, in order to further barcode the components of interest for processing (e.g., according to library preparation operations described further below).

In variations, labelled cells/nuclei generated in steps S510 and S610 can be transferred to a second substrate that has a distribution of functionalized particles, where spaces (e.g., interstitial spaces) between functionalized particles are configured to receive the cells/nuclei, and position them such that they can be labeled by functional molecules coupled the functionalized particles. In embodiments, variations, and examples, the second substrate can comprise a substrate described in U.S. patent application Ser. No. 17/895,633 filed on 25 Aug. 2022 and titled "Systems and Methods for Characterizing Locations of Target Analytes in Multi-Dimensional Space", which is herein incorporated in its entirety by this reference.

Functionalized particles of the second substrate can be coupled to the second substrate with close-packing (e.g., random close packing, rectangular close packing, hexagonal close packing, etc.) or without close packing. Spaces defined between functionalized particles can be configured to receive the cells/nuclei, and have a characteristic dimension (e.g., width, length, depth, effective diameter, etc.) of approximately 5 micrometers, approximately 6 micrometers, approximately 7 micrometers, approximately 8 micrometers, approximately 9 micrometers, approximately 10 micrometers, approximately 11 micrometers, approximately 12 micrometers, approximately 13 micrometers, approximately 14 micrometers, approximately 15 micrometers, approximately 16 micrometers, approximately 17 micrometers, approximately 18 micrometers, approximately 19 micrometers, approximately 20 micrometers, approximately 21 micrometers, approximately 22 micrometers, approximately 23 micrometers, approximately 24 micrometers, approximately 25 micrometers, approximately 26 micrometers, approximately 27 micrometers, approximately 28 micrometers, approximately 29 micrometers, approximately 30 micrometers, approximately 31 micrometers, approximately 32 micrometers, approximately 33 micrometers, approximately 34 micrometers, approximately 35 micrometers, approximately 36 micrometers, approximately 37 micrometers, approximately 38 micrometers, approximately 39 micrometers, approximately 40 micrometers, approximately 41 micrometers, approximately 42 micrometers, approximately 43 micrometers, approximately 44 micrometers, approximately 45 micrometers, approximately 46 micrometers, approximately 47 micrometers, approximately 48 micrometers, approximately 49 micrometers, approximately 50 micrometers, or another suitable dimension for reliably receiving and retaining the component of interest, in single component form, while still allowing for interactions with molecules of the functionalized particles defining the respective interstitial space.

Preferably, in relation to Steps S520 and S620, each functionalized particle contacts no more than one labelled nucleus of the set of labelled nuclei, or no more than one labeled cell of the set of labeled cells. To provide such a configuration for cell/nuclei capture and tagging at the second substrate, a suspension of cells/nuclei can be generated with a suitable number or density of components, such that delivery to the second substrate does not provide an overloaded configuration, where a functionalized particle contacts more than one nucleus or cell. In variations, Steps S520 and S620 can include counting (e.g., using a hemacytometer) the cells or nuclei, respectively, and generating a suspension including the cells or nuclei, with an appropriate buffer (e.g., nuclei lysis buffer, cell lysis buffer, other buffer). In examples, a lysis buffer can include proteinase K and DTT to a lysis buffer.

The resulting suspension can have a concentration of cells or nuclei (i.e., component), respectively, of: 1 component/microliter, 2 components/microliter, 3 components/microliter, 4 components/microliter, 5 components/microliter, 6 components/microliter, 7 components/microliter, 8 components/microliter, 9 components/microliter, 10 components/microliter, 11 components/microliter, 12 components/microliter, 13 components/microliter, 14 components/microliter, 15 components/microliter, 16 components/microliter, 17 components/microliter, 18 components/microliter, 19 components/microliter, 20 components/microliter, 21 components/microliter, 22 components/microliter, 23 components/microliter, 24 components/microliter, 25 components/microliter, 26 components/microliter, 27 components/microliter, 28 components/microliter, 29 components/microliter, 30 components/microliter, 31 components/microliter, 32 components/microliter, 33 components/microliter, 34 components/microliter, 35 components/microliter, 36 components/microliter, 37 components/microliter, 38 components/microliter, 39 components/microliter, 40 components/microliter, 41 components/microliter, 42 components/microliter, 43 components/microliter, 44 components/microliter, 45 components/microliter, 46 components/microliter, 47 components/microliter, 48 components/microliter, 49 components/microliter, 50 components/microliter, 100 components/microliter, 150 components/microliter, 200 components/microliter, 250 components/microliter, 300 components/microliter, 350 components/microliter, 400 components/microliter, 450 components/microliter, 500 components/microliter, 550 components/microliter, 600 components/microliter, 650 components/microliter, 700 components/microliter, 750 components/microliter, 800 components/microliter, 850 components/microliter, 900 components/microliter, 950 components/microliter, 1000 components/microliter, 1050 components/microliter, 1100 components/microliter, 1150 components/microliter, components/microliter, 1250 components/microliter, 1300 components/microliter, 1350 components/microliter, 1400 components/microliter, 1450 components/microliter, 1500 components/microliter, 1550 components/microliter, 1600 components/microliter, 1650 components/microliter, 1700 components/microliter, 1750 components/microliter, 1800 components/microliter, 1850 components/microliter, 1900 components/microliter, 1950 components/microliter, 2000 components/microliter, greater than 2000 components/microliter, or another suitable number of components/microliter, depending upon the number of functionalized particles provided at the second substrate.

In variations of seating the respective component(s) at the interstitial spaces, a volume of the set of cells/nuclei can be delivered to the second substrate, where the volume can be 0.5 microliters, 1 microliter, 2 microliters, 3 microliters, 4 microliters, 5 microliters, 6 microliters, 7 microliters, 8 microliters, 9 microliters, 10 microliters, 11 microliters, 12 microliters, 13 microliters, 14 microliters, 15 microliters, 16 microliters, 17 microliters, 18 microliters, 19 microliters, 20 microliters, 21 microliters, 22 microliters, 23 microliters, 24 microliters, 25 microliters, 26 microliters, 27 microliters, 28 microliters, 29 microliters, 30 microliters, 31 microliters, 32 microliters, 33 microliters, 34 microliters, 35 microliters, 36 microliters, 37 microliters, 38 microliters, 39 microliters, 40 microliters, 41 microliters, 42 microliters, 43 microliters, 44 microliters, 45 microliters, 46 microliters, 47 microliters, 48 microliters, 49 microliters, 50 microliters, an intermediate volume, or another suitable volume.

Seating the respective components at interstitial spaces of functionalized particles at the second substrate can involve one or more of: allowing the components to settle, under gravity, from a suspension and toward the functionalized particles; coupling the components with magnetic particles, and, upon application of a magnetic field, providing a biasing force to drive the components toward the functionalized particles; coupling the components with charged particles that promote movement of the components toward the functionalized particles; coupling the components with buoyant particles that promote movement of the components toward the functionalized particles; coupling the components with particles having a density that promotes movement of the components toward the functionalized particles; or seating the components in another suitable manner.

In variations, cells/nuclei transferred to the second substrate may not be pre-labeled according to Steps S510 and S520 and S610 and S620, such that unlabeled cells, nuclei, or other components of a sample can be transferred to a substrate having functionalized particles, and the un-labeled cells, un-labeled nuclei, or other components can be simultaneously tagged using spatial stochastic sequences, and also barcoded to perform single component (e.g., single cell, single nuclei) analyses.

In variations, components that are seated in steps S520 and S620 can be covered (e.g., sealed) with a layer. In variations, the layer 15 can be composed of optimal cutting temperature (OCT) compound (e.g., OCT compound alone, OCT compound combined with other process reagents, etc.), an oil, an aqueous material, a mesh, a hydrogel, or another suitable material. Covering can thus serve protective functions with respect to maintenance of cell or other target viability and general sample handling, and/or sample processing functions. The layer (e.g., of OCT) can have a thickness of: 2 micrometers thick, 3 micrometers thick, 4 micrometers thick, 5 micrometers thick, 6 micrometers thick, 7 micrometers thick, 8 micrometers thick, 9 micrometers thick, 10 micrometers thick, 11 micrometers thick, 12 micrometers thick, 13 micrometers thick, 14 micrometers thick, 14 micrometers thick, 15 micrometers thick, 16 micrometers thick, 17 micrometers thick, 18 micrometers thick, 19 micrometers thick, 20 micrometers thick, 21 micrometers thick, 22 micrometers thick, 23 micrometers thick, 24 micrometers thick, 25 micrometers thick, 26 micrometers thick, 26 micrometers thick, 27 micrometers thick, 28 micrometers thick, 29 micrometers thick, 30 micrometers thick, 35 micrometers thick, 40 micrometers thick, 50 micrometers thick, 60 micrometers thick, a thickness intermediate to thickness values described, or a thickness greater than 60 micrometers.

In an example, Steps S520 and S620 include: placing a 30 micrometer OCT section on top of the second substrate to seal in the components (e.g., cells, nuclei). The second substrate is then transferred to a container (e.g., a well plate, another container), and a volume (e.g., 1 ml) of lysis buffer is delivered to the container, followed by incubation (e.g., incubation on ice for 5 minutes). The second substrate is then washed (e.g., in 400 μL of RT wash buffer for 10-15 s).

Optionally, in some embodiments, Steps S520 and S620 can include capture (e.g., microfluidic capture, capture within microwells, capture within partitions, capture within droplets of an emulsion) and further barcoding of components after isolation of cells/nuclei, for further processing, by using partition-based single nucleus or single cell sequencing technologies. Identification of nuclei targets can further optionally be performed using optical detection of nuclei targets tagged with probes during tagging and barcoding of nuclei, without sequencing.

3.3 Library Preparation

Step S530 recites: generating a single cell sequencing library from amplicons generated from a set of reactions involving the set of labelled cells and molecules of the distribution of functionalized particles. Step S630 recites: generating a single nucleus sequencing library from amplicons generated from a set of reactions involving the set of labelled nuclei and molecules of the distribution of functionalized particles.

Library preparation can be performed according to embodiments, variations, and examples of library preparation steps described in U.S. patent application Ser. No. 17/895,633 filed on 25 Aug. 2022 and titled "Systems and Methods for Characterizing Locations of Target Analytes in Multi-Dimensional Space".

3.4 Single Component Analysis

Step S540 recites: returning a single cell analysis of the set of cells upon sequencing the single cell sequencing library. Step S640 recites: returning a single nucleus analysis of the set of nuclei upon sequencing the single nucleus sequencing library S640. Returning a single cell analysis and/or a single nucleus analysis can include sequencing nucleic acid material generated (e.g., from generated libraries from S530 and S640, respectively) from tagged cells and/or nuclei. Analysis techniques can include single nucleus RNA-seq (e.g., snRNA-seq, scRNA-seq, etc.), t-cell receptor (TCR) analyses, b-cell receptor (BCR) analyses (e.g., with receptor-ligand characterizations), ATAC-seq for assessment of chromatin accessibility (where handshake sequences/functionalized molecules described can include an adapter sequence that is the same as the adapters inserted into active chromatin by Tn5 transposase), generation of Hi-C sequencing libraries, generation of spatially-resolved methylation sequencing libraries, generation of single cell/ single nuclei chromatin immunoprecipitation sequencing libraries, generation of spatially-resolved single cell/single nuclei enzyme-tethering chromatin profiling libraries, generation of single cell/single-nuclei spatially resolved proteomic libraries, generation of other multiomic spatially-resolved libraries (e.g., where the barcode that serves as a spatial address needs be tagged by a cell barcode for only one of the omic parts of the multiomic assay), processing of nuclei and non-nuclei targets of formalin-fixed and paraffin-embedded (FFPE) samples, analysis of nuclear DNA, analysis of nuclear proteins, and/or other analyses.

Positions of tagged single nuclei and/or single cells can be also be determined and subsequently mapped using centroid approaches or other approaches, as described above, where centroids of barcodes serving as spatial addresses are used to approximate positions of each nuclei isolated, and the positions of the corresponding nuclei are then mapped.

3.5 Method—Alternative Single Cell Analyses

As shown in FIG. 10, an embodiment of a method 700 for characterization of a set of single cells or single nuclei in multiple dimensions, can include: combining a set of functionalized particles with a set of single cells and/or a set of single nuclei, wherein a ratio of a number of functionalized particles to a number of single cells and/or single nuclei is greater than one S710 (e.g., 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, etc.); retaining single cells and/or single nuclei within recesses (e.g., crevices, pores, other surface features, etc.) of the set of functionalized particles S720 (e.g., where a single cell or single nucleus associates with no more than one functionalized particle of the set of functionalized particles); stabilizing the set of functionalized particles with associated single cells and/or single nuclei within a matrix (e.g., hydrogel matrix, other matrix), wherein the matrix can be transitioned between a set phase and a non-set phase, and wherein the matrix allows for diffusion of material below a first size threshold to and/or between the set of functionalized particles, and prevents material above a second size threshold from diffusion S730; lysing the set of single cells (if single cells are present) with a lysis buffer, with or without increasing a temperature of the lysis buffer, wherein the lysis buffer is introduced to the set of single cells through the matrix S740; performing a hybridization operation with content (e.g., mRNA content, other nucleic acid content, conjugated protein content, etc.) of the set of single cells and/or set of single nuclei with the set of functionalized particles, wherein content of a single cell or single nucleus can hybridize with more than one functionalized particle of the set of functionalized particles, wherein the hybridization operation tags target content of a single cell or single nucleus S750; transitioning the matrix from the set phase to the non-set phase, in coordination with performing a reverse transcription operation, a second strand synthesis operation, and a cDNA amplification operation after the hybridization operation S760; generating a sequencing library from amplicons generated from the cDNA amplification operation S770; and returning a single cell and/or single nucleus analysis of the set of cells/set of nuclei upon processing the sequencing library S780, wherein subsets of the set of functionalized particles associated with target material from a single cell/single nucleus are associated based upon a barcode (e.g., a spatial barcode, a cell barcode) having a nucleotide sequence (e.g., a stochastic sequence) associated with the single cell/single nucleus. When combined with spatial information (e.g., with use of spatial barcodes described), the methods described can generate and return associations between genotypic features and phenotypic features of biological sample material.

3.6 Method—Smearing Artifact Mitigation

Variations of the methods described can include steps for mitigation of issues associated with undesired diffusion of handshake molecules and/or targets away from each other, such that resultant target positions determined are inaccurate. Target movement can be attributed to one or more of: presence of highly-expressed targets (e.g., target genes); diffusion or directional flow of targets or functionalized molecules away from originating positions, due to sample processing steps and/or apparatuses that allow for target flow away from originating positions within a sample; and provision of a distribution of functionalized particles having a substantially larger footprint (e.g., attributed area, number of functionalized particles, etc.) than a footprint occupied by the sample.

Mitigation of smearing can be enabled by one or more of: increasing density or number of available tagging sites on functionalized molecules used to spatially tag targets of the sample; increasing volumes of chambers used for hybridization and washing steps, in order to reduce undesired hybridization of target molecules (e.g., of highly-expressed genes) to non-nearby functionalized particles; matching an area (or attempting to match an area) of a footprint of a distribution of functionalized particles with a footprint of a sample; blocking tagging molecules of exposed functionalized particles of a distribution of functionalized particles after applying a sample to the distribution of functionalized particles, where exposed functionalized particles include particles not covered by the sample, and where blocking tagging molecules comprises adding adenosine (dA) blockers (or other blockers) to hybridization buffers used during assay workflows; implementing agitation of solutions involved in hybridization, during hybridization steps of assay workflows; applying less efficient hybridization buffers and/or longer incubation times, in order to prevent leakage; and performing other suitable operations.

In examples, directional flow of targets and/or handshake sequences, which can result in a smearing effect in generated maps, can correlated with orientation of the substrate within a chamber containing hybridization buffer for hybridization steps, where a predominant direction of transmission of a system unit into a chamber of hybridization buffer, and/or a predominant direction of removal of a system unit from a chamber of hybridization buffer is correlated with the direction of smearing (e.g., loose/unbound targets are moved and tagged during transmission or removal from hybridization buffer).

In one variation, methods involving hybridization of targets to functionalized particles can include application of a layer 15 (e.g., smear-prevention layer) over the sample, such that the sample is sandwiched between the layer 15 and the distribution of functionalized particles (e.g., during hybridization steps) to prevent target drift and/or to prevent smearing in maps generated from processes and reactions involving the distributions(s) of functionalized particles (see FIG. 11A).

Figure 11B:
FIG. 11B depicts a variation of a method for preventing smearing artifacts and/or background artifacts.

In one variation, the layer 15 can include a layer of optimal cutting temperature (OCT) compound, and a method 800 for application of the layer 15 (e.g., of OCT compound) can include, as shown in FIG. 11B: positioning a sample (e.g., frozen tissue slice, other sample) at the substrate over at least a portion of the distribution of functionalized particles S810; positioning a layer (e.g., a layer of OCT compound) over the sample S820; optionally transmitting heat to the sample and to the layer S830; and performing subsequent sample processing steps (e.g., hybridization steps) S840, as described. In variations, methods for application of the layer can include re-freezing the sample and the layer (e.g., of OCT compound) prior to subsequent processing.

In variations, the layer (e.g., of OCT compound) can be generated from a solidified (e.g., frozen) body of material, where the layer can be sectioned from the solidified body. In variations, sectioning can be performed using one or more of: cutting, laser cutting, shaving, or another suitable method. In variations, the layer 15 may not be a section, and can alternatively be applied by aspiration and delivery, spraying, coating, spinning, or other methods of application of a liquid volume of material of the layer.

In variations, the thickness of the layer can be: 2 micrometers thick, 3 micrometers thick, 4 micrometers thick, 5 micrometers thick, 6 micrometers thick, 7 micrometers thick, 8 micrometers thick, 9 micrometers thick, 10 micrometers thick, 11 micrometers thick, 12 micrometers thick, 13 micrometers thick, 14 micrometers thick, 14 micrometers thick, 15 micrometers thick, 16 micrometers thick, 17 micrometers thick, 18 micrometers thick, 19 micrometers thick, 20 micrometers thick, 21 micrometers thick, 22 micrometers thick, 23 micrometers thick, 24 micrometers thick, 25 micrometers thick, 26 micrometers thick, 26 micrometers thick, 27 micrometers thick, 28 micrometers thick, 29 micrometers thick, 30 micrometers thick, 35 micrometers thick, 40 micrometers thick, 50 micrometers thick, 60 micrometers thick, a thickness intermediate to thickness values described, or a thickness greater than 60 micrometers.

In variations, material of the layer (e.g., the OCT compound) can be diluted, which can improve diffusion of process reagents across the layer during sample processing while still preventing target drift and tagging problems. As such, the thickness of the layer can be adjusted and/or material of the layer can be diluted to provide suitable conditions for simultaneously achieving reagent transmission and target drift prevention. Dilution of the layer can be performed in a way that does not significantly affect temperature-associated performance aspects (e.g., freezing behavior, melting behavior, etc.) in relation to sample processing steps described.

In variations where application of the layer results in reduced sensitivity with respect to number of targets tagged (e.g., targets tagged at "correct positions", without smearing) from the tissue sample, material of the layer can be combined with sample processing reagents associated with various tagging steps and/or steps for promoting interactions between targets and functionalized particles.

In one example, material of the layer can include a combination of OCT compound with: a hybridization buffer, a sample lysis buffer, reagents for crosslinking, reagents for cleaving (e.g., of molecules with cleavage sites), and/or other suitable materials). As such, combination of the material(s) of the layer with process reagents can promote efficiency of sample processing steps, improve sensitivity of tagging, and/or provide other suitable benefits.

Application of the layer (e.g., layer of OCT compound) can result in a percent reduction of smearing and background artifacts in generated maps, where in examples, the percent reduction in smearing was: greater than 60%, greater than 61%, greater than 62%, greater than 63%, greater than 64%, greater than 65%, greater than 66%, greater than 67%, greater than 68%, greater than 69%, greater than 70%, greater than 71%, greater than 72%, greater than 73%, greater than 74%, greater than 75%, greater than 76%, greater than 77%, greater than 78%, greater than 79%, greater than 80%, greater than 81%, greater than 82%, greater than 83%, greater than 84%, greater than 85%, greater than 86%, greater than 87%, greater than 88%, greater than 89%, greater than 90%, or greater. In examples, the percent reduction in smearing was determined by comparing values (e.g., percentage values, number values) of functionalized particles to which noise (e.g., noise associated with target movement and re-tagging) was attributed, between a first section of a tissue sample and a second section of the tissue sample, where the smear-preventing layer was added to the first section, and was not added to the second section. In examples, the percent reduction in smearing was determined by comparing values (e.g., percentage values, number values) of UMIs/bead detected during sequencing, to which noise (e.g., noise associated with target movement and re-tagging) was attributed, between a first section of a tissue sample and a second section of the tissue sample, where the smear-preventing layer was added to the first section, and was not added to the second section.

Figure 12:
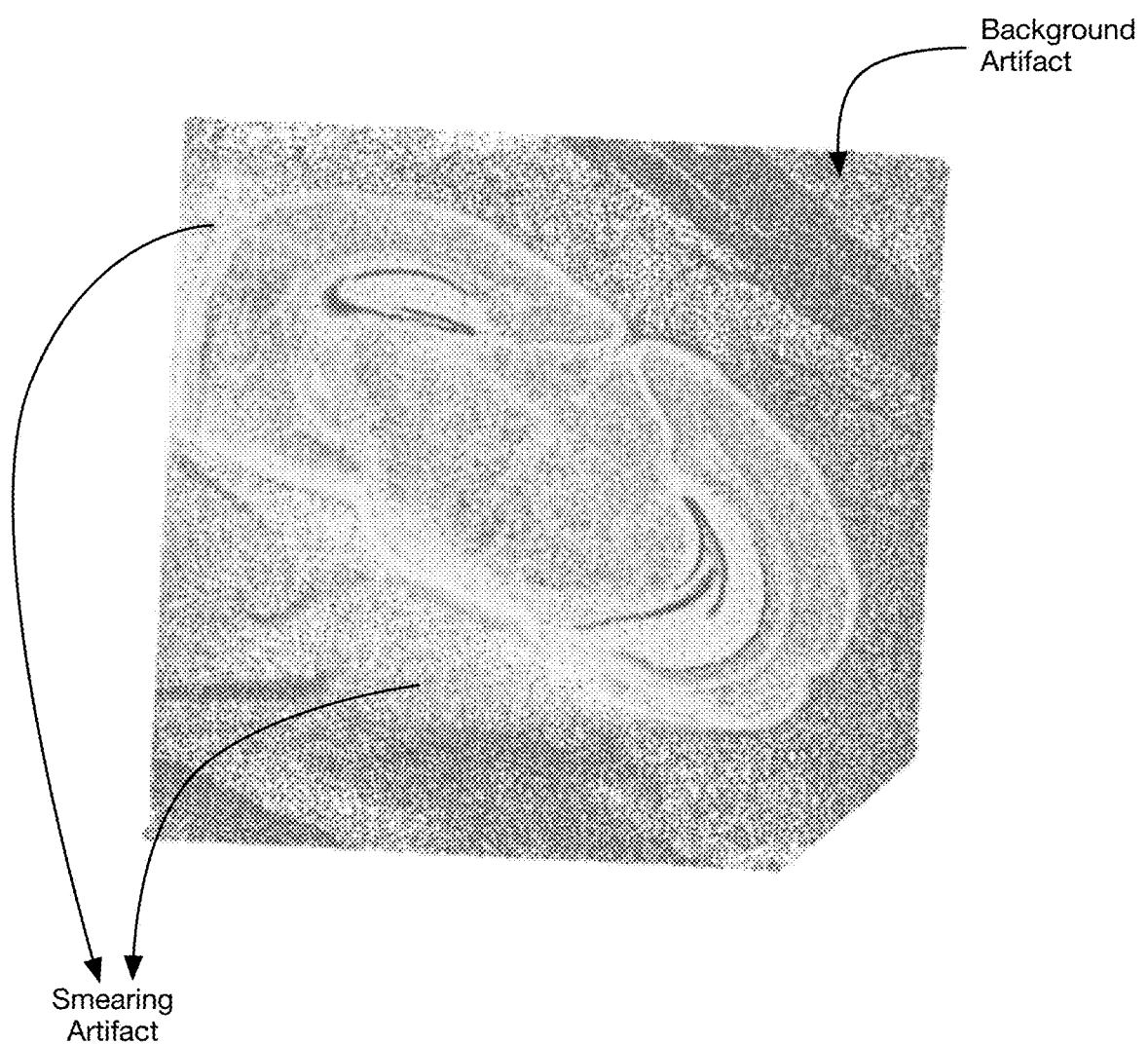
FIG. 12 illustrates an exemplary smearing artifact and background artifact.

Mitigation of smearing can additionally or alternatively be enabled using bioinformatics-informed approaches to processing of data generated using units of the systems described, where data processing architecture can be structured to remove background signal artifacts and directional signal artifacts (which are observed as "smearing" in generated spatial maps), where background artifacts and/or directional signal artifacts can be attributed to leakage of targets away from originating positions, and subsequent re-tagging by tagging molecules of the distribution of functionalized particles, as described above. An example of each type of artifact is shown in FIG. 12.

A method 900 for removing signal artifacts can include, as shown in FIG. 13: for a distribution of functionalized particles, omitting mapping of data from a first category of particles of the distribution of functionalized particles, wherein sequences acquired from the first category of particles each have UMI counts above a first threshold S910; omitting mapping of data from a second category of particles of the distribution of functionalized particles, wherein particles of the second category of particles each have an associated density greater than a second threshold S920; and omitting mapping of data from a third category of particles of the distribution of functionalized particles, wherein particles of the third category of particles each have an associated density greater than a third threshold S930.

In variations, the first threshold can be a threshold of greater than 70 UMI counts, a threshold of greater than 75 UMI counts, a threshold of greater than 80 UMI counts, a threshold of greater than 85 UMI counts, a threshold of greater than 90 UMI counts, a threshold of greater than 95 UMI counts, a threshold of greater than 100 UMI counts, a threshold of greater than 105 UMI counts, a threshold of greater than 110 UMI counts, a threshold of greater than 120 UMI counts, a threshold of greater than 130 UMI counts, a threshold of greater than 140 UMI counts, a threshold of greater than 150 UMI counts, or another UMI count threshold.

In variations, the second threshold can be a threshold of greater than a first number of particles within a first area, wherein the first number of particles is 1 particle, 2 particles, 3 particles, 4 particles, 5 particles, 6 particles, 7 particles or greater; and wherein the first area is an area of 15 micrometers by 15 micrometers, 20 micrometers by 20 micrometers, 25 micrometers by 25 micrometers, 30 micrometers by 30 micrometers, 35 micrometers by 35 micrometers, 40 micrometers by 40 micrometers, 45 micrometers by 45 micrometers, 50 micrometers by 50 micrometers, 60 micrometers by 60 micrometers, 70 micrometers by 70 micrometers, or another suitable area. The second density threshold can be a finer density threshold, in comparison to the third threshold.

In variations, the third threshold can be a threshold of greater than a second number of particles within a second area, wherein the second number of particles is 7 particles, 8 particles, 9 particles, 10 particles, 11 particles, 12 particles, 13 particles, 14 particles, 15 particles, or greater; and wherein the second area is an area of 70 micrometers by 70 micrometers, 75 micrometers by 75 micrometers, 80 micrometers by 80 micrometers, 85 micrometers by 85 micrometers, 90 micrometers by 90 micrometers, 95 micrometers by 95 micrometers, 100 micrometers by 100 micrometers, 110 micrometers by 110 micrometers, 120 micrometers by 120 micrometers, 130 micrometers by 130 micrometers, 150 micrometers by 150 micrometers, 200 micrometers by 200 micrometers, or another suitable area. The second density threshold can be a coarser density threshold, in comparison to the second threshold.

In a specific example, the first threshold is a threshold of greater than or equal to 100 UMIs, the second threshold is a threshold of greater than 5 particles within a 40 micrometer by 40 micrometer area, and the third threshold is a threshold of greater than 10 particles within a 100 micrometer by 100 micrometer area.

Variations of the method 900 can involve adjustment of thresholds based upon sample type (e.g., tissue type), presence or absence of highly-expressed genes, substrate and functionalized particle characteristics (e.g., size of distribution of functionalized particles, footprint occupied by functionalized particles at the substrate, size of substrate relative to sample size, particle size(s), etc.), processing aspects (e.g., volumes and types of solutions used for hybridization, involvement of agitation during hybridization steps, sequencing depth, and/or other factors.

Variations of the method 900 can involve omission of data used in mapping, based upon other suitable thresholds, where thresholds can be based upon other parameters that distinguish desired signals for mapping, from background and directional signals. Additionally or alternatively, removal of artifacts can be performed with manual removal (e.g., with manual selection of data to be removed, through a user interface for transforming data into target maps) and/or clustering algorithms.

Variations of the method 900 can involve omitting/subtracting data from functionalized particles associated with a smear (for mapping purposes), and/or removing an in-tissue smear by subtracting characteristic transcriptomic patterns in the smear from the tissue.

The described bioinformatics approaches can result in a percent reduction of smearing and background artifacts in generated maps, where in examples, the percent reduction in smearing was: greater than 60%, greater than 61%, greater than 62%, greater than 63%, greater than 64%, greater than 65%, greater than 66%, greater than 67%, greater than 68%, greater than 69%, greater than 70%, greater than 71%, greater than 72%, greater than 73%, greater than 74%, greater than 75%, greater than 76%, greater than 77%, greater than 78%, greater than 79%, greater than 80%, greater than 81%, greater than 82%, greater than 83%, greater than 84%, greater than 85%, greater than 86%, greater than 87%, greater than 88%, greater than 89%, greater than 90%, greater than 95%, or 100%. In examples, the percent reduction in smearing was determined by comparing values (e.g., percentage values, number values) of functionalized particles to which noise (e.g., noise associated with target movement and re-tagging) was attributed, between a first spatial map of targets generated without application of described bioinformatics processes, and a second spatial map of targets generated with application of described bioinformatics processes. In examples, the percent reduction in smearing was determined by comparing values (e.g., percentage values, number values) of UMIs/bead detected during sequencing, to which noise (e.g., noise associated with target movement and re-tagging) was attributed, between a first spatial map of targets generated without application of described bioinformatics processes, and a second spatial map of targets generated with application of described bioinformatics processes.

The method 400 can include other suitable steps and/or enable other downstream applications.

For instance, images can be taken of the sample in coordination with tagging and spatially-contextualizing targets of the sample. Images can be obtained using microscopes configured for light, bright field, dark field, phase contrast, fluorescence, reflection, interference, or confocal imaging. A biological specimen can be stained prior to imaging to provide contrast between different regions or cells. In some embodiments, more than one stain can be used to image different aspects of the specimen (e.g. different regions of a tissue, different cells, specific subcellular components or the like). In other embodiments, a biological specimen can be imaged without staining. An image of a biological specimen can be obtained at a desired resolution, for example, to distinguish tissues, cells or subcellular components. Accordingly, the resolution can be sufficient to distinguish components of a biological specimen that are separated by at least 0.5 $\mu$m, 1 $\mu$m, 5 $\mu$m, 10 $\mu$m, 50 $\mu$m, 100 $\mu$m, 500 $\mu$m, 1 mm or more. Alternatively or additionally, the resolution can be set to distinguish components of a biological specimen that are separated by at least 1 mm, 500 $\mu$m, 100 $\mu$m, 50 $\mu$m, 10 $\mu$m, 5 $\mu$m, 1 $\mu$m, 0.5 $\mu$m or less.

A method set forth herein can include a step of correlating locations in an image of a biological specimen with hand-shake sequences of functionalized molecules that are attached to individual beads to which the biological specimen is, was or will be contacted. Accordingly, characteristics of the biological specimen that are identifiable in the image can be correlated with the nucleic acids that are found to be present in their proximity. Any of a variety of morphological characteristics can be used in such a correlation, including for example, cell shape, cell size, tissue shape, staining patterns, presence of particular proteins (e.g., as detected by immunohistochemical stains) or other characteristics that are routinely evaluated in pathology or research applications. Accordingly, the biological state of a tissue or its components as determined by visual observation can be correlated with molecular biological characteristics as determined by spatially resolved nucleic acid analysis.

4. COMPUTER SYSTEMS

Figure 14:
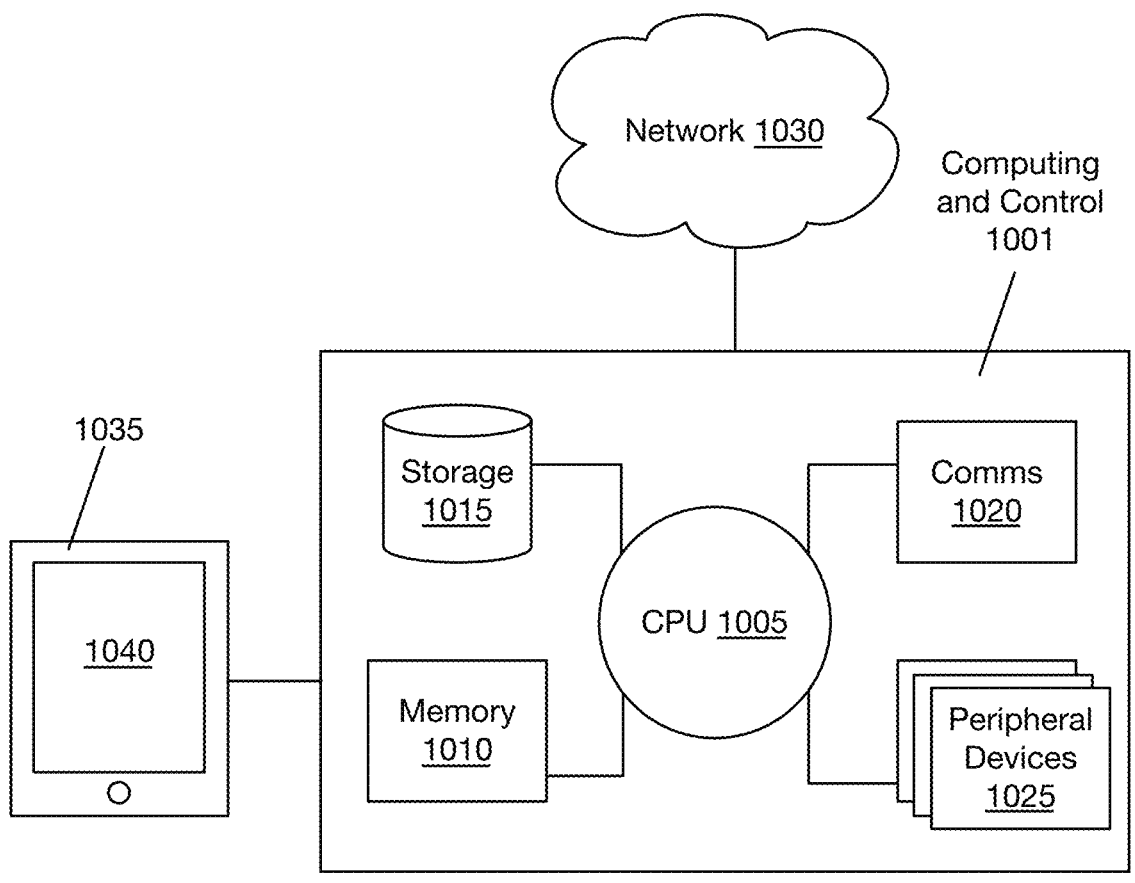
FIG. 14 illustrates a computer system that is programmed or otherwise configured to implement methods provided herein.

The present disclosure provides computer systems that are programmed to implement methods of the disclosure. FIG. 14 shows a computer system 1001 that is programmed or otherwise configured to, for example, perform steps of methods for generating spatial maps of a distribution of targets of a sample, by one or more processes described.

The computer system 1001 can regulate various aspects of analysis, calculation, and generation of the present disclosure, such as, for example, generating a spatial map of a distribution of targets of a sample by a set of processes, described above. The computer system 1001 can be an electronic device of a user or a computer system that is remotely located with respect to the electronic device. The electronic device can be a mobile electronic device.

The computer system 1001 includes a central processing unit (CPU, also "processor" and "computer processor" herein) 1005, which can be a single core or multi core processor, or a plurality of processors for parallel processing. The computer system 1001 also includes memory or memory location 1010 (e.g., random-access memory, read-only memory, flash memory), electronic storage unit 1015 (e.g., hard disk), communication interface 1020 (e.g., network adapter) for communicating with one or more other systems, and peripheral devices 1025, such as cache, other memory, data storage and/or electronic display adapters. The memory 1010, storage unit 1015, interface 1020 and peripheral devices 1025 are in communication with the CPU 1005 through a communication bus (solid lines), such as a motherboard. The storage unit 1015 can be a data storage unit (or data repository) for storing data. The computer system 1001 can be operatively coupled to a computer network ("network") 1030 with the aid of the communication interface 1020. The network 1030 can be the Internet, an internet and/or extranet, or an intranet and/or extranet that is in communication with the Internet.

In some embodiments, the network 1030 is a telecommunication and/or data network. The network 1030 can include one or more computer servers, which can enable distributed computing, such as cloud computing. For example, one or more computer servers may enable cloud computing over the network 1030 ("the cloud") to perform various aspects of analysis, calculation, and generation of the present disclosure, such as, for example, generating a plurality of droplets within a collecting container at a predetermined rate or variation in polydispersity. Such cloud computing may be provided by cloud computing platforms such as, for example, Amazon Web Services (AWS), Microsoft Azure, Google Cloud Platform, and IBM cloud. In some embodiments, the network 1030, with the aid of the computer system 1001, can implement a peer-to-peer network, which may enable devices coupled to the computer system to behave as a client or a server.

The CPU 1005 may comprise one or more computer processors and/or one or more graphics processing units (GPUs). The CPU 1005 can execute a sequence of machine-readable instructions, which can be embodied in a program or software. The instructions may be stored in a memory location, such as the memory 1010. The instructions can be directed to the CPU 1005, which can subsequently program or otherwise configure the CPU 1005 to implement methods of the present disclosure. Examples of operations performed by the CPU 1005 can include fetch, decode, execute, and writeback.

The CPU 505 can be part of a circuit, such as an integrated circuit. One or more other components of the system 1001 can be included in the circuit. In some embodiments, the circuit is an application specific integrated circuit (ASIC).

The storage unit 1015 can store files, such as drivers, libraries and saved programs. The storage unit 1015 can store user data, e.g., user preferences and user programs. In some embodiments, the computer system 1001 can include one or more additional data storage units that are external to the computer system 1001, such as located on a remote server that is in communication with the computer system 1001 through an intranet or the Internet.

The computer system 1001 can communicate with one or more remote computer systems through the network 1030. For instance, the computer system 1001 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1001 via the network 1030.

Methods as described herein can be implemented by way of machine (e.g., computer processor) executable code stored on an electronic storage location of the computer system 1001, such as, for example, on the memory 1010 or electronic storage unit 1015. The machine executable or machine readable code can be provided in the form of software. During use, the code can be executed by the processor 1005. In some embodiments, the code can be retrieved from the storage unit 1015 and stored on the memory 1010 for ready access by the processor 1005. In some situations, the electronic storage unit 1015 can be precluded, and machine-executable instructions are stored on memory 1010.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Embodiments of the systems and methods provided herein, such as the computer system 1001, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, or disk drives, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1001 can include or be in communication with an electronic display 1035 that comprises a user interface (UI) 1040 for providing, for example, a visual display indicative of generating a spatial map of a distribution of targets of a sample by a set of processes, as described above. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 1005. The algorithm can, for example, generate one or more spatial maps with performance characteristics described.

5. CONCLUSIONS

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or, if applicable, portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams or flowchart illustration, and combinations of blocks in the block diagrams or flowchart illustration, can be implemented by special purpose hardware-based systems that perform the specified functions or acts, or combinations of special purpose hardware and computer instructions.

It should be understood from the foregoing that, while particular implementations have been illustrated and described, various modifications may be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:
1. A method comprising:
applying a layer of optimum cutting temperature (OCT) compound to a tissue sample;

tagging a distribution of nuclei from the tissue sample with a set of functionalized molecules, wherein a functionalized molecule of the set of functionalized molecules comprises:
a handshake sequence;
a barcode sequence that serves as a spatial address; and
a releasable linker,
wherein tagging comprises:
applying a stimulus to the releasable linkers of the set of functionalized molecules, wherein upon application of the stimulus, a set of handshake sequences and barcode sequences are cleaved from the set of functionalized molecules to allow diffusion of the set of handshake sequences and barcode sequences toward the distribution of nuclei to tag the distribution of nuclei;
isolating a set of nuclei from the tissue sample after the OCT compound is applied; and
generating and displaying a spatial map of the isolated set of nuclei from the tissue sample within an interface of an electronic display, wherein generating the spatial map comprises recovering and mapping positions of more than 30% of nuclei originally present in the tissue sample.
2. A method comprising:
applying a layer of optimum cutting temperature (OCT) compound to a tissue sample;
tagging a distribution of nuclei from the tissue sample with a set of functionalized molecules, wherein a functionalized molecule of the set of functionalized molecules comprises:
a handshake sequence;
a barcode sequence that serves as a spatial address; and
a releasable linker,
wherein tagging comprises:
applying a stimulus to the releasable linkers of the set of functionalized molecules, wherein upon application of the stimulus, a set of handshake sequences and barcode sequences are cleaved from the set of functionalized molecules to allow diffusion of the set of handshake sequences and barcode sequences toward the distribution of nuclei to tag to the distribution of nuclei;
isolating a set of nuclei from the tissue sample after the OCT compound is applied; and
generating and displaying a spatial map of the isolated set of nuclei from the tissue sample within an interface of an electronic display, wherein generating the spatial map is performed within a duration of 2 hours.
3. The method of claim 2, further comprising decoding the set of barcode sequences by performing a set of iterations of sequencing with error-reduction by dynamic annealing and ligation (SEDAL) upon the set of barcode sequences coupled to a substrate, wherein decoding the set of barcode sequences has a passing rate greater than 90% as determined by a set of criteria, and wherein the set of criteria comprises a substrate coverage criterion and a criterion regarding amount of empty space on the substrate.
4. A method comprising:
applying a layer of optimum cutting temperature (OCT) compound to a tissue sample;
tagging a distribution of nuclei from the tissue sample with a set of functionalized molecules, wherein a functionalized molecule of the set of functionalized molecules comprises:
a handshake sequence;
a barcode sequence that serves as a spatial address; and
a releasable linker, wherein tagging comprises:

applying a stimulus to the releasable linkers of the set of functionalized molecules, wherein upon application of the stimulus, a set of handshake sequences and barcode sequences are cleaved from the set of functionalized molecules to allow diffusion of the set of handshake sequences and barcode sequences toward the distribution of nuclei to tag the distribution of nuclei;

isolating a set of nuclei from the tissue sample after the OCT compound is applied; and generating and displaying a spatial map of the isolated set of nuclei from the tissue sample within an interface of an electronic display, upon releasing the set of handshake sequences and barcode sequences for diffusion toward the distribution of nuclei.

5. A method comprising:

applying a layer of optimum cutting temperature (OCT) compound to a tissue sample;

generating and displaying a spatial map of a set of nuclei of the tissue sample upon:

processing the tissue sample comprising a distribution of nuclei with a substrate comprising a set of functionalized molecules, wherein a representative functionalized molecule of the set of functionalized molecules comprises:

a handshake sequence that binds to a nucleus of the distribution of nuclei, a barcode sequence that serves as a spatial address, and a releasable linker;

tagging the distribution of nuclei with handshake sequences of the set of functionalized molecules, wherein tagging comprises:

applying a stimulus to the releasable linkers of the set of functionalized molecules, wherein upon application of the stimulus, a set of handshake sequences and barcode sequences are cleaved from the set of functionalized molecules to allow diffusion of the set of handshake sequences and barcode sequences toward the distribution of nuclei to tag the distribution of nuclei;

isolating a set of nuclei of the tissue sample after the OCT compound is applied;

determining a set of sequences of resultant molecules generated from the set of nuclei and the set of functionalized molecules, thereby determining a set of spatial positions of the set of nuclei based upon the barcode sequences associated with each nucleus of the set of nuclei; and generating and displaying the spatial map of the set of nuclei from the set of spatial positions within an interface of an electronic display.

6. The method of claim 5, wherein generating the spatial map is performed within a duration of 2 hours.

7. The method of claim 5, wherein isolating the set of nuclei comprises recovering more than 30% of nuclei originally present in the tissue sample.

8. The method of claim 7, wherein isolating the set of nuclei comprises trituration of the tissue sample with an isolation buffer.

9. The method of claim 7, wherein isolating the set of nuclei comprises isolating the set of nuclei with an irrigator.

10. The method of claim 5, wherein the releasable linker is responsive to a photocleaving mechanism.

11. The method of claim 5, wherein the set of functionalized molecules comprises a first subset of releasable linkers that cleave in response to a first stimulus, and a second subset of releasable linkers that cleave in response to a second stimulus.

12. The method of claim 11, wherein the first stimulus is a first wavelength of light, and wherein the second stimulus is a second wavelength of light.

13. The method of claim 5, wherein determining the set of spatial positions comprises determining a position of a nucleus from a centroid of a subset of spatial positions of a subset of barcode sequences of a subset of functionalized molecules that tagged the nucleus.

14. The method of claim 5, wherein the method is performed at or below 4 degrees C.

15. The method of claim 5, wherein the set of functionalized molecules is distributed across a distribution of particles coupled to the substrate by an adhesive.

16. The method of claim 5, further comprising covering the set of functionalized molecules of the substrate with a masking layer and removing the masking layer prior to applying the stimulus.

* * * * *